United States Patent
Sourlis et al.

(10) Patent No.: US 12,060,398 B2
(45) Date of Patent: Aug. 13, 2024

(54) FIBROUS PROTEINACEOUS NETWORKS AND METHODS OF USE THEREOF

(71) Applicant: President and Fellows of Harvard College, Cambridge, MA (US)

(72) Inventors: Arjirios Sourlis, Zurich (CH); Anna Duraj-Thatte, Kensington, CA (US); Avinash Manjula Basavanna, Allston, MA (US); Neel Satish Joshi, Somerville, MA (US)

(73) Assignee: Northeastern University, Boston, MA (US)

( * ) Notice: Subject to any disclaimer, the term of this patent is extended or adjusted under 35 U.S.C. 154(b) by 628 days.

(21) Appl. No.: 17/254,019

(22) PCT Filed: Jun. 21, 2019

(86) PCT No.: PCT/US2019/038501
§ 371 (c)(1),
(2) Date: Dec. 18, 2020

(87) PCT Pub. No.: WO2019/246537
PCT Pub. Date: Dec. 26, 2019

(65) Prior Publication Data
US 2021/0163558 A1 Jun. 3, 2021

Related U.S. Application Data

(60) Provisional application No. 62/687,991, filed on Jun. 21, 2018.

(51) Int. Cl.
| | |
|---|---|
| C07K 14/47 | (2006.01) |
| A61L 15/32 | (2006.01) |
| A61L 15/42 | (2006.01) |
| A61L 24/00 | (2006.01) |
| A61L 24/10 | (2006.01) |
| A61L 27/22 | (2006.01) |
| A61L 27/52 | (2006.01) |
| B33Y 70/00 | (2020.01) |
| C07K 14/75 | (2006.01) |
| C07K 14/78 | (2006.01) |
| C09D 11/04 | (2006.01) |

(52) U.S. Cl.
CPC .......... *C07K 14/4711* (2013.01); *A61L 15/32* (2013.01); *A61L 15/42* (2013.01); *A61L 24/0031* (2013.01); *A61L 24/108* (2013.01); *A61L 27/227* (2013.01); *A61L 27/52* (2013.01); *B33Y 70/00* (2014.12); *C07K 14/75* (2013.01); *C07K 14/78* (2013.01); *C09D 11/04* (2013.01); *C07K 2319/00* (2013.01)

(58) Field of Classification Search
None
See application file for complete search history.

(56) References Cited

U.S. PATENT DOCUMENTS

| | | |
|---|---|---|
| 7,569,660 B1 | 8/2009 | Lindquist et al. |
| 2006/0019871 A1 | 1/2006 | Takada et al. |
| 2007/0009507 A1 | 1/2007 | Serre et al. |
| 2016/0220727 A1 * | 8/2016 | Lu .................... C07K 14/43504 |

FOREIGN PATENT DOCUMENTS

| | | | | |
|---|---|---|---|---|
| WO | WO-2017087827 A1 * | 5/2017 | ....... | C07K 14/43518 |
| WO | WO-2019/246537 A8 | 10/2020 | | |

OTHER PUBLICATIONS

Murr L. "Structures and Properties of Keratin-Based and Related Biological Materials" Handbook of Materials Structures, Properties, Processing and Performance. Springer Intl. Publishing Switzerland. (Year: 2015).*

International Search Report and Written Opinion for International Application No. PCT/US2019/038501 dated Nov. 8, 2019.

* cited by examiner

*Primary Examiner* — Sudhakar Katakam
*Assistant Examiner* — Zachary J Miknis
(74) *Attorney, Agent, or Firm* — Foley Hoag LLP; Dana M. Gordon; Alexander J. Chatterley

(57) ABSTRACT

Disclosed herein are engineered bacteria that manufacture biofilms from bacterial amyloid structures. These biofilms and biofilm matrices are capable of generating fibrous proteinaceous networks and being used as 3D-printing inks.

25 Claims, 17 Drawing Sheets

Specification includes a Sequence Listing.

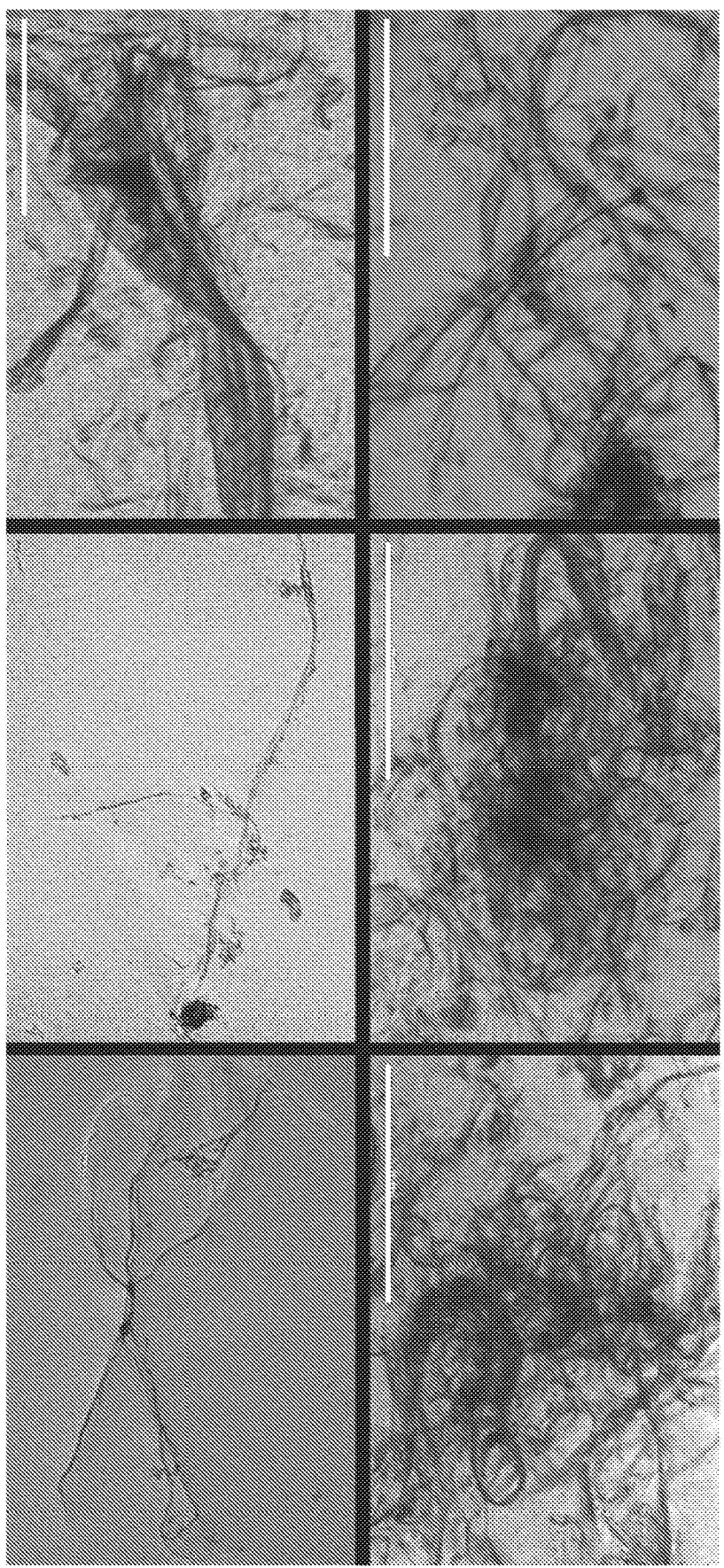

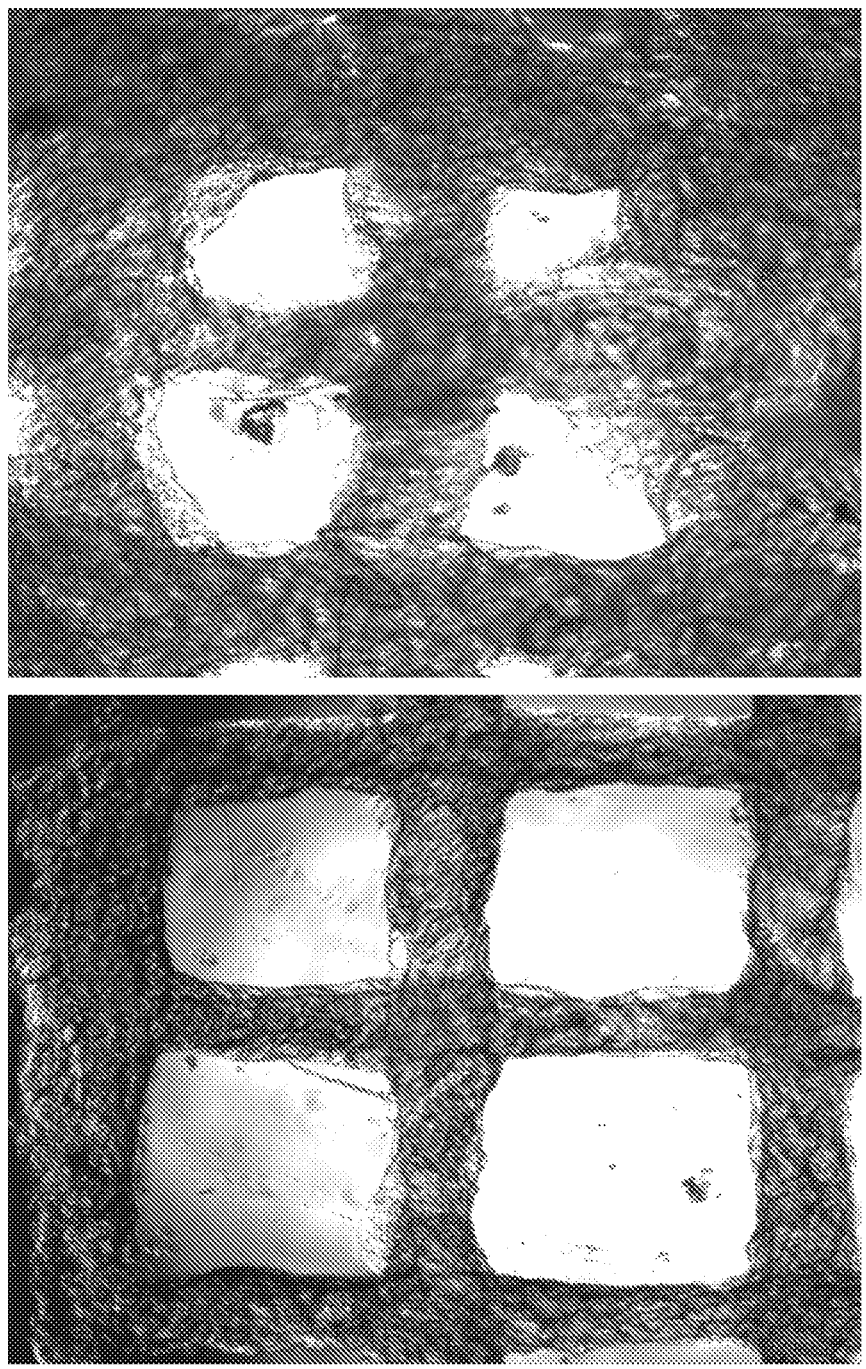

SEQUENCE LISTING

<160> NUMBER OF SEQ ID NOS: 13

<210> SEQ ID NO 1
<211> LENGTH: 151
<212> TYPE: PRT
<213> ORGANISM: Escherichia coli

<400> SEQUENCE: 1

Met Lys Leu Leu Lys Val Ala Ala Ile Ala Ala Ile Val Phe Ser Gly
1               5                   10                  15

Ser Ala Leu Ala Gly Val Val Pro Gln Tyr Gly Gly Gly Gly Asn His
                20                  25                  30

Gly Gly Gly Gly Asn Asn Ser Gly Pro Asn Ser Glu Leu Asn Ile Tyr
            35                  40                  45

Gln Tyr Gly Gly Gly Asn Ser Ala Leu Ala Leu Gln Thr Asp Ala Arg
        50                  55                  60

Asn Ser Asp Leu Thr Ile Thr Gln His Gly Gly Gly Asn Gly Ala Asp
65                  70                  75                  80

Val Gly Gln Gly Ser Asp Asp Ser Ser Ile Asp Leu Thr Gln Arg Gly
                85                  90                  95

Phe Gly Asn Ser Ala Thr Leu Asp Gln Trp Asn Gly Lys Asn Ser Glu
                100                 105                 110

Met Thr Val Lys Gln Phe Gly Gly Gly Asn Gly Ala Ala Val Asp Gln
            115                 120                 125

Thr Ala Ser Asn Ser Ser Val Asn Val Thr Gln Val Gly Phe Gly Asn
        130                 135                 140

Asn Ala Thr Ala His Gln Tyr
145                 150

<210> SEQ ID NO 2
<211> LENGTH: 590
<212> TYPE: PRT
<213> ORGANISM: Homo sapiens

<400> SEQUENCE: 2

Met Ser Arg Gln Ser Ser Val Ser Phe Arg Ser Gly Gly Ser Arg Ser
1               5                   10                  15

Phe Ser Thr Ala Ser Ala Ile Thr Pro Ser Val Ser Arg Thr Ser Phe
                20                  25                  30

-continued

| | | | | | | | | | | | |
|---|---|---|---|---|---|---|---|---|---|---|---|
|Thr|Ser|Val|Ser 35|Arg|Ser|Gly 40|Gly|Gly|Gly 45|Phe|Gly|Arg|

Val Ser Leu Ala Gly Ala Cys Gly Val Gly Gly Tyr Gly Ser Arg Ser
 50                  55                  60

Leu Tyr Asn Leu Gly Gly Ser Lys Arg Ile Ser Ile Ser Thr Arg Gly
 65                  70                  75                  80

Gly Ser Phe Arg Asn Arg Phe Gly Ala Gly Ala Gly Gly Gly Tyr Gly
                  85                  90                  95

Phe Gly Gly Gly Ala Gly Ser Gly Phe Gly Phe Gly Gly Gly Ala Gly
                 100                 105                 110

Gly Gly Phe Gly Leu Gly Gly Gly Ala Gly Phe Gly Gly Gly Phe Gly
                 115                 120                 125

Gly Pro Gly Phe Pro Val Cys Pro Pro Gly Gly Ile Gln Glu Val Thr
                 130                 135                 140

Val Asn Gln Ser Leu Leu Thr Pro Leu Asn Leu Gln Ile Asp Pro Ser
145                 150                 155                 160

Ile Gln Arg Val Arg Thr Glu Glu Arg Glu Gln Ile Lys Thr Leu Asn
                 165                 170                 175

Asn Lys Phe Ala Ser Phe Ile Asp Lys Val Arg Phe Leu Glu Gln Gln
                 180                 185                 190

Asn Lys Val Leu Asp Thr Lys Trp Thr Leu Leu Gln Glu Gln Gly Thr
                 195                 200                 205

Lys Thr Val Arg Gln Asn Leu Glu Pro Leu Phe Glu Gln Tyr Ile Asn
                 210                 215                 220

Asn Leu Arg Arg Gln Leu Asp Ser Ile Val Gly Glu Arg Gly Arg Leu
225                 230                 235                 240

Asp Ser Glu Leu Arg Asn Met Gln Asp Leu Val Glu Asp Phe Lys Asn
                 245                 250                 255

Lys Tyr Glu Asp Glu Ile Asn Lys Arg Thr Thr Ala Glu Asn Glu Phe
                 260                 265                 270

Val Met Leu Lys Lys Asp Val Asp Ala Ala Tyr Met Asn Lys Val Glu
                 275                 280                 285

Leu Glu Ala Lys Val Asp Ala Leu Met Asp Glu Ile Asn Phe Met Lys
                 290                 295                 300

Met Phe Phe Asp Ala Glu Leu Ser Gln Met Gln Thr His Val Ser Asp
305                 310                 315                 320

Thr Ser Val Val Leu Ser Met Asp Asn Asn Arg Asn Leu Asp Leu Asp
                 325                 330                 335

Ser Ile Ile Ala Glu Val Lys Ala Gln Tyr Glu Glu Ile Ala Asn Arg
                 340                 345                 350

Ser Arg Thr Glu Ala Glu Ser Trp Tyr Gln Thr Lys Tyr Glu Glu Leu
                 355                 360                 365

Gln Gln Thr Ala Gly Arg His Gly Asp Asp Leu Arg Asn Thr Lys His
                 370                 375                 380

Glu Ile Thr Glu Met Asn Arg Met Ile Gln Arg Leu Arg Ala Glu Ile
385                 390                 395                 400

Asp Asn Val Lys Lys Gln Cys Ala Asn Leu Gln Asn Ala Ile Ala Asp
                 405                 410                 415

Ala Glu Gln Arg Gly Glu Leu Ala Leu Lys Asp Ala Arg Asn Lys Leu
                 420                 425                 430

Ala Glu Leu Glu Glu Ala Leu Gln Lys Ala Lys Gln Asp Met Ala Arg
                 435                 440                 445

Leu Leu Arg Glu Tyr Gln Glu Leu Met Asn Thr Lys Leu Ala Leu Asp

```
            450                 455                 460
Val Glu Ile Ala Thr Tyr Arg Lys Leu Leu Glu Gly Glu Cys Arg
465                 470                 475                 480

Leu Ser Gly Glu Gly Val Gly Pro Val Asn Ile Ser Val Val Thr Ser
                485                 490                 495

Ser Val Ser Ser Gly Tyr Gly Ser Ser Gly Tyr Gly Gly Leu
            500                 505                 510

Gly Gly Gly Leu Gly Gly Gly Leu Gly Gly Leu Ala Gly Gly Ser
            515                 520                 525

Ser Gly Ser Tyr Tyr Ser Ser Ser Gly Gly Val Gly Leu Gly Gly
            530                 535                 540

Gly Leu Ser Val Gly Gly Ser Gly Phe Ser Ala Ser Ser Gly Arg Gly
545                 550                 555                 560

Leu Gly Val Gly Phe Gly Ser Gly Gly Ser Ser Ser Ser Val Lys
                565                 570                 575

Phe Val Ser Thr Thr Ser Ser Ser Arg Lys Ser Phe Lys Ser
                580                 585                 590

<210> SEQ ID NO 3
<211> LENGTH: 472
<212> TYPE: PRT
<213> ORGANISM: Homo sapiens

<400> SEQUENCE: 3

Met Thr Thr Cys Ser Arg Gln Phe Thr Ser Ser Ser Met Lys Gly
1               5                   10                  15

Ser Cys Gly Ile Gly Gly Gly Ile Gly Gly Ser Ser Arg Ile Ser
            20                  25                  30

Ser Val Leu Ala Gly Gly Ser Cys Arg Ala Pro Ser Thr Tyr Gly Gly
            35                  40                  45

Gly Leu Ser Val Ser Ser Ser Arg Phe Ser Ser Gly Gly Ala Tyr Gly
            50                  55                  60

Leu Gly Gly Gly Tyr Gly Gly Gly Phe Ser Ser Ser Ser Ser Ser Phe
65                  70                  75                  80

Gly Ser Gly Phe Gly Gly Gly Tyr Gly Gly Gly Leu Gly Thr Gly Leu
                85                  90                  95

Gly Gly Gly Phe Gly Gly Gly Phe Ala Gly Gly Asp Gly Leu Leu Val
                100                 105                 110

Gly Ser Glu Lys Val Thr Met Gln Asn Leu Asn Asp Arg Leu Ala Ser
            115                 120                 125

Tyr Leu Asp Lys Val Arg Ala Leu Glu Glu Ala Asn Ala Asp Leu Glu
            130                 135                 140

Val Lys Ile Arg Asp Trp Tyr Gln Arg Gln Arg Pro Ala Glu Ile Lys
145                 150                 155                 160

Asp Tyr Ser Pro Tyr Phe Lys Thr Ile Glu Asp Leu Arg Asn Lys Ile
                165                 170                 175

Leu Thr Ala Thr Val Asp Asn Ala Asn Val Leu Leu Gln Ile Asp Asn
                180                 185                 190

Ala Arg Leu Ala Ala Asp Asp Phe Arg Thr Lys Tyr Glu Thr Glu Leu
            195                 200                 205

Asn Leu Arg Met Ser Val Glu Ala Asp Ile Asn Gly Leu Arg Arg Val
            210                 215                 220

Leu Asp Glu Leu Thr Leu Ala Arg Ala Asp Leu Glu Met Gln Ile Glu
225                 230                 235                 240
```

```
Ser Leu Lys Glu Glu Leu Ala Tyr Leu Lys Asn His Glu Glu
            245                 250                 255

Met Asn Ala Leu Arg Gly Gln Val Gly Gly Asp Val Asn Val Glu Met
                260                 265                 270

Asp Ala Ala Pro Gly Val Asp Leu Ser Arg Ile Leu Asn Glu Met Arg
            275                 280                 285

Asp Gln Tyr Glu Lys Met Ala Glu Lys Asn Arg Lys Asp Ala Glu Glu
            290                 295                 300

Trp Phe Phe Thr Lys Thr Glu Leu Asn Arg Glu Val Ala Thr Asn
305                 310                 315                 320

Ser Glu Leu Val Gln Ser Gly Lys Ser Glu Ile Ser Glu Leu Arg Arg
                325                 330                 335

Thr Met Gln Asn Leu Glu Ile Glu Leu Gln Ser Gln Leu Ser Met Lys
                340                 345                 350

Ala Ser Leu Glu Asn Ser Leu Glu Glu Thr Lys Gly Arg Tyr Cys Met
                355                 360                 365

Gln Leu Ala Gln Ile Gln Glu Met Ile Gly Ser Val Glu Glu Gln Leu
            370                 375                 380

Ala Gln Leu Arg Cys Glu Met Glu Gln Gln Asn Gln Glu Tyr Lys Ile
385                 390                 395                 400

Leu Leu Asp Val Lys Thr Arg Leu Glu Gln Glu Ile Ala Thr Tyr Arg
                405                 410                 415

Arg Leu Leu Glu Gly Glu Asp Ala His Leu Ser Ser Ser Gln Phe Ser
                420                 425                 430

Ser Gly Ser Gln Ser Ser Arg Asp Val Thr Ser Ser Ser Arg Gln Ile
                435                 440                 445

Arg Thr Lys Val Met Asp Val His Asp Gly Lys Val Val Ser Thr His
            450                 455                 460

Glu Gln Val Leu Arg Thr Lys Asn
465                 470

<210> SEQ ID NO 4
<211> LENGTH: 644
<212> TYPE: PRT
<213> ORGANISM: Homo sapiens

<400> SEQUENCE: 4

Met Phe Ser Met Arg Ile Val Cys Leu Val Leu Ser Val Val Gly Thr
1               5                   10                  15

Ala Trp Thr Ala Asp Ser Gly Glu Gly Asp Phe Leu Ala Glu Gly Gly
                20                  25                  30

Gly Val Arg Gly Pro Arg Val Val Glu Arg His Gln Ser Ala Cys Lys
            35                  40                  45

Asp Ser Asp Trp Pro Phe Cys Ser Asp Glu Asp Trp Asn Tyr Lys Cys
        50                  55                  60

Pro Ser Gly Cys Arg Met Lys Gly Leu Ile Asp Glu Val Asn Gln Asp
65                  70                  75                  80

Phe Thr Asn Arg Ile Asn Lys Leu Lys Asn Ser Leu Phe Glu Tyr Gln
                85                  90                  95

Lys Asn Asn Lys Asp Ser His Ser Leu Thr Thr Asn Ile Met Glu Ile
                100                 105                 110

Leu Arg Gly Asp Phe Ser Ser Ala Asn Asn Arg Asp Asn Thr Tyr Asn
            115                 120                 125

Arg Val Ser Glu Asp Leu Arg Ser Arg Ile Glu Val Leu Lys Arg Lys
        130                 135                 140
```

```
Val Ile Glu Lys Val Gln His Ile Gln Leu Leu Gln Lys Asn Val Arg
145                 150                 155                 160

Ala Gln Leu Val Asp Met Lys Arg Leu Glu Val Asp Ile Asp Ile Lys
                165                 170                 175

Ile Arg Ser Cys Arg Gly Ser Cys Ser Arg Ala Leu Ala Arg Glu Val
            180                 185                 190

Asp Leu Lys Asp Tyr Glu Asp Gln Gln Lys Gln Leu Glu Gln Val Ile
            195                 200                 205

Ala Lys Asp Leu Leu Pro Ser Arg Asp Arg Gln His Leu Pro Leu Ile
210                 215                 220

Lys Met Lys Pro Val Pro Asp Leu Val Pro Gly Asn Phe Lys Ser Gln
225                 230                 235                 240

Leu Gln Lys Val Pro Pro Glu Trp Lys Ala Leu Thr Asp Met Pro Gln
                245                 250                 255

Met Arg Met Glu Leu Glu Arg Pro Gly Gly Asn Glu Ile Thr Arg Gly
            260                 265                 270

Gly Ser Thr Ser Tyr Gly Thr Gly Ser Glu Thr Glu Ser Pro Arg Asn
            275                 280                 285

Pro Ser Ser Ala Gly Ser Trp Asn Ser Gly Ser Ser Gly Pro Gly Ser
290                 295                 300

Thr Gly Asn Arg Asn Pro Gly Ser Ser Gly Thr Gly Gly Thr Ala Thr
305                 310                 315                 320

Trp Lys Pro Gly Ser Ser Gly Pro Gly Ser Thr Gly Ser Trp Asn Ser
                325                 330                 335

Gly Ser Ser Gly Thr Gly Ser Thr Gly Asn Gln Asn Pro Gly Ser Pro
            340                 345                 350

Arg Pro Gly Ser Thr Gly Thr Trp Asn Pro Gly Ser Ser Glu Arg Gly
            355                 360                 365

Ser Ala Gly His Trp Thr Ser Glu Ser Ser Val Ser Gly Ser Thr Gly
370                 375                 380

Gln Trp His Ser Glu Ser Gly Ser Phe Arg Pro Asp Ser Pro Gly Ser
385                 390                 395                 400

Gly Asn Ala Arg Pro Asn Asn Pro Asp Trp Gly Thr Phe Glu Glu Val
                405                 410                 415

Ser Gly Asn Val Ser Pro Gly Thr Arg Arg Glu Tyr His Thr Glu Lys
            420                 425                 430

Leu Val Thr Ser Lys Gly Asp Lys Glu Leu Arg Thr Gly Lys Glu Lys
            435                 440                 445

Val Thr Ser Gly Ser Thr Thr Thr Thr Arg Arg Ser Cys Ser Lys Thr
            450                 455                 460

Val Thr Lys Thr Val Ile Gly Pro Asp Gly His Lys Glu Val Thr Lys
465                 470                 475                 480

Glu Val Val Thr Ser Glu Asp Gly Ser Asp Cys Pro Glu Ala Met Asp
                485                 490                 495

Leu Gly Thr Leu Ser Gly Ile Gly Thr Leu Asp Gly Phe Arg His Arg
            500                 505                 510

His Pro Asp Glu Ala Ala Phe Phe Asp Thr Ala Ser Thr Gly Lys Thr
            515                 520                 525

Phe Pro Gly Phe Phe Ser Pro Met Leu Gly Glu Phe Val Ser Glu Thr
530                 535                 540

Glu Ser Arg Gly Ser Glu Ser Gly Ile Phe Thr Asn Thr Lys Glu Ser
545                 550                 555                 560
```

```
Ser Ser His His Pro Gly Ile Ala Glu Phe Pro Arg Gly Lys Ser
            565                 570                 575

Ser Ser Tyr Ser Lys Gln Phe Thr Ser Ser Thr Ser Tyr Asn Arg Gly
            580                 585                 590

Asp Ser Thr Phe Glu Ser Lys Ser Tyr Lys Met Ala Asp Glu Ala Gly
            595                 600                 605

Ser Glu Ala Asp His Glu Gly Thr His Ser Thr Lys Arg Gly His Ala
            610                 615                 620

Lys Ser Arg Pro Val Arg Gly Ile His Thr Ser Pro Leu Gly Lys Pro
625                 630                 635                 640

Ser Leu Ser Pro

<210> SEQ ID NO 5
<211> LENGTH: 491
<212> TYPE: PRT
<213> ORGANISM: Homo sapiens

<400> SEQUENCE: 5

Met Lys Arg Met Val Ser Trp Ser Phe His Lys Leu Lys Thr Met Lys
1               5                   10                  15

His Leu Leu Leu Leu Leu Cys Val Phe Leu Val Lys Ser Gln Gly
            20                  25                  30

Val Asn Asp Asn Glu Glu Gly Phe Phe Ser Ala Arg Gly His Arg Pro
            35                  40                  45

Leu Asp Lys Lys Arg Glu Glu Ala Pro Ser Leu Arg Pro Ala Pro Pro
            50                  55                  60

Pro Ile Ser Gly Gly Gly Tyr Arg Ala Arg Pro Ala Lys Ala Ala Ala
65              70                  75                  80

Thr Gln Lys Lys Val Glu Arg Lys Ala Pro Asp Ala Gly Gly Cys Leu
            85                  90                  95

His Ala Asp Pro Asp Leu Gly Val Leu Cys Pro Thr Gly Cys Gln Leu
            100                 105                 110

Gln Glu Ala Leu Leu Gln Gln Glu Arg Pro Ile Arg Asn Ser Val Asp
            115                 120                 125

Glu Leu Asn Asn Asn Val Glu Ala Val Ser Gln Thr Ser Ser Ser Ser
            130                 135                 140

Phe Gln Tyr Met Tyr Leu Leu Lys Asp Leu Trp Gln Lys Arg Gln Lys
145                 150                 155                 160

Gln Val Lys Asp Asn Glu Asn Val Val Asn Glu Tyr Ser Ser Glu Leu
            165                 170                 175

Glu Lys His Gln Leu Tyr Ile Asp Glu Thr Val Asn Ser Asn Ile Pro
            180                 185                 190

Thr Asn Leu Arg Val Leu Arg Ser Ile Leu Glu Asn Leu Arg Ser Lys
            195                 200                 205

Ile Gln Lys Leu Glu Ser Asp Val Ser Ala Gln Met Glu Tyr Cys Arg
            210                 215                 220

Thr Pro Cys Thr Val Ser Cys Asn Ile Pro Val Val Ser Gly Lys Glu
225                 230                 235                 240

Cys Glu Glu Ile Ile Arg Lys Gly Gly Glu Thr Ser Glu Met Tyr Leu
            245                 250                 255

Ile Gln Pro Asp Ser Ser Val Lys Pro Tyr Arg Val Tyr Cys Asp Met
            260                 265                 270

Asn Thr Glu Asn Gly Gly Trp Thr Val Ile Gln Asn Arg Gln Asp Gly
            275                 280                 285
```

```
Ser Val Asp Phe Gly Arg Lys Trp Asp Pro Tyr Lys Gln Gly Phe Gly
    290                 295                 300
Asn Val Ala Thr Asn Thr Asp Gly Lys Asn Tyr Cys Gly Leu Pro Gly
305                 310                 315                 320
Glu Tyr Trp Leu Gly Asn Asp Lys Ile Ser Gln Leu Thr Arg Met Gly
                325                 330                 335
Pro Thr Glu Leu Leu Ile Glu Met Glu Asp Trp Lys Gly Asp Lys Val
                340                 345                 350
Lys Ala His Tyr Gly Gly Phe Thr Val Gln Asn Glu Ala Asn Lys Tyr
                355                 360                 365
Gln Ile Ser Val Asn Lys Tyr Arg Gly Thr Ala Gly Asn Ala Leu Met
370                 375                 380
Asp Gly Ala Ser Gln Leu Met Gly Glu Asn Arg Thr Met Thr Ile His
385                 390                 395                 400
Asn Gly Met Phe Phe Ser Thr Tyr Asp Arg Asp Asn Asp Gly Trp Leu
                405                 410                 415
Thr Ser Asp Pro Arg Lys Gln Cys Ser Lys Glu Asp Gly Gly Gly Trp
                420                 425                 430
Trp Tyr Asn Arg Cys His Ala Ala Asn Pro Asn Gly Arg Tyr Tyr Trp
                435                 440                 445
Gly Gly Gln Tyr Thr Trp Asp Met Ala Lys His Gly Thr Asp Asp Gly
450                 455                 460
Val Val Trp Met Asn Trp Lys Gly Ser Trp Tyr Ser Met Arg Lys Met
465                 470                 475                 480
Ser Met Lys Ile Arg Pro Phe Phe Pro Gln Gln
                485                 490

<210> SEQ ID NO 6
<211> LENGTH: 437
<212> TYPE: PRT
<213> ORGANISM: Homo sapiens

<400> SEQUENCE: 6

Met Ser Trp Ser Leu His Pro Arg Asn Leu Ile Leu Tyr Phe Tyr Ala
1               5                   10                  15
Leu Leu Phe Leu Ser Ser Thr Cys Val Ala Tyr Val Ala Thr Arg Asp
                20                  25                  30
Asn Cys Cys Ile Leu Asp Glu Arg Phe Gly Ser Tyr Cys Pro Thr Thr
            35                  40                  45
Cys Gly Ile Ala Asp Phe Leu Ser Thr Tyr Gln Thr Lys Val Asp Lys
    50                  55                  60
Asp Leu Gln Ser Leu Glu Asp Ile Leu His Gln Val Glu Asn Lys Thr
65                  70                  75                  80
Ser Glu Val Lys Gln Leu Ile Lys Ala Ile Gln Leu Thr Tyr Asn Pro
                85                  90                  95
Asp Glu Ser Ser Lys Pro Asn Met Ile Asp Ala Ala Thr Leu Lys Ser
                100                 105                 110
Arg Ile Met Leu Glu Glu Ile Met Lys Tyr Glu Ala Ser Ile Leu Thr
            115                 120                 125
His Asp Ser Ser Ile Arg Tyr Leu Gln Glu Ile Tyr Asn Ser Asn Asn
    130                 135                 140
Gln Lys Ile Val Asn Leu Lys Glu Lys Val Ala Gln Leu Glu Ala Gln
145                 150                 155                 160
Cys Gln Glu Pro Cys Lys Asp Thr Val Gln Ile His Asp Ile Thr Gly
                165                 170                 175
```

Lys Asp Cys Gln Asp Ile Ala Asn Lys Gly Ala Lys Gln Ser Gly Leu
            180                 185                 190

Tyr Phe Ile Lys Pro Leu Lys Ala Asn Gln Gln Phe Leu Val Tyr Cys
            195                 200                 205

Glu Ile Asp Gly Ser Gly Asn Gly Trp Thr Val Phe Gln Lys Arg Leu
            210                 215                 220

Asp Gly Ser Val Asp Phe Lys Lys Asn Trp Ile Gln Tyr Lys Glu Gly
225                 230                 235                 240

Phe Gly His Leu Ser Pro Thr Gly Thr Thr Glu Phe Trp Leu Gly Asn
            245                 250                 255

Glu Lys Ile His Leu Ile Ser Thr Gln Ser Ala Ile Pro Tyr Ala Leu
            260                 265                 270

Arg Val Glu Leu Glu Asp Trp Asn Gly Arg Thr Ser Thr Ala Asp Tyr
            275                 280                 285

Ala Met Phe Lys Val Gly Pro Glu Ala Asp Lys Tyr Arg Leu Thr Tyr
            290                 295                 300

Ala Tyr Phe Ala Gly Gly Asp Ala Gly Asp Ala Phe Asp Gly Phe Asp
305                 310                 315                 320

Phe Gly Asp Asp Pro Ser Asp Lys Phe Phe Thr Ser His Asn Gly Met
            325                 330                 335

Gln Phe Ser Thr Trp Asp Asn Asp Asn Asp Lys Phe Glu Gly Asn Cys
            340                 345                 350

Ala Glu Gln Asp Gly Ser Gly Trp Trp Met Asn Lys Cys His Ala Gly
            355                 360                 365

His Leu Asn Gly Val Tyr Tyr Gln Gly Gly Thr Tyr Ser Lys Ala Ser
            370                 375                 380

Thr Pro Asn Gly Tyr Asp Asn Gly Ile Ile Trp Ala Thr Trp Lys Thr
385                 390                 395                 400

Arg Trp Tyr Ser Met Lys Lys Thr Thr Met Lys Ile Ile Pro Phe Asn
            405                 410                 415

Arg Leu Thr Ile Gly Glu Gly Gln Gln His His Leu Gly Gly Ala Lys
            420                 425                 430

Gln Ala Gly Asp Val
            435

<210> SEQ ID NO 7
<211> LENGTH: 757
<212> TYPE: PRT
<213> ORGANISM: Homo sapiens

<400> SEQUENCE: 7

Met Ala Gly Leu Thr Ala Ala Ala Pro Arg Pro Gly Val Leu Leu Leu
1               5                   10                  15

Leu Leu Ser Ile Leu His Pro Ser Arg Pro Gly Gly Val Pro Gly Ala
            20                  25                  30

Ile Pro Gly Gly Val Pro Gly Gly Val Phe Tyr Pro Gly Ala Gly Leu
            35                  40                  45

Gly Ala Leu Gly Gly Gly Ala Leu Gly Pro Gly Gly Lys Pro Leu Lys
            50                  55                  60

Pro Val Pro Gly Gly Leu Ala Gly Ala Gly Leu Gly Ala Gly Leu Gly
65                  70                  75                  80

Ala Phe Pro Ala Val Thr Phe Pro Gly Ala Leu Val Pro Gly Gly Val
            85                  90                  95

Ala Asp Ala Ala Ala Ala Tyr Lys Ala Ala Lys Ala Gly Ala Gly Leu

```
                100             105                 110
        Gly Gly Val Pro Gly Val Gly Leu Gly Val Ser Ala Gly Ala Val
                    115                 120                 125

Val Pro Gln Pro Gly Ala Gly Val Lys Pro Gly Lys Val Pro Gly Val
                    130                 135                 140

Gly Leu Pro Gly Val Tyr Pro Gly Gly Val Leu Pro Gly Ala Arg Phe
        145                 150                 155                 160

Pro Gly Val Gly Val Leu Pro Gly Val Pro Thr Gly Ala Gly Val Lys
                            165                 170                 175

Pro Lys Ala Pro Gly Val Gly Gly Ala Phe Ala Gly Ile Pro Gly Val
                    180                 185                 190

Gly Pro Phe Gly Gly Pro Gln Pro Gly Val Pro Leu Gly Tyr Pro Ile
                    195                 200                 205

Lys Ala Pro Lys Leu Pro Gly Gly Tyr Gly Leu Pro Tyr Thr Thr Gly
                    210                 215                 220

Lys Leu Pro Tyr Gly Tyr Gly Pro Gly Gly Val Ala Gly Ala Ala Gly
        225                 230                 235                 240

Lys Ala Gly Tyr Pro Thr Gly Thr Gly Val Gly Pro Gln Ala Ala Ala
                            245                 250                 255

Ala Ala Ala Ala Lys Ala Ala Ala Lys Phe Gly Ala Gly Ala Ala Gly
                    260                 265                 270

Val Leu Pro Gly Val Gly Gly Ala Gly Val Pro Gly Val Pro Gly Ala
                    275                 280                 285

Ile Pro Gly Ile Gly Gly Ile Ala Gly Val Gly Thr Pro Ala Ala Ala
                    290                 295                 300

Ala Ala Ala Ala Ala Ala Ala Lys Ala Ala Lys Tyr Gly Ala Ala Ala
        305                 310                 315                 320

Gly Leu Val Pro Gly Gly Pro Gly Phe Gly Pro Gly Val Val Gly Val
                            325                 330                 335

Pro Gly Ala Gly Val Pro Gly Val Gly Val Pro Gly Ala Gly Ile Pro
                    340                 345                 350

Val Val Pro Gly Ala Gly Ile Pro Gly Ala Ala Val Pro Gly Val Val
                    355                 360                 365

Ser Pro Glu Ala Ala Ala Lys Ala Ala Ala Lys Ala Ala Lys Tyr Gly
                    370                 375                 380

Ala Arg Pro Gly Val Gly Val Gly Gly Ile Pro Thr Tyr Gly Val Gly
        385                 390                 395                 400

Ala Gly Gly Phe Pro Gly Phe Gly Val Gly Val Gly Gly Ile Pro Gly
                            405                 410                 415

Val Ala Gly Val Pro Ser Val Gly Gly Val Pro Gly Val Gly Gly Val
                    420                 425                 430

Pro Gly Val Gly Ile Ser Pro Glu Ala Gln Ala Ala Ala Ala Ala Lys
                    435                 440                 445

Ala Ala Lys Tyr Gly Val Gly Thr Pro Ala Ala Ala Ala Ala Lys Ala
        450                 455                 460

Ala Ala Lys Ala Ala Gln Phe Gly Leu Val Pro Gly Val Gly Val Ala
        465                 470                 475                 480

Pro Gly Val Gly Val Ala Pro Gly Val Gly Val Ala Pro Gly Val Gly
                            485                 490                 495

Leu Ala Pro Gly Val Gly Val Ala Pro Gly Val Gly Val Ala Pro Gly
                    500                 505                 510

Val Gly Val Ala Pro Gly Ile Gly Pro Gly Gly Val Ala Ala Ala Ala
                    515                 520                 525
```

```
Lys Ser Ala Ala Lys Val Ala Lys Ala Gln Leu Arg Ala Ala
    530                 535                 540

Gly Leu Gly Ala Gly Ile Pro Gly Leu Gly Val Gly Val Gly Val Pro
545                 550                 555                 560

Gly Leu Gly Val Gly Ala Gly Val Pro Gly Leu Gly Val Gly Ala Gly
                565                 570                 575

Val Pro Gly Phe Gly Ala Gly Ala Asp Glu Gly Val Arg Arg Ser Leu
            580                 585                 590

Ser Pro Glu Leu Arg Glu Gly Asp Pro Ser Ser Gln His Leu Pro
        595                 600                 605

Ser Thr Pro Ser Ser Pro Arg Val Pro Gly Ala Leu Ala Ala Ala Lys
        610                 615                 620

Ala Ala Lys Tyr Gly Ala Ala Val Pro Gly Val Leu Gly Gly Leu Gly
625                 630                 635                 640

Ala Leu Gly Gly Val Gly Ile Pro Gly Gly Val Val Gly Ala Gly Pro
                645                 650                 655

Ala Ala Ala Ala Ala Ala Ala Lys Ala Ala Lys Ala Ala Gln Phe
            660                 665                 670

Gly Leu Val Gly Ala Ala Gly Leu Gly Gly Leu Gly Val Gly Gly Leu
        675                 680                 685

Gly Val Pro Gly Val Gly Gly Leu Gly Gly Ile Pro Pro Ala Ala Ala
690                 695                 700

Ala Lys Ala Ala Lys Tyr Gly Ala Ala Gly Leu Gly Gly Val Leu Gly
705                 710                 715                 720

Gly Ala Gly Gln Phe Pro Leu Gly Gly Val Ala Ala Arg Pro Gly Phe
                725                 730                 735

Gly Leu Ser Pro Ile Phe Pro Gly Gly Ala Cys Leu Gly Lys Ala Cys
            740                 745                 750

Gly Arg Lys Arg Lys
        755

<210> SEQ ID NO 8
<211> LENGTH: 1678
<212> TYPE: PRT
<213> ORGANISM: Homo sapiens

<400> SEQUENCE: 8

Met His Pro Gly Leu Trp Leu Leu Leu Val Thr Leu Cys Leu Thr Glu
1               5                   10                  15

Glu Leu Ala Ala Gly Glu Lys Ser Tyr Gly Lys Pro Cys Gly Gly
            20                  25                  30

Gln Asp Cys Ser Gly Ser Cys Gln Cys Phe Pro Glu Lys Gly Ala Arg
        35                  40                  45

Gly Arg Pro Gly Pro Ile Gly Ile Gln Gly Pro Thr Gly Pro Gln Gly
    50                  55                  60

Phe Thr Gly Ser Thr Gly Leu Ser Gly Leu Lys Gly Glu Arg Gly Phe
65              70                  75                  80

Pro Gly Leu Leu Gly Pro Tyr Gly Pro Lys Gly Asp Lys Gly Pro Met
                85                  90                  95

Gly Val Pro Gly Phe Leu Gly Ile Asn Gly Ile Pro Gly His Pro Gly
            100                 105                 110

Gln Pro Gly Pro Arg Gly Pro Pro Gly Leu Asp Gly Cys Asn Gly Thr
        115                 120                 125

Gln Gly Ala Val Gly Phe Pro Gly Pro Asp Gly Tyr Pro Gly Leu Leu
```

```
            130                 135                 140
Gly Pro Pro Gly Leu Pro Gly Gln Lys Gly Ser Lys Gly Asp Pro Val
145                 150                 155                 160

Leu Ala Pro Gly Ser Phe Lys Gly Met Lys Gly Asp Pro Gly Leu Pro
                165                 170                 175

Gly Leu Asp Gly Ile Thr Gly Pro Gln Gly Ala Pro Gly Phe Pro Gly
            180                 185                 190

Ala Val Gly Pro Ala Gly Pro Pro Gly Leu Gln Gly Pro Pro Gly Pro
            195                 200                 205

Pro Gly Pro Leu Gly Pro Asp Gly Asn Met Gly Leu Gly Phe Gln Gly
210                 215                 220

Glu Lys Gly Val Lys Gly Asp Val Gly Leu Pro Gly Pro Ala Gly Pro
225                 230                 235                 240

Pro Pro Ser Thr Gly Glu Leu Glu Phe Met Gly Phe Pro Lys Gly Lys
                245                 250                 255

Lys Gly Ser Lys Gly Glu Pro Gly Pro Lys Gly Phe Pro Gly Ile Ser
                260                 265                 270

Gly Pro Pro Gly Phe Pro Gly Leu Gly Thr Thr Gly Glu Lys Gly Glu
            275                 280                 285

Lys Gly Glu Lys Gly Ile Pro Gly Leu Pro Gly Pro Arg Gly Pro Met
290                 295                 300

Gly Ser Glu Gly Val Gln Gly Pro Pro Gly Gln Gln Gly Lys Lys Gly
305                 310                 315                 320

Thr Leu Gly Phe Pro Gly Leu Asn Gly Phe Gln Gly Ile Glu Gly Gln
                325                 330                 335

Lys Gly Asp Ile Gly Leu Pro Gly Pro Asp Val Phe Ile Asp Ile Asp
                340                 345                 350

Gly Ala Val Ile Ser Gly Asn Pro Gly Asp Pro Gly Val Pro Gly Leu
                355                 360                 365

Pro Gly Leu Lys Gly Asp Glu Gly Ile Gln Gly Leu Arg Gly Pro Ser
            370                 375                 380

Gly Val Pro Gly Leu Pro Ala Leu Ser Gly Val Pro Gly Ala Leu Gly
385                 390                 395                 400

Pro Gln Gly Phe Pro Gly Leu Lys Gly Asp Gln Gly Asn Pro Gly Arg
                405                 410                 415

Thr Thr Ile Gly Ala Ala Gly Leu Pro Gly Arg Asp Gly Leu Pro Gly
            420                 425                 430

Pro Pro Gly Pro Pro Gly Pro Pro Ser Pro Glu Phe Glu Thr Glu Thr
            435                 440                 445

Leu His Asn Lys Glu Ser Gly Phe Pro Gly Leu Arg Gly Glu Gln Gly
450                 455                 460

Pro Lys Gly Asn Leu Gly Leu Lys Gly Ile Lys Gly Asp Ser Gly Phe
465                 470                 475                 480

Cys Ala Cys Asp Gly Gly Val Pro Asn Thr Gly Pro Pro Gly Glu Pro
                485                 490                 495

Gly Pro Pro Gly Pro Trp Gly Leu Ile Gly Leu Pro Gly Leu Lys Gly
            500                 505                 510

Ala Arg Gly Asp Arg Gly Ser Gly Gly Ala Gln Gly Pro Ala Gly Ala
            515                 520                 525

Pro Gly Leu Val Gly Pro Leu Gly Pro Ser Gly Pro Lys Gly Lys Lys
            530                 535                 540

Gly Glu Pro Ile Leu Ser Thr Ile Gln Gly Met Pro Gly Asp Arg Gly
545                 550                 555                 560
```

-continued

```
Asp Ser Gly Ser Gln Gly Phe Arg Gly Val Ile Gly Glu Pro Gly Lys
            565                 570                 575
Asp Gly Val Pro Gly Leu Pro Gly Leu Pro Gly Leu Pro Gly Asp Gly
        580                 585                 590
Gly Gln Gly Phe Pro Gly Glu Lys Gly Leu Pro Gly Leu Pro Gly Glu
    595                 600                 605
Lys Gly His Pro Gly Pro Pro Gly Leu Pro Gly Asn Gly Leu Pro Gly
610                 615                 620
Leu Pro Gly Pro Arg Gly Leu Pro Gly Asp Lys Gly Lys Asp Gly Leu
625                 630                 635                 640
Pro Gly Gln Gln Gly Leu Pro Gly Ser Lys Gly Ile Thr Leu Pro Cys
            645                 650                 655
Ile Ile Pro Gly Ser Tyr Gly Pro Ser Gly Phe Pro Gly Thr Pro Gly
        660                 665                 670
Phe Pro Gly Pro Lys Gly Ser Arg Gly Leu Pro Gly Thr Pro Gly Gln
    675                 680                 685
Pro Gly Ser Ser Gly Ser Lys Gly Glu Pro Gly Ser Pro Gly Leu Val
690                 695                 700
His Leu Pro Glu Leu Pro Gly Phe Pro Gly Pro Arg Gly Glu Lys Gly
705                 710                 715                 720
Leu Pro Gly Phe Pro Gly Leu Pro Gly Lys Asp Gly Leu Pro Gly Met
            725                 730                 735
Ile Gly Ser Pro Gly Leu Pro Gly Ser Lys Gly Ala Thr Gly Asp Ile
        740                 745                 750
Phe Gly Ala Glu Asn Gly Ala Pro Gly Glu Gln Gly Leu Gln Gly Leu
    755                 760                 765
Thr Gly His Lys Gly Phe Leu Gly Asp Ser Gly Leu Pro Gly Leu Lys
770                 775                 780
Gly Val His Gly Lys Pro Gly Leu Leu Gly Pro Lys Gly Glu Arg Gly
785                 790                 795                 800
Ser Pro Gly Thr Pro Gly Gln Val Gly Gln Pro Gly Thr Pro Gly Ser
            805                 810                 815
Ser Gly Pro Tyr Gly Ile Lys Gly Lys Ser Gly Leu Pro Gly Ala Pro
        820                 825                 830
Gly Phe Pro Gly Ile Ser Gly His Pro Gly Lys Lys Gly Thr Arg Gly
    835                 840                 845
Lys Lys Gly Pro Pro Gly Ser Ile Val Lys Lys Gly Leu Pro Gly Leu
850                 855                 860
Lys Gly Leu Pro Gly Asn Pro Gly Leu Val Gly Leu Lys Gly Ser Pro
865                 870                 875                 880
Gly Ser Pro Gly Val Ala Gly Leu Pro Ala Leu Ser Gly Pro Lys Gly
            885                 890                 895
Glu Lys Gly Ser Val Gly Phe Val Gly Phe Pro Gly Ile Pro Gly Leu
        900                 905                 910
Pro Gly Ile Ser Gly Thr Arg Gly Leu Lys Gly Ile Pro Gly Ser Thr
    915                 920                 925
Gly Lys Met Gly Pro Ser Gly Arg Ala Gly Thr Pro Gly Glu Lys Gly
930                 935                 940
Asp Arg Gly Asn Pro Gly Pro Val Gly Ile Pro Ser Pro Arg Arg Pro
945                 950                 955                 960
Met Ser Asn Leu Trp Leu Lys Gly Asp Lys Gly Ser Gln Gly Ser Ala
            965                 970                 975
```

```
Gly Ser Asn Gly Phe Pro Gly Pro Arg Gly Asp Lys Gly Glu Ala Gly
            980                 985                 990

Arg Pro Gly Pro Pro Gly Leu Pro  Gly Ala Pro Gly Leu  Pro Gly Ile
        995                 1000                1005

Ile Lys Gly Val Ser Gly Lys Pro Gly Pro Pro Gly  Phe Met Gly
        1010                1015                1020

Ile Arg Gly Leu Pro Gly Leu  Lys Gly Ser Ser  Gly Ile Thr Gly
        1025                1030                1035

Phe Pro Gly Met Pro Gly Glu  Ser Gly Ser Gln  Gly Ile Arg Gly
        1040                1045                1050

Ser Pro Gly Leu Pro Gly Ala  Ser Gly Leu Pro  Gly Leu Lys Gly
        1055                1060                1065

Asp Asn Gly Gln Thr Val Glu  Ile Ser Gly Ser  Gly Pro Lys
        1070                1075                1080

Gly Gln Pro Gly Glu Ser Gly  Phe Lys Gly Thr Lys  Gly Arg Asp
        1085                1090                1095

Gly Leu Ile Gly Asn Ile Gly  Phe Pro Gly Asn Lys  Gly Glu Asp
        1100                1105                1110

Gly Lys Val Gly Val Ser Gly  Asp Val Gly Leu Pro  Gly Ala Pro
        1115                1120                1125

Gly Phe Pro Gly Val Ala Gly  Met Arg Gly Glu Pro  Gly Leu Pro
        1130                1135                1140

Gly Ser Ser Gly His Gln Gly  Ala Ile Gly Pro Leu  Gly Ser Pro
        1145                1150                1155

Gly Leu Ile Gly Pro Lys Gly  Phe Pro Gly Phe Pro  Gly Leu His
        1160                1165                1170

Gly Leu Asn Gly Leu Pro Gly  Thr Lys Gly Thr His  Gly Thr Pro
        1175                1180                1185

Gly Pro Ser Ile Thr Gly Val  Pro Gly Pro Ala Gly  Leu Pro Gly
        1190                1195                1200

Pro Lys Gly Glu Lys Gly Tyr  Pro Gly Ile Gly Ile  Gly Ala Pro
        1205                1210                1215

Gly Lys Pro Gly Leu Arg Gly  Gln Lys Gly Asp Arg  Gly Phe Pro
        1220                1225                1230

Gly Leu Gln Gly Pro Ala Gly  Leu Pro Gly Ala Pro  Gly Ile Ser
        1235                1240                1245

Leu Pro Ser Leu Ile Ala Gly  Gln Pro Gly Asp Pro  Gly Arg Pro
        1250                1255                1260

Gly Leu Asp Gly Glu Arg Gly  Arg Pro Gly Pro Ala  Gly Pro Pro
        1265                1270                1275

Gly Pro Pro Gly Pro Ser Ser  Asn Gln Gly Asp Thr  Gly Asp Pro
        1280                1285                1290

Gly Phe Pro Gly Ile Pro Gly  Phe Ser Gly Leu Pro  Gly Glu Leu
        1295                1300                1305

Gly Leu Lys Gly Met Arg Gly  Glu Pro Gly Phe Met  Gly Thr Pro
        1310                1315                1320

Gly Lys Val Gly Pro Pro Gly  Asp Pro Gly Phe Pro  Gly Met Lys
        1325                1330                1335

Gly Lys Ala Gly Ala Arg Gly  Ser Ser Gly Leu Gln  Gly Asp Pro
        1340                1345                1350

Gly Gln Thr Pro Thr Ala Glu  Ala Val Gln Val Pro  Pro Gly Pro
        1355                1360                1365

Leu Gly Leu Pro Gly Ile Asp  Gly Ile Pro Gly Leu  Thr Gly Asp
```

```
                1370                1375                1380

Pro Gly Ala Gln Gly Pro Val Gly Leu Gln Gly Ser Lys Gly Leu
    1385                1390                1395

Pro Gly Ile Pro Gly Lys Asp Gly Pro Ser Gly Leu Pro Gly Pro
    1400                1405                1410

Pro Gly Ala Leu Gly Asp Pro Gly Leu Pro Gly Leu Gln Gly Pro
    1415                1420                1425

Pro Gly Phe Glu Gly Ala Pro Gly Gln Gln Gly Pro Phe Gly Met
    1430                1435                1440

Pro Gly Met Pro Gly Gln Ser Met Arg Val Gly Tyr Thr Leu Val
    1445                1450                1455

Lys His Ser Gln Ser Glu Gln Val Pro Pro Cys Pro Ile Gly Met
    1460                1465                1470

Ser Gln Leu Trp Val Gly Tyr Ser Leu Leu Phe Val Glu Gly Gln
    1475                1480                1485

Glu Lys Ala His Asn Gln Asp Leu Gly Phe Ala Gly Ser Cys Leu
    1490                1495                1500

Pro Arg Phe Ser Thr Met Pro Phe Ile Tyr Cys Asn Ile Asn Glu
    1505                1510                1515

Val Cys His Tyr Ala Arg Arg Asn Asp Lys Ser Tyr Trp Leu Ser
    1520                1525                1530

Thr Thr Ala Pro Ile Pro Met Met Pro Val Ser Gln Thr Gln Ile
    1535                1540                1545

Pro Gln Tyr Ile Ser Arg Cys Ser Val Cys Glu Ala Pro Ser Gln
    1550                1555                1560

Ala Ile Ala Val His Ser Gln Asp Ile Thr Ile Pro Gln Cys Pro
    1565                1570                1575

Leu Gly Trp Arg Ser Leu Trp Ile Gly Tyr Ser Phe Leu Met His
    1580                1585                1590

Thr Ala Ala Gly Ala Glu Gly Gly Gly Gln Ser Leu Val Ser Pro
    1595                1600                1605

Gly Ser Cys Leu Glu Asp Phe Arg Ala Thr Pro Phe Ile Glu Cys
    1610                1615                1620

Ser Gly Ala Arg Gly Thr Cys His Tyr Phe Ala Asn Lys Tyr Ser
    1625                1630                1635

Phe Trp Leu Thr Thr Val Glu Glu Arg Gln Gln Phe Gly Glu Leu
    1640                1645                1650

Pro Val Ser Glu Thr Leu Lys Ala Gly Gln Leu His Thr Arg Val
    1655                1660                1665

Ser Arg Cys Gln Val Cys Met Lys Ser Leu
    1670                1675

<210> SEQ ID NO 9
<211> LENGTH: 11
<212> TYPE: PRT
<213> ORGANISM: Homo sapiens

<400> SEQUENCE: 9

Gly Pro Arg Val Val Glu Arg His Gln Ser Ala
1               5                   10

<210> SEQ ID NO 10
<211> LENGTH: 224
<212> TYPE: PRT
<213> ORGANISM: Homo sapiens
```

<400> SEQUENCE: 10

```
Asp Ala Gly Asp Ala Phe Asp Gly Phe Asp Phe Gly Asp Asp Pro Ser
1               5                   10                  15

Asp Lys Phe Phe Thr Ser His Asn Gly Met Gln Phe Ser Thr Trp Asp
            20                  25                  30

Asn Asp Asn Asp Lys Phe Glu Gly Asn Cys Ala Glu Gln Asp Gly Ser
        35                  40                  45

Gly Trp Trp Met Asn Lys Cys His Ala Gly His Leu Asn Gly Val Tyr
    50                  55                  60

Tyr Gln Gly Gly Thr Tyr Ser Lys Ala Ser Thr Pro Asn Gly Tyr Asp
65              70                  75                  80

Asn Gly Ile Ile Trp Ala Thr Trp Lys Thr Arg Trp Tyr Ser Met Lys
                85                  90                  95

Lys Thr Thr Met Lys Ile Ile Pro Phe Asn Arg Leu Thr Ile Gly Glu
            100                 105                 110

Gly Gln Gln His His Leu Gly Gly Ala Lys Gln Ala Gly Asp Val Trp
        115                 120                 125

Asp Asn Asp Asn Asp Lys Phe Glu Gly Asn Cys Ala Glu Gln Asp Gly
    130                 135                 140

Ser Gly Trp Trp Met Asn Lys Cys His Ala Gly His Leu Asn Gly Val
145                 150                 155                 160

Tyr Tyr Gln Gly Gly Thr Tyr Ser Lys Ala Ser Thr Pro Asn Gly Tyr
                165                 170                 175

Asp Asn Gly Ile Ile Trp Ala Thr Trp Lys Thr Arg Trp Tyr Ser Met
            180                 185                 190

Lys Lys Thr Thr Met Lys Ile Ile Pro Phe Asn Arg Leu Thr Ile Gly
        195                 200                 205

Glu Gly Gln Gln His His Leu Gly Gly Ala Lys Gln Ala Gly Asp Val
    210                 215                 220
```

<210> SEQ ID NO 11
<211> LENGTH: 131
<212> TYPE: PRT
<213> ORGANISM: Homo sapiens

<400> SEQUENCE: 11

```
Ala Asn Arg Ser Arg Thr Glu Ala Glu Ser Trp Tyr Gln Thr Lys Tyr
1               5                   10                  15

Glu Glu Leu Gln Gln Thr Ala Gly Arg His Gly Asp Asp Leu Arg Asn
            20                  25                  30

Thr Lys His Glu Ile Ser Glu Met Asn Arg Met Ile Gln Arg Leu Arg
        35                  40                  45

Ala Glu Ile Asp Asn Val Lys Lys Gln Cys Ala Asn Leu Gln Asn Ala
    50                  55                  60

Ile Ala Asp Ala Glu Gln Arg Gly Glu Leu Ala Leu Lys Asp Ala Arg
65              70                  75                  80

Asn Lys Leu Ala Glu Leu Glu Glu Ala Leu Gln Lys Ala Lys Gln Asp
                85                  90                  95

Met Ala Arg Leu Leu Arg Glu Tyr Gln Glu Leu Met Asn Thr Lys Leu
            100                 105                 110

Ala Leu Asp Val Glu Ile Ala Thr Tyr Arg Lys Leu Leu Glu Gly Glu
        115                 120                 125

Glu Cys Arg
    130
```

```
<210> SEQ ID NO 12
<211> LENGTH: 129
<212> TYPE: PRT
<213> ORGANISM: Homo sapiens

<400> SEQUENCE: 12

Ala Glu Lys Asn Arg Lys Asp Ala Glu Glu Trp Phe Phe Thr Lys Thr
1               5                   10                  15

Glu Glu Leu Asn Arg Glu Val Ala Thr Asn Ser Glu Leu Val Gln Ser
            20                  25                  30

Gly Lys Ser Glu Ile Ser Glu Leu Arg Arg Thr Met Gln Asn Leu Glu
                35                  40                  45

Ile Glu Leu Gln Ser Gln Leu Ser Met Lys Ala Ser Leu Glu Asn Ser
        50                  55                  60

Leu Glu Glu Thr Lys Gly Arg Tyr Cys Met Gln Leu Ala Gln Ile Gln
65                  70                  75                  80

Glu Met Ile Gly Ser Val Glu Glu Gln Leu Ala Gln Leu Arg Cys Glu
                85                  90                  95

Met Glu Gln Gln Asn Gln Glu Tyr Lys Ile Leu Leu Asp Val Lys Thr
            100                 105                 110

Arg Leu Glu Gln Glu Ile Ala Thr Tyr Arg Arg Leu Leu Glu Gly Glu
        115                 120                 125

Asp

<210> SEQ ID NO 13
<211> LENGTH: 4
<212> TYPE: PRT
<213> ORGANISM: Homo sapiens

<400> SEQUENCE: 13

Gly His Arg Pro
1
```

FIBROUS PROTEINACEOUS NETWORKS AND METHODS OF USE THEREOF

RELATED APPLICATIONS

The application is the U.S. national phase of International Patent Application No. PCT/US2019/038501, filed Jun. 21, 2019; which claims the benefit of priority to U.S. Provisional Application No. 62/687,991, filed Jun. 21, 2018.

STATEMENT OF GOVERNMENT SUPPORT

This invention was made with government support under Grant No. 1410751 awarded by National Science Foundation. The government has certain rights in the invention.

BACKGROUND

Fibrous proteins such as collagen, elastin, keratin and fibrin perform key functions in the human body and are of high interest in the field of biomedical applications, especially in tissue engineering. Unfortunately, extraction, purification and synthesis of fibrous proteins can be difficult, time consuming, and expensive. For example, keratin extraction out of keratin-rich sources, like wool or hair, uses reducing agents containing thiols or oxidation methods which are and harmful to the environment and require a large amount of means, making those methods expensive. Moreover, chemicals used during keratin extraction are toxic and can damage the integrity of the extracted keratin. See Amin Shavandi et al., *In: Biomaterials Science,* 2017; David H Baker, *The Journal of Nutrition* 136.6, 2006; Mendal Friedman, *Journal of Agricultural and Food Chemistry,* 47.4, 1999.

Accordingly, there is a need for more efficient methods to extract or synthesize fibrous proteins, such as keratin and fibrin. Moreover, there is also a need for methods of production of bio-fabricated and environmentally friendly materials.

SUMMARY

Provided herein is a system which overcomes the known problems with manufacturing of fibrous proteins and bio-fabricated proteinaceous networks for use in a variety of fields. Specifically, the present disclosure provides engineered or genetically altered microorganisms, such as *E. coli*, that produce fibrous proteinaceous networks, such as curli fibers, that are fused to fibrous proteins such as fibrin, elastin, keratin or collagen. The engineered fusion protein nanofibers disclosed herein enable the fibrous protein to be displayed on a biofilm, without the need for purification or chemical modification. The fibrous proteins are co-expressed with amyloid nanofibers on the biofilm, and there is no need for chemical conjugation reagents. Moreover, the fusion proteins on the biofilm form a proteinaceous network that retains the mechanical properties and biological functions of the fibrous protein, therefore form a unique structure on the biofilm. The constructs disclosed herein are useful for creating a new material capable of, for example, being used as bacto-inks for three-dimensional printing (3D printing) and scaffolds for cell culturing in tissue engineering. The bacto-inks of the invention can further contain additional functional curli fibers or additional engineered bacteria that produce functional curli fibers. The bacto-inks containing functional curli fibers may be self-regenerating and have specific bioactivities. Such bacto-inks have applications in various fields such as biosensing, binding, signaling, and drug delivery.

In one aspect, the disclosure provides an amyloid fusion protein comprising an amyloid protein fused to one or more protein, or fragments thereof. In one embodiment, the one or protein is a fibrous protein. In one embodiment, the amyloid fusion protein is selected from the group consisting of CsgA and fragments thereof, A-beta, alpha-synuclein, TasA, and Sup35. In one embodiment, the amyloid fusion protein is CsgA, or a fragment thereof.

In one aspect, the disclosure provides an amyloid fusion protein comprising an amyloid protein fused to a fibrous protein. In one embodiment, the amyloid fusion protein is selected from the group consisting of CsgA and fragments thereof, A-beta, alpha-synuclein, TasA, and Sup35. In one embodiment, the amyloid fusion protein is CsgA, or a fragment thereof.

In one embodiment, the fibrous protein fused to the amyloid fusion protein is selected from the group consisting of keratin, elastin, fibrin and collagen, or a fragment thereof. In one embodiment, the fibrous protein fused to the amyloid fusion protein is fibrin, or a fragment thereof. In one embodiment, the fibrous protein fused to the amyloid fusion protein comprises an α chain of a fibrinogen. In one embodiment, the fibrous protein fused to the amyloid fusion protein comprises a sequence having at least 80% homology to SEQ ID NO:9. In one embodiment, the fibrous protein fused to the amyloid fusion protein comprises a γ chain of a fibrinogen. In one embodiment, the fibrous protein fused to the amyloid fusion protein comprises a sequence having at least 80% homology to SEQ ID NO:10.

In one embodiment, the fibrous protein fused to the amyloid fusion protein is a keratin. In one embodiment, the fibrous protein fused to the amyloid fusion protein is a K5 keratin. In one embodiment, the fibrous protein fused to the amyloid fusion protein comprises a sequence having at least 80% homology to SEQ ID NO:11. In one embodiment, the fibrous protein fused to the amyloid fusion protein comprises a K14 keratin. In one embodiment, the fibrous protein fused to the amyloid fusion protein comprises a sequence having at least 80% homology to SEQ ID NO:12.

In another aspect, the disclosure provides a plurality of amyloid fusion proteins comprising a first amyloid fusion protein and a second amyloid fusion protein, wherein the first amyloid fusion protein comprises a first amyloid protein fused to a first fibrous protein; and wherein the second amyloid fusion protein comprises a second amyloid protein fused to a second fibrous protein, wherein the first fibrous protein is capable of binding or is bound to the second fibrous protein.

In one embodiment, the first fibrous protein of the plurality of amyloid fusion proteins comprises an α chain of a fibrinogen, and the second fibrous protein comprises a γ chain of a fibrinogen. In one embodiment, the first fibrous protein of the plurality of amyloid fusion proteins comprises a sequence having at least 80% homology to SEQ ID NO:9, and the second fibrous protein comprises a sequence having at least 80% homology to SEQ ID NO:10.

In one embodiment, the first fibrous protein of the plurality of amyloid fusion proteins comprises a K5 keratin, and the second fibrous protein comprises a K14 keratin. In one embodiment, the first fibrous protein of the plurality of amyloid fusion proteins comprises a sequence having at least 80% homology to SEQ ID NO:11, and the second fibrous protein comprises a sequence having at least 80% homology to SEQ ID NO:12.

In one embodiment, the amyloid protein is selected from the group consisting of CsgA and fragments thereof, A-beta, alpha-synuclein, TasA, and Sup35. In one embodiment, the amyloid protein is CsgA, or a fragment thereof. In one embodiment, the CsgA, or fragment thereof, is an *E. coli* CsgA, or fragment thereof. In one embodiment, the *E. coli* CsgA comprises a sequence having at least 80% identity to SEQ ID NO:1.

In another aspect, the disclosure provides an isolated nucleic acid encoding any of the amyloid fusion proteins or the plurality of amyloid fusion proteins described herein.

In another aspect, the disclosure provides a vector comprising any of the isolated nucleic acids described herein.

In another aspect, the disclosure provides a curli fiber comprising any of the amyloid fusion proteins or the plurality of amyloid fusion proteins described herein.

In another aspect, the disclosure provides a fibrous proteinaceous network comprising any of the amyloid fusion proteins or the plurality of amyloid fusion proteins described herein.

In another aspect, the disclosure provides an engineered microbial cell comprising any of the amyloid fusion proteins or the plurality of amyloid fusion proteins described herein.

In another aspect, the disclosure provides an engineered microbial cell comprising the any of the isolated nucleic acids described herein.

In another aspect, the disclosure provides an engineered microbial cell expressing any of the curli fibers described herein. In one embodiment, the engineered microbial cell is an *E. coli* cell.

In another aspect, the disclosure provides a biomaterial comprising any of the amyloid fusion proteins or the plurality of amyloid fusion proteins, the curli fiber, or the fibrous proteinaceous network described herein.

In one embodiment, the biomaterial further comprises an engineered microbial cell.

In one embodiment, the biomaterial further comprises any of the engineered microbial cells described herein.

In another aspect, the disclosure provides a hydrogel comprising any of the amyloid fusion proteins or the plurality of amyloid fusion proteins disclosed herein, the curli fiber disclosed herein, or the fibrous proteinaceous network disclosed herein.

In another aspect, the disclosure provides a bioink comprising any one of the biomaterials disclosed herein.

In another aspect, the disclosure provides a bioink comprising a hydrogel disclosed herein.

In another aspect, the disclosure provides a method of producing a biomaterial capable of forming a fibrous proteinaceous network, the method comprising culturing a first genetically engineered bacterium in culture media, wherein the first genetically engineered bacterium expresses a first amyloid fusion protein comprising a first amyloid protein and a first fibrous protein, culturing a second genetically engineered bacterium in the culture media, wherein the second genetically engineered bacterium expresses a second amyloid fusion protein comprising a second amyloid protein and a second fibrous protein, wherein the first fibrous protein binds to the second fibrous protein, thereby forming a plurality of curli fibers which form a biomaterial, thereby producing a biomaterial capable of forming a fibrous proteinaceous network.

In another aspect, the disclosure provides a method of producing a biomaterial capable of forming a fibrous proteinaceous network, the method comprising culturing a first genetically engineered bacterium in a first culture media, wherein the first genetically engineered bacterium expresses a first amyloid fusion protein comprising a first amyloid protein and a first fibrous protein, culturing a second genetically engineered bacterium in a second culture media, wherein the second genetically engineered bacterium expresses a second amyloid fusion protein comprising a second amyloid protein and a second fibrous protein, mixing the first culture media and the second culture media, wherein the first fibrous protein binds to the second fibrous protein, thereby forming a plurality of curli fibers which form a biomaterial, thereby producing a biomaterial capable of forming a fibrous proteinaceous network.

In one embodiment, the first fibrous protein and the second fibrous protein of the method are selected from the group consisting of keratin, elastin, fibrin and collagen.

In one embodiment, the first fibrous protein and the second fibrous protein of the method are a fibrin. In one embodiment, the first fibrous protein of the method is an α chain of a fibrinogen, and the second fibrous protein of the method is a γ chain of a fibrinogen. In one embodiment, the first fibrous protein of the method comprises a sequence having at least 80% homology to SEQ ID NO:9, and the second fibrous protein of the method comprises a sequence having at least 80% homology to SEQ ID NO:10.

In one embodiment, the first fibrous protein and the second fibrous protein of the method are a keratin. In one embodiment, the first fibrous protein of the method is a K5 keratin, and the second fibrous protein of the method is a K14 keratin. In one embodiment, the first fibrous protein of the method comprises a sequence having at least 80% homology to SEQ ID NO:11, and the second fibrous protein of the method comprises a sequence having at least 80% homology to SEQ ID NO:12.

In one embodiment, the first amyloid protein and the second amyloid protein of the method are selected from the group consisting of CsgA and fragments thereof, A-beta, alpha-synuclein, TasA, and Sup35. In one embodiment, the first amyloid protein and the second amyloid protein of the method is CsgA, or a fragment thereof. In one embodiment, the CsgA, or fragment thereof of the method, is an *E. coli* CsgA, or fragment thereof. In one embodiment, the *E. coli* CsgA of the method comprises a sequence having at least 80% identity to SEQ ID NO:1.

In one embodiment, the first genetically engineered bacterium and the second genetically engineered bacterium of the method are a first genetically engineered *E. coli* bacterium and a second genetically engineered *E. coli* bacterium.

In one embodiment, the method further comprises a step of removing the first genetically engineered bacterium and the second genetically engineered bacterium from the biomaterial.

In one embodiment, the removing step of the method further comprises washing the first genetically engineered bacterium and the second genetically engineered bacterium from the biomaterial. In one embodiment, the removing step of the method comprises killing the first genetically engineered bacterium and the second genetically engineered bacterium in the biomaterial.

In one embodiment, the method further comprises forming a hydrogel.

In one embodiment, the method further comprises forming a bioink.

In another aspect, the disclosure provides use of any of the hydrogels or bioinks described herein as an ink for three-dimensional printing ("3D" printing).

In another aspect, the disclosure provides use of any of the hydrogels or bioinks disclosed herein as a sealant and scaffold for wound dressing or tissue engineering.

In another aspect, the disclosure provides a bioink comprising biomaterials selected from the group consisting of calcium hydroxyapatite, cellulose, chitin and silica.

Further features and advantages of certain embodiments of the present invention will become more fully apparent in the following description of embodiments and drawings thereof, and from the claims.

BRIEF DESCRIPTION OF THE DRAWINGS

The foregoing and other features and advantages of the present embodiments will be more fully understood from the following detailed description of illustrative embodiments taken in conjunction with the accompanying drawings in which:

FIGS. 3A 3B, 3C, 3D, 3E, and 3F depict keratin fiber aggregation of mixed and co-culture method. All bacteria were expressing fibers for 48 hours in a shaking incubator for 48 hours, at 37° C. and 225 rpm. Bacterial ECM displaying CsgA-K5 or CsgA-K14 alone shows little aggregation of only CsgA-K5 fibers (FIG. 3A) or little aggregation of only CsgA-K14 fibers (FIG. 3B). Bacterial ECM displaying CsgA-K5K14$_{mixed}$ shows dense fiber aggregation of CsgA-K5K14$_{mixed}$ fibers (FIGS. 3C-3E). Bacterial ECM displaying CsgA-K5K14$_{co-cultured}$ shows higher fiber aggregation of CsgA-K5K14$_{co-cultured}$ fibers after 48 hours (FIG. 3F).

FIG. 4A depicts CsgA-α based hydrogel showing a small pore size structure. FIG. 4B depicts CsgA-γ based hydrogel with large pore size. FIG. 4C depicts formation of aligned looking fibers of CsgA-$αγ_{mixed}$ based hydrogels. FIG. 4D depicts CsgA-$αγ_{co-cultured}$ based hydrogel, showing similar alignment as for CsgA-$αγ_{mixed}$ based hydrogels.

FIGS. 12A and 12B depict self-regeneration of 3D printing ink comprising of CsgA-$αγ_{cocultured}$ and bacteria that produces CsgA-α and CsgA-γ. Optical image of the grid after 1 hour (FIG. 12A) and 2 days (FIG. 12B) of printing.

DETAILED DESCRIPTION

Figure 1A:
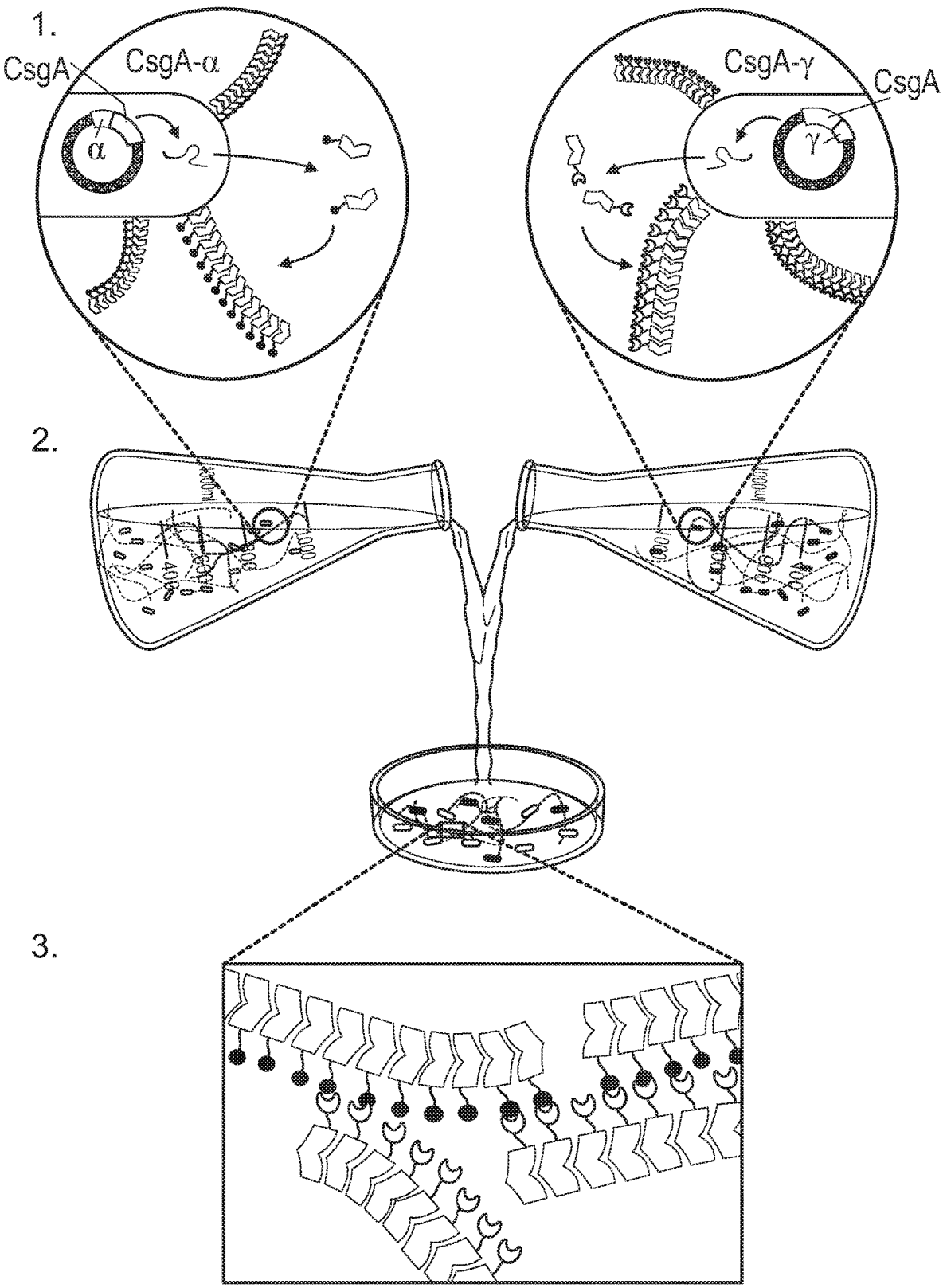
FIGS. 1A and 1B depict concepts of network formation through mixing of two bacteria cultures (FIG. 1A) or co-culturing the matching bacteria (FIG. 1B).

Disclosed herein are engineered bacteria which are capable of producing one or more nanofibers comprising a fusion protein. The engineered bacteria disclosed herein allow for the co-expression of amyloid nanofibers and a fibrous protein on the surface of a biofilm, and the formation of fibrous proteinaceous networks on the biofilm. Such amyloid nanofibers and biofilms are useful for creating a new material capable of, for example, being used as bacto-inks for three-dimensional printing (3D printing) and scaffolds for cell culturing in tissue engineering. Aspects of the present disclosure use principles of Biofilm Integrated Nanofiber Display (BIND).

In order that the disclosure may be more readily understood, certain terms are first defined. These definitions should be read in light of the remainder of the disclosure and as understood by a person of ordinary skill in the art. Unless defined otherwise, all technical and scientific terms used herein have the same meaning as commonly understood by a person of ordinary skill in the art. Additional definitions are set forth throughout the detailed description.

Definitions

As used herein, an "amyloid", "amyloidogenic protein", or "amyloid-based structure" refers to an polymeric aggregate of amyloid polypeptides. In some embodiments, the amyloid-based structure forms a structure of fibrillary morphology. In some embodiments, the amyloid-based structure is a curli fiber. In some embodiments, the amyloid-based structure is formed by a heterogeneous population of amyloid polypeptides. In some embodiments, the amyloid-based structure is formed by a homogenous population of amyloid polypeptides. An amyloid-based structure may be formed by any population of amyloid polypeptides, including but not limited to CsgA, A-beta, alpha-synuclein, TasA, Sup35, or other functional amyloids derived from bacteria and fragments and mutants of CsgA. In one embodiment, the amyloid protein is CsgA.

As used herein, the term "curli fiber" refers to the primary proteinaceous structural component of *E. coli* biofilms. Curli fibers are highly robust functional amyloid nanofibers with a diameter of ~4-7 nm that exist as extended tangled networks encapsulating the cells. Curli fibers are formed from the extracellular self-assembly of CsgA, a small secreted 13-kDa protein. A "plurality of curli fibers" refers to more than one curli fiber.

As used herein, "CsgA" refers to the major structural subunit of the curli fiber. The sequences of CsgA and its homologs are known in a number of species. For example, the sequence of *E. coli* CsgA is known (NCBI Gene ID NO: 949055; (polypeptide)). CsgA polypeptide (NCBI Ref Seq: NP_415560):

(SEQ ID NO: 1)
mkllkvaaiaaivfsgsalagvvpqyggggnhggggnnsgpnselniyqy gggnsalalqtdarnsdltitqhgggngadvgqgsddssidltqrgfgns atldqwngknsemtvkqfgggngaavdqtasnssvnvtqvgfgnnatahq y.

A CsgA protein may include naturally occurring mutations or variants of CsgA, homologs of CsgA, or engineered mutations or variants of CsgA. In some embodiments, "CsgA" refers to *E. coli* CsgA. In some embodiments, "CsgA" refers to a polypeptide having at least 80% homology to SEQ ID NO:1 (e.g., 80% or greater homology, 90% or greater homology, or 95% or greater homology).

As used herein, "fibrous protein" is a member of a class of long, filamentous proteins that form connective tissue, tendons, bone and muscle fiber in animal and human bodies. Fibrous proteins form "rod" or "wire"-like shapes and are usually inert structural or storage proteins. In one aspect, a fibrous protein is a full-length protein that contains multiple subunits that form a filament. In one aspect, a fibrous protein is a subunit or a polypeptide chain of a protein that forms a filament. In one aspect, a fibrous protein is a fragment of a subunit or a polypeptide chain of a protein that forms a filament. In some embodiments, a fibrous protein is a full-length keratin, a subunit of a keratin, or a fragment of a subunit of a keratin. In some embodiments, a fibrous protein is a full-length elastin, a subunit of an elastin or a fragment of a subunit of an elastin. In some embodiments, a fibrous protein is a full-length fibrin, a subunit of a fibrin or a fragment of a subunit of a fibrin. In other embodiments, a fibrous protein is a full-length collagen, a subunit of a collagen or a fragment of a subunit of a collagen.

The terms "protein" and "polypeptide" are used interchangeably herein to designate a series of amino acid residues, connected to each other by peptide bonds between the alpha-amino and carboxy groups of adjacent residues. The terms "protein," and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

A "nucleic acid" or "nucleic acid sequence" may be any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable nucleic acid molecules are DNA, including genomic DNA or cDNA. Other suitable nucleic acid molecules are RNA, including mRNA.

As used herein, the term "gene" refers to a nucleic acid fragment that encodes a protein or fragment thereof, optionally including regulatory sequences preceding (5' non-coding sequences) and following (3' non-coding sequences) the coding sequence. In one embodiment, a "gene" does not include regulatory sequences preceding and following the coding sequence. Each gene may be present on a plasmid or bacterial chromosome. In addition, multiple copies of any gene may be present in the bacterium, wherein one or more copies of the gene may be altered as described herein.

A "native gene" refers to a gene as found in nature, optionally with its own regulatory sequences preceding and following the coding sequence. A "chimeric gene" refers to any gene that is not a native gene, optionally comprising regulatory sequences preceding and following the coding sequence, wherein the coding sequences and/or the regulatory sequences, in whole or in part, are not found together in nature. Thus, a chimeric gene may comprise regulatory sequences and coding sequences that are derived from different sources, or regulatory and coding sequences that are derived from the same source, but arranged differently than is found in nature.

As used herein, the term "endogenous gene" refers to a native gene in its natural location in the genome of an organism.

As used herein, a "heterologous" gene or "heterologous sequence" refers to a nucleotide sequence that is not normally found in a given cell in nature. As used herein, a heterologous sequence encompasses a nucleic acid sequence that is exogenously introduced into a given cell. "Heterologous gene" includes a native gene, or fragment thereof, that has been introduced into the host cell in a form that is different from the corresponding native gene. For example, a heterologous gene may include a native coding sequence that is a portion of a chimeric gene to include a native coding sequence that is a portion of a chimeric gene to include non-native regulatory regions that is reintroduced into the host cell. A heterologous gene may also include a native gene, or fragment thereof, introduced into a non-native host cell. Thus, a heterologous gene may be foreign or native to the recipient cell; a nucleic acid sequence that is naturally found in a given cell but expresses an unnatural amount of the nucleic acid and/or the polypeptide which it encodes; and/or two or more nucleic acid sequences that are not found in the same relationship to each other in nature.

As used herein, the term "expression" refers to the transcription and stable accumulation of sense (mRNA) or anti-sense RNA derived from a nucleic acid, and/or to translation of an mRNA into a polypeptide.

As used herein, the term "plasmid" or "vector" refers to an extrachromosomal nucleic acid, e.g., DNA, construct that is not integrated into a bacterial cell's genome. Plasmids are usually circular and capable of autonomous replication. Plasmids may be low-copy, medium-copy, or high-copy, as is well known in the art. Plasmids may optionally comprise a selectable marker, such as an antibiotic resistance gene, which helps select for bacterial cells containing the plasmid and which ensures that the plasmid is retained in the bacterial cell. A plasmid may comprise a nucleic acid sequence encoding a heterologous gene or gene cassette.

As used herein, the term "transform" or "transformation" refers to the transfer of a nucleic acid fragment into a host bacterial cell, resulting in genetically-stable inheritance. Host bacterial cells comprising the transformed nucleic acid fragment are referred to as "recombinant" or "transgenic" or "transformed" organisms.

As used herein, the term "engineered microbial cell" or "engineered bacterial cell" refers to a bacterial cell or bacteria that have been genetically modified from their native state. For instance, an engineered bacterial cell may have nucleotide insertions, nucleotide deletions, nucleotide rearrangements, and nucleotide modifications introduced into their DNA. These genetic modifications may be present in the chromosome of the bacteria or bacterial cell, or on a plasmid in the bacteria or bacterial cell. Engineered bacterial cells disclosed herein may comprise exogenous nucleotide sequences on plasmids. Alternatively, engineered bacterial cells may comprise exogenous nucleotide sequences stably incorporated into their chromosome.

As used herein, the term "fusion", "protein fusion" or "fusion protein" refers to a chimeric protein created through the joining of two or more genes that originally encoded separate proteins. A protein fusion is created artifically using recombinant DNA technology. Disclosed herein are amyloidogenic proteins fused, or linked, to a polypeptide (e.g., a fibrous protein). In one aspect, the amyloidogenic protein is fused to a fibrous protein. In one embodiment, a CsgA may be fused directly to a fibrous protein. In one embodiment, a CsgA may be fused to a subunit of a fibrous protein (e.g., an α chain of a fibrin, a γ chain of a fibrin). In one embodiment, a CsgA may be fused to a fragment of a subunit of a fibrous protein (e.g., a fragment of an α chain of a fibrin, a γ chain of a fibrin, a fragment of K5 keratin or a fragment of K14 keratin). In another embodiment, a CsgA may be fused indirectly, e.g., by a linker, to a fibrous protein, a subunit of a fibrous protein or a fragment of a subunit of a fibrous protein.

As used herein, the term "bound to" refers to an interaction between to molecules or proteins. A protein may be covalently or non-covalently bound to another protein or molecule. As used herein, a "covalent bond" refers to a chemical bond that involves the sharing of electron pairs between atoms. In contrast, a "non-covalent bond" does not involve the sharing of electrons, but involves more dispersed variations of electromagnetic interactions between molecules. Non-covalent bonds include, but are not limited to, electrostatic, van der Walls forces, and hydrophobic effects.

As used herein the term "plurality" refers to more than one kind or type of a particular unit. A "plurality of curli fibers" refers to more than one type of curli fiber, wherein the curli fibers have different properties, functions and/or activities. For example, a plurality of curli fibers can be two types of curli fibers, wherein the first curli fiber has a first functionalizing polypeptide, and the second curli fiber has a second functionalizing polypeptide, wherein the first and second functionalizing polypeptides are different and confer different properties, functions and/or activities to the curli fibers.

As used herein, a "proteinaceous network" refers to a network formed by protein-protein interactions. In one aspect, a proteinaceous network is formed by the interactions between fibrous proteins. In one aspect, a proteinaceous network is formed by the interactions between amyloidogenic proteins. In one aspect, a proteinaceous network is formed by the interactions between fibrous proteins and amyloidogenic proteins In one embodiment, a proteinaceous network is a fibrous network formed by the interactions between keratins. In one embodiment, a proteinaceous network is a fibrous network formed by the interactions between fibrins. In one embodiment, a proteinaceous network if a fibrous network formed by the interactions between fragments of keratins. In one embodiment, a proteinaceous network is a fibrous network formed by the interactions between fragments of fibrins.

As used herein, a "hydrogel" is a macromolecular polymer gel constructed of a network of crosslinked polymer chains. In one embodiment, a hydrogel is a network of curli fibers fused to fibrous proteins. In one embodiment, a hydrogel is a biofilm comprising a proteinaceous network of curli fibers fused to fibrous proteins.

As used herein, a "linker" or a "spacer" refers to a polypeptide domain inserted between two proteins in a protein fusion. For example, a linker or a spacer can be about 100 amino acids or less in size, about 75 amino acids or less in size, about 50 amino acids or less in size, about 40 amino acids or less in size, or smaller. In one aspect, linkers and spacers are inserted between a CsgA protein and a fibrous protein.

As used herein, the term "biofilm matrix" refers to a matrix of extracellular polymeric substances, including, but not limited to extracellular DNA, proteins, glycopeptides, and polysaccharides, which was produced by a mass of microorganisms, such as bacteria, but wherein the microorganisms have been completely or almost completely killed or removed. Accordingly, in one embodiment, a "biofilm matrix" does not comprise any microorganisms, such as bacteria. In one embodiment, a "biofilm matrix" does not comprise any live microorganisms, such as bacteria.

As used herein, the term "biofilm" refers to a matrix of extracellular polymeric substances, including, but not limited to extracellular DNA, proteins, glycopeptides, and polysaccharides, which are produced by a mass of microorganisms, such as bacteria. In one embodiment, a biofilm comprises a biofilm matrix and bacteria. In one embodiment, the bacteria are live bacteria.

As used herein, the term "biomaterial" refers to a natural or synthetic material made of multiple components which interacts with biological systems. In some embodiment, a biomaterial is a biofilm. In some embodiments, a biomaterial is a biofilm matrix. In some embodiments, a biomaterial is a hydrogel that comprises a fibrous proteinaceous network. In some embodiments, a biomaterial is a bioink used for 3D-printing.

As used herein, the term "bioinks" or "bacto-inks" refers to 3D printable inks fabricated or produced directly from genetically engineered bacteria. In some embodiments, a bioink is developed from a hydrogel comprising a fibrous proteinaceous network. In some embodiments, a bioink is developed from a hydrogel comprising functional and structural biomaterials such as calcium hydroxyapatite, cellulose, chitin and silica. In some embodiments, a bioink is BactoPrink.

As used herein, "BactoPrink" is a bioink employed to 3D print functional and structural biomaterials. In some embodiments, BactoPrink is a hydrogel comprising a fibrous proteinaceous network. In some embodiments, BactoPrink is developed from a hydrogel comprising functional and structural biomaterials such as calcium hydroxyapatite, cellulose, chitin and silica.

Definitions of common terms in cell biology and molecular biology can be found in The Encyclopedia of Molecular Biology, published by Blackwell Science Ltd., 1994 (ISBN 0-632-02182-9); Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

The articles "a" and "an," as used herein, should be understood to mean "at least one," unless clearly indicated to the contrary.

The phrase "and/or," when used between elements in a list, is intended to mean either (1) that only a single listed element is present, or (2) that more than one element of the list is present. For example, "A, B, and/or C" indicates that the selection may be A alone; B alone; C alone; A and B; A and C; B and C; or A, B, and C. The phrase "and/or" may be used interchangeably with "at least one of" or "one or more of" the elements in a list.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Curli Fibers

Curli fibers are the primary proteinaceous structural component of biofilms. They are highly robust functional amyloid nanofibers with a diameter of ~4-7 nm that exist as extended tangled networks encapsulating the cells. Curli fibers are formed from the extracellular self-assembly of CsgA, a small secreted 13-kDa protein, see Chapman, M. R. et al. Role of *Escherichia coli* curli operons in directing amyloid fiber formation. *Science* 295, 851-855 (2002), hereby incorporated by reference in its entirety. A homologous outer-membrane protein, CsgB, nucleates CsgA assembly and also anchors the nanofibers to the bacterial surface. Detached curli fibers can also exist as non-cell associated structural components of the extra-cellular membrane (ECM). The curli genes exist as two divergently transcribed operons (csgBAC and csgDEFG), whose seven products mediate the structure (CsgA), nucleation (CsgB), processing (CsgE, F), secretion (CsgC, G), and direct transcriptional regulation (CsgD) of curli nanofibers. This curli secretion system is considered a distinct secretion system of its own in gram-negative bacterium and is named the Type-VIII secretion system (T8SS). See Desvaux et al., *Trends Microbiol.* 17, 139-45 (2009) hereby incorporated by reference in its entirety.

In one aspect, *E. coli* expressing curli fibers may be used for the methods disclosed herein. In another aspect, other useful bacteria with suitable secretions systems known to those of skill in the art may be used to produce the electrically conductive curli fibers of the present disclosure. The bacterium can be non-pathogenic.

As used herein, "CsgA" refers to the major structural subunit of the curli fiber. The sequences of CsgA and its homologs are known in a number of species, e.g., the sequence of *E. coli* CsgA is known (NCBI Gene ID NO: 949055; (polypeptide)). CsgA polypeptide (NCBI Ref Seq: NP_415560):

```
                                          (SEQ ID NO: 1)
mkllkvaaiaaivfsgsalagvvpqygggnhggggnnsgpnselniyqy gggnsalalqtdarnsdltitqhgggngadvgqgsddssidltqrgfgns atldqwngknsemtvkqfgggngaavdqtasnssvnytqvgfgnnatahq y.
```

In some embodiments, "CsgA" refers to *E. coli* CsgA. In some embodiments, "CsgA" refers to a polypeptide having at least 80% homology to SEQ ID NO:1 (e.g., 80% or greater homology, 90% or greater homology, or 95% or greater homology), e.g., naturally occurring mutations or variants of CsgA, homologs of CsgA, or engineered mutations or variants of CsgA.

As used herein, a "CsgA fusion" or an "engineered CsgA polypeptide" refers to a CsgA polypeptide comprising a heterologous polypeptide fused to the CsgA at either the C-terminus or the N terminus or both, but without interrupting the sequence of the CsgA polypeptide. In one aspect, a fibrous protein is fused to a CsgA protein at the C-terminus of the CsgA protein and it self-assembles into a curli fiber. A plurality of curli fibers displaying one or more fibrous proteins or protein fragments is capable of forming a fibrous proteinaceous network.

A "plurality of curli fibers" refers to more than one curli fiber. In one embodiment, a "plurality of curli fibers" refers to more than one type of curli fiber, wherein the curli fibers have different properties, functions and/or activities. For example, a plurality of curli fibers comprises two types of curli fibers, wherein the first curli fiber is fused to a first fibrous protein or a fragment of a fibrous protein, and the second curli fiber is bound to a second fibrous protein or a fragment of a fibrous protein, wherein the first and second fibrous proteins are different and confer different properties, functions and/or activities to each curli fiber. In some embodiments, a plurality of curli fibers comprises 2 different types of curli fibers.

Biofilms

Bacterial biofilms are constructed from protective nanoscale scaffolds of proteins, sugars, lipids, and extracellular DNA, and biofilms are self-generated protective structures that allow bacteria to adhere to both natural and man-made surfaces. See U.S. Pat. No. 9,815,871, granted on Nov. 14, 2017, the entire contents of which are expressly incorporated herein by reference in their entirety.

As used herein, the term "biofilm" refers to a matrix of extracellular polymeric substances, including, but not limited to extracellular DNA, proteins, glycopeptides, and polysaccharides, which are produced by a mass of microorganisms, such as bacteria. The nature of a biofilm, such as its structure and composition, can depend on the particular species of bacteria present in the biofilm. Bacteria present in a biofilm are commonly genetically or phenotypically different than corresponding bacteria not in a biofilm, such as isolated bacteria or bacteria in a colony. The biofilms disclosed herein are generally produced by culturing an engineered microbial cell comprising a CsgA fusion (and/or comprising a vector or nucleic acid encoding such a polypeptide) under conditions suitable for the production of curli fibers.

Conditions suitable for the production of a biofilm can include, but are not limited to, conditions under which a microbial cell is capable of logarithmic growth and/or polypeptide synthesis. Conditions may vary depending upon the species and strain of microbial cell selected. Conditions for the culture of microbial cells are well known in the art. Biofilm production can also be induced and/or enhanced by methods well known in the art, e.g., contacting cells with sub-inhibitory concentrations of beta-lactam or aminoglycoside antibiotics, exposing cells to fluid flow, contacting cells with exogenous poly-N-acetylglucosamine (PNAG), or contacting cells with quorum sensing signal molecules. In some embodiments, conditions suitable for the production of a biofilm can also include conditions which increase the expression and secretion of CsgA, e.g., by exogenously expressing CsgD.

In one embodiment, a biofilm refers to the matrix of extracellular polymeric substances that is produced by a mass of microorganisms, wherein the bacteria have been killed or removed. In one embodiment, a biofilm does not comprise any bacteria. In another embodiment, a biofilm does not comprise any live bacteria. In some embodiments, the biofilm can further include the bacterium which produced the biofilm.

Biofilms disclosed herein may be produced by genetically engineering or modifying bacteria to comprise a nucleic acid encoding a CsgA fusion, consisting of a CsgA protein linked to a fibrous protein (e.g., keratin, elastin, fibrin or collagen), and growing the engineered bacteria in situ or in culture media. The nucleic acid encoding a CsgA protein fused to the fibrous protein may be heterologous and introduced into the bacterium using methods known to those of skill in the art. The nucleic acid encoding a fusion CsgA protein may result from mutation of the endogenous nucleic acid encoding CsgA using methods known to those of skill in the art. In one embodiment, the biofilm is produced by engineered bacteria comprising a nucleic acid encoding CsgA protein fused to a fibrous protein. The CsgA protein may be fused to the fibrous with a linker domain in between.

A "vector" includes a nucleic acid construct designed for delivery to a host cell or transfer between different host cells. A vector can be viral or non-viral. Many vectors useful for transferring genes into target cells are available, e.g., the vectors may be episomal, e.g., plasmids, virus derived vectors or may be integrated into the target cell genome, through homologous recombination or random integration. In some embodiments, a vector can be an expression vector. An "expression vector" can be a vector that has the ability to incorporate and express heterologous nucleic acid fragments in a cell. An expression vector may comprise additional elements, for example, the expression vector may have two replication systems, thus allowing it to be maintained in two organisms. The nucleic acid incorporated into the vector can be operatively linked to an expression control sequence when the expression control sequence controls and regulates the transcription and translation of that polynucleotide sequence.

In some embodiments, a nucleic acid encoding a CsgA fusion can be present within a portion of a plasmid. Plasmid vectors can include, but are not limited to, pBR322, pBR325, pACYC177, pACYC184, pUC8, pUC9, pUC18, pUC19, pLG339, pR290, pKC37, pKC101, SV 40, pBluescript II SK+/− or KS+/−(see "Stratagene Cloning Systems" Catalog (1993) from Stratagene, La Jolla, Calif., which is hereby incorporated by reference), pQE, pIH821, pGEX, pET series (see Studier et. al., "Use of T7 RNA Polymerase to Direct Expression of Cloned Genes," Gene Expression Technology, vol. 185 (1990), which is hereby incorporated by reference in its entirety). In one embodiment, the plasmid vector is a pET21d plasmid. In one embodiment, a nucleic acid encoding a CsgA fused to a fibrous protein is present in a pET21d plasmid.

The engineered bacteria can secrete the CsgA fusion, which results in curli fiber production, followed by biofilm formation. Specifically, after secretion, the CsgA fusion is nucleated to form a self-assembling amyloid at the cell surface, and then continues to polymerize into long fibers that eventually encapsulate the cells and provide the biofilm with structural support. In one embodiment, the CsgA is fused to a fibrous protein, resulting in the formation of a fibrous proteinaceous network. In one embodiment, the fibrous protein is keratin. In one embodiment, the fibrous protein is elastin. In one embodiment, the fibrous protein is fibrin. In another embodiment, the fibrous protein is collagen.

A bacterial cell described herein can be of any species. Preferably, the bacterial cells are of a species and/or strain which is amenable to culture and genetic manipulation. In some embodiments, the bacterial cell can be a gram-positive bacterial cell. In some embodiments, the bacterial cell can be a gram-negative bacterial cell. In some embodiments, the parental strain of the bacterial cell of the technology described herein can be a strain optimized for protein expression. Non-limiting examples of bacterial species and strains suitable for use in the present technologies include *Escherichia coli*, *E. coli* BL21, *E. coli* Tuner, *E. coli* Rosetta, *E. coli* JM101, and derivatives of any of the foregoing. Bacterial strains for protein expression are commercially available, e.g., EXPRESS™ Competent *E. coli* (Cat. No. C2523; New England Biosciences; Ipswich, MA). In one embodiment, the curli fibers are produced by engineered or non-naturally occurring bacterium. In one embodiment, the bacterium is *E. coli*. In one embodiment, the bacterium is PNQ4 (*E. coli* strain derived from LSR10 (MC4100, ΔCsgA, λ(DE3), CamR)) which was constructed to knockout the curli operon. In one embodiment, the bacterium is non-pathogenic.

In one embodiment, disclosed herein are methods of producing a biofilm by culturing an engineered bacteria in culture media, wherein the engineered bacteria comprises a nucleic acid sequence encoding a curli fiber fused to a fibrous protein. In one embodiment, the fibrous protein is keratin. In one embodiment, the fibrous protein is elastin. In one embodiment, the fibrous protein is fibrin. In another embodiment, the fibrous protein is collagen.

Fibrous Proteins and Formation of Fibrous Proteinaceous Networks

Fibrous proteins such as collagen, elastin, keratin and fibrin form networks and have various important functions in the human body. They contribute to the formation of connective tissues, are crucial for wound healing and blood coagulation, and provide structural support for cells in form of intermediate filaments (IFs). Furthermore, fibrous proteins are major components of the ECM and contribute to its structure and stiffness, see Christian Frantz, Kathleen M Stewart, and Valerie M Weaver, "The extracellular matrix at a glance," *J Cell Sci* 123.24 (2010), pp. 4195-4200. Cell-matrix interaction is of great importance to many physiological processes ranging from cell communication, motility, migration, cell fate and morphology. See D L Humphries, J A Grogan, and E A Gaffney, "Mechanical Cell-Cell Communication in Fibrous Networks: The Importance of Network Geometry," *Bulletin of mathematical biology* 79.3 (2017), pp. 498-524. Furthermore, an intact ECM is vital for wound healing and essential in the field of tissue engineering, where engineered biocompatible scaffolds are often formulated with naturally existing ECM proteins. See Youhwan Kim et al. "Extracellular Matrix Revisited: Roles in Tissue Engineering," *International neurourology journal* 20.Suppl 1 (2016), S23. Consequently, abnormal ECM structures can lead to congenital defects, deregulated cell proliferation or loss of cell differentiation, and is linked to altered intrinsic cell function. See Pengfei Lu et al. "Extracellular matrix degradation and remodeling in development and disease," *Cold Spring Harbor perspectives in biology* 3.12 (2011), a005058; Shelly R Peyton et al. "The emergence of ECM mechanics and cytoskeletal tension as important regulators of cell function," *Cell biochemistry and biophysics* 47.2 (2007), pp. 300-320. Thus, it takes a role in many pathological processes, including fibrosis and tumor invasion. See Pengfei Lu et al. "Extracellular matrix degradation and remodeling in development and disease," *Cold Spring Harbor perspectives in biology* 3.12 (2011), a005058.

Any of known fibrous protein can be utilized in the CsgA-fibrous protein fusions disclosed herein. In some embodiments, the fibrous protein is keratin. Keratin is used for the production of hair or nails, but is also playing an important role for the structural framework of the cell in form of intermediate filaments. See GM Cooper. The Cell: A Molecular Approach, 2nd edn. *The Cell: A Molecular Approach*, Sunderland, MA 2000; Chang-Hun Lee et al. "Structural basis for heteromeric assembly and perinuclear organization of keratin filaments," *Nature structural & molecular biology* 19.7 (2012), pp. 707-715. Keratin provides structural support to the cells and allows them to migrate, proliferate and differentiate, and keratin intermediate filaments are formed through copolymerization of one acidic (type I) and one basic (type II) keratin protein, which are synthesized by epithelial cells. See Chang-Hun Lee et al. "Structural basis for heteromeric assembly and perinuclear organization of keratin filaments," *Nature structural & molecular biology* 19.7 (2012), pp. 707-715.

The first step in the development of intermediate filaments is the formation of dimers, characterized through a coiled coil structure of two polypeptide chains (here acidic and basic keratin) that are wound together. As the dimers associate in a staggered antiparallel manner, they form tetramers, which can further assemble to form protofilaments. Protofilaments finally wind around each other to form intermediate filaments. See GM Cooper. The Cell: A Molecular Approach, 2nd edn. *The Cell: A Molecular Approach*, Sunderland, MA 2000; Sergei V Strelkov et al. "Conserved segments 1A and 2B of the intermediate filament dimer: their atomic structures and role in filament assembly," *The EMBO journal* 21.6 (2002), pp. 1255-1266; Peter M Steinert et al. "Keratin intermediate filament structure: crosslinking studies yield quantitative information on molecular dimensions and mechanism of assembly," *Journal of molecular biology* 230.2 (1993), pp. 436-452.

The mechanical resilience of intermediate filament networks is crucial for the structural support of the cell. See JM Bonifas, A L Rothman, and EH Epstein Jr. "Epidermolysis bullosa simplex: evidence in two families for keratin gene abnormalities," *Science* 254.5035 (1991), p. 1202. The integrity of those filaments is depending mainly on two factors. On one side, from concentration and length of the filaments. On the other side, from stable linkages between the filaments. The most studied keratin pair is keratin "K5" (type II) and "K14" (type I). This pair forms extremely stable tetramer subunits and organizes into cross-linked intermediate filament networks through interaction of the distal half of K14's tail domain and two distinct regions in K5's rod domain. See Pierre A Coulombe and Elaine Fuchs. "Elucidating the early stages of keratin filament assembly," *The Journal of Cell Biology* 111.1 (1990), pp. 153-169. The interface of K5-K14 coiled-coil heterodimer is characterized through non-covalent linkages of electrostatic interaction, hydrophobic interactions and hydrogen bonds as shown in picture 1. Mutations in either K5 or K14 are directly involved in a broad range of diseases, including many epithelial blistering disorders like epidermolysis bullosa simplex, underlying the importance of keratin's intracellular function. See JM Bonifas, A L Rothman, and EH Epstein Jr. "Epidermolysis bullosa simplex: evidence in two families for keratin gene abnormalities," *Science* 254.5035 (1991), p. 1202.

Besides the central role in the structural support of the cell, keratin has gained a greater interest in the field of biomedical engineering over the past decades. Keratin has the ability to facilitate cell adhesion, cell proliferation and promote tissue regeneration by creating cell binding domains such like fibronectin. See Mira Park et al. "Effect of discarded keratin-based biocomposite hydrogels on the wound healing process in vivo," In: Materials Science and Engineering: C 55 (2015), pp. 88-94; Paulina Sierpinski et al. "The use of keratin biomaterials derived from human hair for the promotion of rapid regeneration of peripheral nerves," *Biomaterials* 29.1 (2008), pp. 118-128; Amin Shavandi et al. "Dissolution, Extraction and Biomedical Application of Keratin: Methods and Factors Affecting the Extraction and Physicochemical Properties of Keratin," *Biomaterials Science* (2017). Moreover, keratin can function as a synthetic ECM due to its biodegradability and biocompatibility. Thus, keratin-based biomaterials have the potential to be a suitable platform for tissue engineering applications.

In one embodiment, the CsgA is fused to a full-length keratin. In one embodiment, the CsgA is fused to a fragment or a motif of a subunit of a keratin. In one embodiment, the CsgA is fused to K5. In another embodiment, the CsgA is fused to K14.

In some embodiments, the fibrous protein is fibrin. Fibrin is responsible for blood coagulation and therefore a key protein in human body. Additionally, fibrin provides an excellent scaffold for fibroblast adhesion and proliferation, and formation of granulation tissue. Therefore, fibrin contributes significantly in the process of wound healing. See Richard A F Clark. "Fibrin and wound healing," *Annals of the New York Academy of Sciences* 936.1 (2001), pp. 355-367. Furthermore, fibrin derived polymer, fibrin glue, has a great importance in surgery where it can be used as a tissue glue and act as an alternative to sutures. See Anita Panda et al. "Fibrin glue in ophthalmology," *Indian Journal of Ophthalmology* 57.5 (2009), p. 371. The formation of fibrin is the final step in the coagulation cascade. Once the coagulation cascade is triggered, activated factor X hydrolyses prothrombin to thrombin. Thrombin, for its part, triggers the formation of fibrin monomers by cleaving fibrinopeptide A and B (FpA and FpB) from the fibrinogen backbone. Fibrinogen is made up of 6 paired polypeptide chains $(A\alpha)_2$, $(B\beta)_2$, $\gamma_2$ and is 45 nm long. It is comprised of two outer D regions (each containing β- and γ-nodule) that are connected to the central E region by a coiled-coil segment. See MW Mosesson. "Fibrinogen and fibrin structure and functions," *Journal of Thrombosis and Haemostasis* 3.8 (2005), pp. 1894-1904.

However, the release of FpA exposes an α-chain motif GPR (Glycine-Proline-Arginine) called knob "A". Knob "A" binds to an exposed hole "a" in the globular γ-nodules of another fibrin monomer, resulting in a non-covalent knob-hole interaction. See Michael S Kostelansky et al. "2.8 Å crystal structures of recombinant fibrinogen fragment D with and without two peptide ligands: GHRP binding to the "b" site disrupts its nearby calcium-binding site," *Biochemistry* 41.40 (2002), pp. 12124-12132. The exposure of knob "A" is essential and also sufficient to form fibrin. See Artem Zhmurov et al. "Structural basis of interfacial flexibility in fibrin oligomers," *Structure* 24.11 (2016), pp. 1907-1917. The cleavage of FpB exposes a β-chain motif GHR (Glycine-Histidine-Arginine) called knob "B" that binds to its corresponding hole "b" (also non-covalently) in the globular β-nodule of another fibrin monomer. FpA cleavage is faster than FpB. See Harold A Scheraga and Michael Laskowski. "The fibrinogen-fibrin conversion," *Advances in protein chemistry* 12 (1957), pp. 1-131. Fibrin polymerization is initiated when two fibrin monomers form a half-staggered dimer. The monomers are hold together by the A:a knob-hole interaction of Knob "A" fitting into hole "a". The addition of a third fibrin molecule to the half-staggered dimer forms an end-to-end connection of two fibrin's lateral D regions. See Stephen J Everse et al. "Crystal structure of fragment double-D from human fibrin with two different bound ligands," *Biochemistry* 37.24 (1998), pp. 8637-8642. This weak D:D interface compromises the monomer junction in each of two fibrin oligomers. See John W Weisel and Rustem I Litvinov, "Mechanisms of fibrin polymerization and clinical implications," *Blood* 121.10 (2013), pp. 1712-1719. Other fibrin monomers can add longitudinally to the dimers to form longer oligomers. Two oligomer strands can then laterally interact. See WE Fowler et al. "Structure of the fibrin protofibril," *Proceedings of the National Academy of Sciences* 78.8 (1981), pp. 4872-4876. This interaction is mediated by the central E region of one fibrin monomer and two lateral D regions of two other fibrin molecules. The D-E-D structure is mainly held together by A-a knob-hole bonds.

Elongation of fibrin oligomers, results in the formation of protofibrils, which can associate with each other and aggregate laterally to form fibers. See Olga Kononova et al. "Molecular mechanisms, thermodynamics, and dissociation kinetics of knob-hole interactions in fibrin," *Journal of Biological Chemistry* 288.31 (2013), pp. 22681-22692. For the formation of a 3-dimensional fibrin network, it is necessary for the fibers to branch. See John W Weisel. "Fibrinogen and fibrin," *Advances in protein chemistry* 70 (2005), pp. 247-299. Furthermore, the fibrin network is covalently cross-linked by factor XIIIa, a plasma transglutaminase that is activated by thrombin in the presence of $Ca^{2+}$. This results in stabilization of the fibrin network. See Laszlo Lorand. "Factor XIII: structure, activation, and interactions with fibrinogen and fibrin," *Annals of the New York Academy of Sciences* 936.1 (2001), pp. 291-311.

In one embodiment, the CsgA is fused to a full-length fibrin. In one embodiment, the CsgA is fused to a subunit or a polypeptide chain of a fibrin (e.g., the α chain, γ chain or β chain of fibrin). In one embodiment, the CsgA is fused to a fragment or a motif of a subunit of a fibrin.

Sequences of exemplary fibrous proteins and fibrous protein subunits are listed in Table 1 below.

TABLE 1

Exemplary sequences of fibrous proteins, fragments, or motifs of fibrous proteins

| Fibrous Protein | Amino Acid Sequence | GenBank Accession No | SEQ ID NO |
|---|---|---|---|
| Keratin 5 (Homo Sapience) | MSRQSSVSFRSGGSRSFSTASAITPSVSRTSFTSVSRSGG GGGGGFGRVSLAGACGVGGYGSRSLYNLGGSKRISIST RGGSFRNRFGAGAGGGYGFGGGAGSGFGFGGGAGGG FGLGGGAGFGGGFGGPGFPVCPPGGIQEVTVNQSLLTPL NLQIDPSIQRVRTEEREQIKTLNNKFASFIDKVRFLEQQN KVLDTKWTLLQEQGTKTVRQNLEPLFEQYINNLRRQL DSIVGERGRLDSELRNMQDLVEDFKNKYEDEINKRTTA ENEFVMLKKDVDAAYMNKVELEAKVDALMDEINFMK MFFDAELSQMQTHVSDTSVVLSMDNNRNLDLDSIIAEV KAQYEEIANRSRTEAESWYQTKYEELQQTAGRHGDDL RNTKHEITEMNRMIQRLRAEIDNVKKQCANLQNAIADA EQRGELALKDARNKLAELEEALQKAKQDMARLLREY QELMNTKLALDVEIATYRKLLEGEECRLSGEGVGPVNI SVVTSSVSSGYGSGSGYGGGLGGGLGGGLGGGLAGGS SGSYYSSSSGGVGLGGGLSVGGSGFSASSGRGLGVGFG SGGGSSSSVKFVSTTSSSRKSFKS | AAF97931.1 | 2 |
| Keratin 14 (Homo Sapience) | MTTCSRQFTSSSSMKGSCGIGGGIGGGSSRISSVLAGGS CRAPSTYGGGLSVSSSRFSSGGAYGLGGGYGGGFSSSSS SFGSGFGGGYGGGLGTGLGGGFGGGFAGGDGLLVGSE KVTMQNLNDRLASYLDKVRALEEANADLEVKIRDWY QRQRPAEIKDYSPYFKTIEDLRNKILTATVDNANVLLQID NARLAADDFRTKYETELNLRMSVEADINGLRRVLDELT LARADLEMQIESLKEELAYLKKNHEEEMNALRGQVGG DVNVEMDAAPGVDLSRILNEMRDQYEKMAEKNRKDA EEWFFTKTEELNREVATNSELVQSGKSEISELRRTMQNL EIELQSQLSMKASLENSLEETKGRYCMQLAQIQEMIGSV EEQLAQLRCEMEQQNQEYKILLDVKTRLEQEIATYRRL LEGEDAHLSSSQFSSGSQSSRDVTSSSRQIRTKVMDVHD GKVVSTHEQVLRTKN | AAH94830.1 | 3 |

TABLE 1-continued

Exemplary sequences of fibrous proteins, fragments, or motifs of fibrous proteins

| Fibrous Protein | Amino Acid Sequence | GenBank Accession No | SEQ ID NO |
|---|---|---|---|
| Fibrinogen alpha subunit (Homo Sapience) | MFSMRIVCLVLSVVGTAWTADSGEGDFLAEGGGVRGP RVVERHQSACKDSDWPFCSDEDWNYKCPSGCRMKGLI DEVNQDFTNRINKLKNSLFEYQKNNKDSHSLTTNIMEIL RGDFSSANNRDNTYNRVSEDLRSRIEVLKRKVIEKVQHI QLLQKNVRAQLVDMKRLEVDIDIKIRSCRGSCSRALAR EVDLKDYEDQQKQLEQVIAKDLLPSRDRQHLPLIKMKP VPDLVPGNFKSQLQKVPPEWKALTDMPQMRMELERPG GNEITRGGSTSYGTGSETESPRNPSSAGSWNSGSSGPGS TGNRNPGSSGTGGTATWKPGSSGPGSTGSWNSGSSGTG STGNQNPGSPRPGSTGTWNPGSSERGSAGHWTSESSVS GSTGQWHSESGSFRPDSPGSGNARPNNPDWGTFEEVSG NVSPGTRREYHTEKLVTSKGDKELRTGKEKVTSGSTTT TRRSCSKTVTKTVIGPDGHKEVTKEVVTSEDGSDCPEA MDLGTLSGIGTLDGFRHRHPDEAAFFDTASTGKTFPGFF SPMLGEFVSETESRGSESGIFTNTKESSSHHPGIAEFPSR GKSSSYSKQFTSSTSYNRGDSTFESKSYKMADEAGSEA DHEGTHSTKRGHAKSRPVRGIHTSPLGKPSLSP | AAC97143.1 | 4 |
| Fibrinogen beta chain (Homo Sapience) | MKRMVSWSFHKLKTMKHLLLLLLCVFLVKSQGVNDN EEGFFSARGHRPLDKKREEAPSLRPAPPPISGGGYRARP AKAAATQKKVERKAPDAGGCLHADPDLGVLCPTGCQL QEALLQQERPIRNSVDELNNNVEAVSQTSSSSFQYMYL LKDLWQKRQKQVKDNENVVNEYSSELEKHQLYIDETV NSNIPTNLRVLRSILENLRSKIQKLESDVSAQMEYCRTPC TVSCNIPVVSGKECEEIIRKGGETSEMYLIQPDSSVKPYR VYCDMNTENGGWTVIQNRQDGSVDFGRKWDPYKQGF GNVATNTDGKNYCGLPGEYWLGNDKISQLTRMGPTEL LIEMEDWKGDKVKAHYGGFTVQNEANKYQISVNKYR GTAGNALMDGASQLMGENRTMTIHNGMFFSTYDRDN DGWLTSDPRKQCSKEDGGGWWYNRCHAANPNGRYY WGGQYTWDMAKHGTDDGVVWMNWKGSWYSMRKM SMKIRPFFPQQ | AAA18024.2 | 5 |
| Fibrinogen gamma chain (Homo Sapience) | MSWSLHPRNLILYFYALLFLSSTCVAYVATRDNCCILDE RFGSYCPTTCGIADFLSTYQTKVDKDLQSLEDILHQVEN KTSEVKQLIKAIQLTYNPDESSKPNMIDAATLKSRIMLEE IMKYEASILTHDSSIRYLQEIYNSNNQKIVNLKEKVAQLE AQCQEPCKDTVQIHDITGKDCQDIANKGAKQSGLYFIK PLKANQQFLVYCEIDGSGNGWTVFQKRLDGSVDFKKN WIQYKEGFGHLSPTGTTEFWLGNEKIHLISTQSAIPYALR VELEDWNGRTSTADYAMFKVGPEADKYRLTYAYFAGG DAGDAFDGFDFGDDPSDKFFTSHNGMQFSTWDNDND KFEGNCAEQDGSGWWMNKCHAGHLNGVYYQGGTYS KASTPNGYDNGIIWATWKTRWYSMKKTTMKIIPFNRLTI GEGQQHHLGGAKQAGDV | AAB59531.1 | 6 |
| Elastin (Homo Sapience) | MAGLTAAAPRPGVLLLLLSILHPSRPGGVPGAIPGGVPG GVFYPGAGLGALGGGALGPGGKPLKPVPGGLAGAGLG AGLGAFPAVTFPGALVPGGVADAAAAYKAAKAGAGLG GVPGVGGLGVSAGAVVPQPGAGVKPGKVPGVGLPGV YPGGVLPGARFPGVGVLPGVPTGAGVKPKAPGVGGAF AGIPGVGPFGGPQPGVPLGYPIKAPKLPGGYGLPYTTGK LPYGYGPGGVAGAAGKAGYPTGTGVGPQAAAAAAAK AAAKFGAGAAGVLPGVGGAGVPGVPGAIPGIGGIAGV GTPAAAAAAAAAKAAKYGAAAGLVPGGPGFGPGVV GVPGAGVPGVGVPGAGIPVVPGAGIPGAAVPGVVSPEA AAKAAAKAAKYGARPGVGVGGIPTYGVGAGGFPGFG VGVGGIPGVAGVPSVGGVPGVGGVPGVGISPEAQAAA AAKAAKYGVGTPAAAAAKAAAKAAQFGLVPGVGVAP GVGVAPGVGVAPGVGLAPGVGVAPGVGVAPGIGPVAPG IGPGGVAAAAKSAAKVAAKAQLRAAAGLGAGIPGLGV GVGVPGLGVGAGVPGLVGAGVPGFGAGADEGVRRS LSPELREGDPSSQHLPSTPSSPRVPGALAAAKAAKYGA AVPGVLGGLGALGGVGIPGGVVGAGPAAAAAAAKAA AKAAQFGLVGAAGLGGLGVGGLGVPGVGGLGGIPPAA AAKAAKYGAAGLGGVLGGAGQFPLGGVAARPGFGLSP IFPGGACLGKACGRKRK | AAC98395.1 | 7 |
| Collagen (Homo Sapience) | MHPGLWLLLVTLCLTEELAAAGEKSYGKPCGGQDCSG SCQCFPEKGARGRPGPIGIQGPTGPQGFTGSTGLSGLKG ERGFPGLLGPYGPKGDKGPMGVPGFLGINGIPGHPGQP GPRGPPGLDGCNGTQGAVGFPGPDGYPGLLGPPGLPGQ KGSKGDPVLAPGSFKGMKGDPGLPGLDGITGPQGAPGF | BAA04809.1 | 8 |

TABLE 1-continued

Exemplary sequences of fibrous proteins, fragments, or motifs of fibrous proteins

| Fibrous Protein | Amino Acid Sequence | GenBank Accession No | SEQ ID NO |
|---|---|---|---|
| | PGAVGPAGPPGLQGPPGPPGPLGPDGNMGLGFQGEKGV KGDVGLPGPAGPPPSTGELEFMGFPKGKKGSKGEPGPK GFPGISGPPGFPGLGTTGEKGEKGEKGIPGLPGPRGPMG SEGVQGPPGQQGKKGTLGFPGLNGFQGIEGQKGDIGLP GPDVFIDIDGAVISGNPGDPGVPGLPGLKGDEGIQGLRG PSGVPGLPALSGVPGALGPQGFPGLKGDQGNPGRTTIG AAGLPGRDGLPGPPGPPGPPSPEFETETLHNKESGFPGL RGEQGPKGNLGLKGIKGDSGFCACDGGVPNTGPPGEPG PPGPWGLIGLPGLKGARGDRGSGGAQGPAGAPGLVGPL GPSGPKGKKGEPILSTIQGMPGDRGDSGSQGFRGVIGEP GKDGVPGLPGLPGLPGDGGQGFPGEKGLPGLPGEKGHP GPPGLPGNGLPGLPGPRGLPGDKGKDGLPGQQGLPGSK GITLPCIIPGSYGPSGFPGTPGFPGPKGSRGLPGTPGQPGS SGSKGEPGSPGLVHLPELPGFPGPRGEKGLPGFPGLPGK DGLPGMIGSPGLPGSKGATGDIFGAENGAPGEQGLQGL TGHKGFLGDSGLPGLKGVHGKPGLLGPKGERGSPGTPG QVGQPGTPGSSGPYGIKGKSGLPGAPGFPGISGHPGKKG TRGKKGPPGSIVKKGLPGLKGLPGNPGLVGLKGSPGSP GVAGLPALSGPKGEKGSVGFVGFPGIPGLPGISGTRGLK GIPGSTGKMGPSGRAGTPGEKGDRGNPGPVGIPSPRRP MSNLWLKGDKGSQGSAGSNGFPGPRGDKGEAGRPGPP GLPGAPGLPGIIKGVSGKPGPPGFMGIRGLPGLKGSSGIT GFPGMPGESGSQGIRGSPGLPGASGLPGLKGDNGQTVEI SGSPGPKGQPGESGFKGTKGRDGLIGNIGFPGNKGEDG KVGVSGDVGLPGAPGFPGVAGMRGEPGLPGSSGHQGA IGPLGSPGLIGPKGFPGFPGLHGLNGLPGTKGTHGTPGP SITGVPGPAGLPGPKGEKGYPGIGIGAPGKPGLRGQKGD RGFPGLQGPAGLPGAPGISLPSLIAGQPGDPGRPGLDGE RGRPGPAGPPGPPGPSSNQGDTGDPGFPGIPGFSGLPGEL GLKGMRGEPGFMGTPGKVGPPGDPGFPGMKGKAGAR GSSGLQGDPGQTPTAEAVQVPPGPLGLPGIDGIPGLTGD PGAQGPVGLQGSKGLPGIPGKDGPSGLPGPPGALGDPG LPGLQGPPGFEGAPGQQGPFGMPGMPGQSMRVGYTLV KHSQSEQVPPCPIGMSQLWVGYSLLFVEGQEKAHNQD LGFAGSCLPRFSTMPFIYCNINEVCHYARRNDKSYWLST TAPIPMMPVSQTQIPQYISRCSVCEAPSQAIAVHSQDITIP QCPLGWRSLWIGYSFLMHTAAGAEGGGQSLVSPGSCLE DFRATPFIECSGARGTCHYFANKYSFWLTTVEERQQFGE LPVSETLKAGQLHTRVSRCQVCMKSL | | |

In one embodiment, the fibrous protein may comprise any of the fibrous protein sequences disclosed herein. In one embodiment, the fibrous protein may consist of any of the fibrous protein sequences disclosed herein. In one embodiment, the fibrous protein may have at least 80%, at least 85%, at least 90%, at least 95%, at least 96%, at least 97%, at least 98%, or at least 99% sequence identity to any of the fibrous protein sequences disclosed herein.

Using genetically modified bacteria (e.g., *E. coli*) comprising CsgA-fibrous protein fusions described herein, a fibrous proteinaceous network can be formed. For example, a proteinaceous network described herein may comprise more than one type of curli fiber, each comprising a CsgA protein fused to a different fibrous protein, wherein a first CsgA fusion comprises a first fibrous protein non-covalently bound to a second fibrous protein of a second CsgA fusion, to form fibrous structures and proteinaceous networks.

In one embodiment, the fibrous proteinaceous network described herein comprises a first curli fiber wherein the CsgA protein is fused to a K5 keratin and a second curli fiber wherein the CsgA protein is fused to a K14 keratin, wherein the K5 protein is non-covalently bound to the K14 protein to form a fibrous structure and a proteinaceous network. In one embodiment, the K5 protein comprises the polypeptide of SEQ ID NO:11. In one embodiment, the K14 protein comprises the polypeptide of SEQ ID NO:12.

In one embodiment, the fibrous proteinaceous network described herein comprises a first curli fiber wherein the CsgA protein is fused to the α chain (or a fragment or motif) of a fibrin and a second curli fiber wherein the CsgA protein is fused to a γ chain (or a fragment or motif) of a fibrin, wherein the α chain motif is non-covalently bound to the γ chain motif to form a fibrous structure and a proteinaceous network. In one embodiment, the α chain motif of fibrin is Knob "A". In one embodiment, the α chain motif of fibrin is the polypeptide of SEQ ID NO:9. In one embodiment, the γ chain motif of fibrin is hole "a". In one embodiment, the γ chain motif of fibrin is the polypeptide of SEQ ID NO:10.

Hydrogels

In one aspect, provided herein is a method of making a biologic hydrogel comprising contacting a liquid composition comprising a bacterial cell that expresses a curli fiber with a solubilization agent, thereby creating a mixture; contacting the mixture with a filter; contacting the mixture with a surfactant; incubating the mixture, thereby allowing the mixture to gelate; and concentrating the mixture using filtration; thereby making the biologic hydrogel.

In some embodiments, the solubilization agent can be a denaturing solubilization agent, a non-denaturing solubilization agent, or a mild denaturing solubilization agent. In some embodiments, the solubilization agent can be, but is not limited to, guanidine, urea, DMSO, SDS, β-mercaptoethanol, or n-propanol. In some embodiments, the solubilization agent is any agent or reagent capable of inducing lysis of a microbial cell (e.g., a bacterial cell) including a lysis buffer, lysozyme, a base such as sodium hydroxide, and others. The concentration of the solubilization agent that is used may be varied, and without wishing to be bound by any particular theory, may affect the purity of the amyloid fibers that are ultimately obtained using the methods described herein. In some embodiments, the solubilization agent is used at a concentration capable of inducing lysis of a bacterial cell. One of ordinary skill may readily ascertain the concentration of the solubilization agent necessary in order to induce lysis of a bacterial cell. For example, when guanidine hydrochloride (GdmCl) is the solubilization agent that is used in the methods described herein, the concentration of guanidine hydrochloride may range from 0.1-10 M. In some embodiments, the concentration of guanidine hydrochloride is about 0.1 M, about 0.2 M, about 0.3 M, about 0.4 M, about 0.5 M, about 0.6 M, about 0.7 M, about 0.8 M, about 0.9 M, about 1 M, about 2 M, about 3 M, about 4.0 M, about 5.0 M, about 6.0 M, about 7.0 M, about 8.0 M, about 9.0 M, about 10.0 M, or more.

In some embodiments, the methods described herein may be performed using vacuum filtration (e.g., using vacuum generated with a pump). In some embodiments, the methods described herein may be performed using gravity filtration. In some embodiments, the methods described herein may be performed using centrifugal filtration. In some embodiments, the methods described herein may be performed using filter plates for small scale purification. The filtration set-ups used in the methods described herein may include vacuum filtration holders, butchner funnels, tabletop filtration systems, and the like.

In some embodiments, the filter is a filter membrane, a mesh, or a porous cloth. In one embodiment, the filter membrane is polycarbonate, nylon, cellulose, polytetrafluoroethylene (Teflon™), polyethersulfone, polyvinylidene fluoride, or polyvinylidene chloride. In one embodiment, the filter membrane is a hydrophilic nylon net. In one embodiment, the mesh is a metal mesh, a glass mesh, a ceramic mesh, a plastic mesh, or a polymer mesh.

In some embodiments, the filter membranes used in the presently disclosed methods may be, but are not limited to, polymer membranes made of polycarbonate, nylon, cellulose, Teflon™, polyethersulfone, polyvinylidene fluoride, polyvinylidene chloride, or other materials. In some embodiments, curli fiber aggregates can be filtered on cloths, or any other fabrics with pores of the appropriate size, as described herein. In some embodiments, curli fiber aggregates can be filtered on porous mesh with pores of the appropriate size, as described herein, such as, but not limited to, metal meshes, plastic meshes, glass meshes, ceramic meshes, or polymer meshes.

The filter membranes can have a pores of any shape or geometry. For example, in some embodiments, the pores can be circular. In other embodiments, the pores can be mesh-like. In some embodiments, the filter membranes can have pores of more than one shape or geometry.

The filter membrane may be of any geometric (e.g., circular, octagonal, rectangular, squared) or non-structured shape. The filter membrane may be of any size. For example, larger filters allow for scaling-up of the purification process.

In some embodiments, the surfactant can be an ionic surfactant or a non-ionic surfactant. In some embodiments, the surfactant can be, but is not limited to, SDS, 4-octylphenol polyethoxylate (also known as Triton X-100™), polyethylene glycol sorbitan monolaurate (also known as Tween™ 20), polyethylene glycol sorbitan monooleate (also known as Tween™ 80). For example, when the surfactant is SDS, a solution comprising 1% (w/v), 2%, 3%, 4%, 5%, 6%, 7%, 8%, 9%, 10% or more may be used. In some embodiments, the surfactant is SDS at a concentration of 5% (w/v).

In some embodiments, the methods further comprising air-drying the biologic hydrogel. In some embodiments, the air-drying is performed at room temperature for at least 2 hours, at least 3 hours, at least 4 hours, at least 5 hours, at least 6 hours, at least 12 hours, at least 24 hours, at least 36 hours, or more.

In some embodiments, the method further comprises dehydrating the biologic hydrogel. In some embodiments, the method further comprises rehydrating the biologic hydrogel.

In some embodiments, the method further comprises imprinting the surface of the biologic hydrogel with a mold. In some embodiments, the mold is a nano mold. In some embodiments, the mold is a micro mold. In some embodiments, the mold comprises a pattern (e.g., a mesh or a structured surface). In some embodiments, the mold is a naturally occurring material.

In some embodiments, the filter membranes may be, but are not limited to, polymer membranes made of polycarbonate, nylon, cellulose, Teflon, polyethersulfone, polyvinylidene, fluoride, Polyvinylidene chloride, or other materials (e.g., chitin, chitosan, alginate). In some embodiments, the filter membrane can have pores of any size larger than the size of a bacterium and smaller than the size of an aggregate of curli fibers (approximately ~2 to 50 μm).

The methods described herein may be performed at a small scale (i.e., as a batch process) or may be adapted for large scale production of hydrogels.

In some embodiments, the hydrogel comprises a fibrous proteinaceous network. In some embodiments, the hydrogel can be used as an ink for 3D printing.

Methods and Uses

Disclosed herein is a versatile platform to create fibrous proteinaceous network of the extracellular matrix of bacteria, e.g., *E. coli*. Fibrous proteins, e.g., keratin and fibrin, fused to the curli fibers are immobilized site-specifically onto a biofilm surface, for example, with no need of any protein purification. Additionally, the fibrous proteinaceous networks, are formed in a self-assembling manner, for example, where no additional chemical conjugation is needed. The engineered biofilm is capable of forming and retaining a fibrous proteinaceous network.

The compositions and methods described herein are useful in various applications. By resembling mechanic and rheological properties of fibrous proteins, the proposed system would be biocompatible and have a wide range of applications in the fields of biomedical engineering and tissue engineering. Because of the stiffness and viscosity of the hydrogel produced, it could be used for instance as inks for three-dimensional printing (3D printing). Furthermore, the hydrogels can behave as a viscoelastic glue that has the potential to function as a tissue sealant like fibrin glue.

3D-Printing Inks

The fibrous proteinaceous networks, biofilms, hydrogels or biomaterials of the current invention can be used as inks for three-dimensional printing (3D printing). In some embodiments, the 3D-printing inks, e.g., bacto-inks, or BactoPrinks can further comprise a functional curli fiber or an engineered microbial cell, e.g., a bacterium that expresses one or more functional curli fibers. In some embodiments, a functional curli fiber is a fusion protein of CsgA linked to a non-native functional polypeptide. In some embodiments, the CsgA protein is linked to the non-native functional polypeptide by a linker.

In some embodiments, the bacto-inks of the invention comprises a fibrous proteinaceous network, biofilm, hydrogel or biomaterial of the current invention and is further mixed and contacted with a functional curli fiber. In some embodiment, the functional curli fiber is an isolated curli fiber. In some embodiments, the bacto-inks of the invention comprises a fibrous proteinaceous network, biofilm, hydrogel or biomaterial of the current invention and is further mixed and contacted with an engineered microbial cell, e.g., a bacterium that express a functional curli fiber. In some embodiments, the engineered bacterium comprises a nucleotide encoding the functional curli fiber.

As used herein, a functional polypeptide includes a polypeptide having an activity or function, such that when it is present in a biofilm, it confers upon the biofilm a property, function, or activity which it did not have in the absence of the activity of the polypeptide. Accordingly, an activity polypeptide can be, e.g. an enzyme, a polypeptide that binds another molecule, a binding domain, a peptide that is bound by another molecule (e.g. a ligand or epitope), or the like. Examples of polypeptides for use as activity polypeptides include, but are not limited to bisphenol A (BPA) binding domain, Metal binding domain (MBD); SpyTag; graphene binding (GBP); carbon nanotube binding (CBP); gold binding (A3); CT43; FLAG; Z8; E14; QBP1; CLP12; and AFP8. In some embodiment, the non-native functional polypeptide is a therapeutic polypeptide, a diagnostic polypeptide, a tissue-binding polypeptide, a cell-binding polypeptide, an antimicrobial polypeptide, an anticancer polypeptide, an anti-inflammatory polypeptide, a polymer binding polypeptide, a metabolite binding polypeptide, a targeting polypeptide or a polypeptide that is a first pair of a binding pair of molecules. In some embodiments, the non-native functional polypeptide is not a fibrous protein, or a fragment thereof, that is contained in the amyloid fusion protein, or the fibrous proteinaceous network disclosed in the previous sections of current disclosure. In some embodiments, the functional curli fibers or engineered bacteria that produce the functional curli fibers are added to the bacto-ink in addition to the fibrous proteinaceous network, biofilm, hydrogel or biomaterial described in the previous sections of the current disclosure.

According to certain aspects, the functional polypeptide when present as part of an engineered CsgA polypeptide, is functional. A polypeptide is said to be "functional" or expressed as a "functional" polypeptide if the polypeptide retains at least about 50% of the activity (e.g. enzymatic activity or binding activity) that it has as an isolated polypeptide. One of skill in the art can readily detect increases in reaction products and/or detect decreases in reaction substrates, e.g. by mass spectroscopy (MS, including, e.g., MADLI/TOF, SELDI/TOF, LC-MS, GC-MS, HPLC-MS, etc., among others) or detect increases or decrease in binding to a binding partner, e.g. by immunoassays. In some embodiments, a functional activity polypeptide can retain at least 50% of the activity of the isolated polypeptide, e.g. 50% or more of the activity, 60% or more of the activity, 75% or more of the activity, or 90% or more of the activity of the isolated polypeptide.

Exemplary functional polypeptides and methods of making an engineered bacterium that expresses a fusion protein of CsgA with a non-native functional polypeptide are disclosed in, e.g., U.S. Patent No. US 2018/0258435 A1, and U.S. Pat. No. 9,815,871, the entire content of each is hereby incorporated by reference.

In some embodiments, the bacto-ink disclosed herein is capable of self-regeneration due to the existence of live bacteria that produce the fibrous proteinaceous networks, biofilms, hydrogels or biomaterials. In some embodiment, the bacto-ink disclosed herein is capable of self-regeneration due to the existence of live bacteria that produce the functional curli fibers comprising the fusion protein of CsgA and the non-native functional polypeptide.

In one aspect, the composition and methods described herein can be used as a novel material for 3D printing. In some embodiments, the composition and methods are used as biocompatible materials for tissue engineering, such as tissue sealant. In some embodiments, the composition and methods are used in medical procedures such as bone replacement.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

EXAMPLES

The following examples are set forth as being representative of the present disclosure. These examples are not to be construed as limiting the scope of the present disclosure as these and other equivalent embodiments will be apparent in view of the present disclosure, figures and accompanying claims.

Unless otherwise stated, the present invention was performed using standard procedures, as described, for example in Sambrook et al., Molecular Cloning: A Laboratory Manual (3 ed.), Cold Spring Harbor Laboratory Press, Cold Spring Harbor, N.Y., USA (2001); Davis et al., Basic Methods in Molecular Biology, Elsevier Science Publishing, Inc., New York, USA (1995); or Methods in Enzymology: Guide to Molecular Cloning Techniques Vol. 152, S. L. Berger and A. R. Kimmel Eds., Academic Press Inc., San Diego, USA (1987); and Current Protocols in Protein Science (CPPS) (John E. Coligan, et. al., ed., John Wiley and Sons, Inc.), which are all incorporated by reference herein in their entireties.

Example 1: Background and Introduction

Curli fibers can constitute up to 40% of the biomass of many biofilms and can therefore be engineered to create a biofilm, expressing the added functionalization in a large portion of the resulting engineered biofilm. *E. coli* derived curli fibers are one of the most studied type of amyloids which is therefore an advantage in comparison with other, less known types of amyloids produced by many other bacteria.

BIND works by exploiting this system. A laboratory strain of *E. coli* containing a deletion of the CsgA gene (*E. coli* ΔcgsA) is transformed with a plasmid encoding an engineered version of the CsgA protein, which can be functionalized in a variety of ways by fusing different peptide domains (Nguyen et al., *Nature Communications*, 5, 4945, 2014). In other words, the CsgA protein can be engineered in order to display different types of coating treatments. It represents an easier and more flexible method compared to engineering the exopolysaccharide part of the biofilm, something that would require a multiple step pathway and which would have less chemical tolerance.

By genetic engineered biofilm matrix proteins of *E. coli* bacteria, it was possible to mimic prominent fibrous proteinaceous networks in the human body. It was hypothesized that through integration of engineered ECM of two reprogrammed cell lines, proteins derived from fibrous proteins such as fibrin or keratin displayed on curli fibers will be able to interact and aggregate to form the novel network. As for fibrin, the natural occurring network is imitated by the interaction of fused "α" and "γ", and therefore by the knob-hole bond. The coiled-coil structure in natural fibrin is replaced by CsgA that acts as the backbone for "α" and "γ". The same principal applies for keratin. Here the direct interaction of fused "K5" and "K14" onto curli fibers will form the coiled-coil heterodimers.

Example 2: Materials and Methods

Cell Strains, Plasmids and Reagents

The genes encoding CsgA-α, CsgA-γ, CsgA-K5 and CsgA-K14 were synthesized (Integrated DNA Technologies) and cloned by overlap extension into pET21d vectors consisting of the csgACEFG operon under the control of the T7 promoter (see Table 2 for sequences). All cloning was performed using isothermal Gibson Assembly cloning Kit®, and verified by DNA sequencing. (Dorval Courchesne et al., *ACS Biomaterials Science & Engineering*, acsbiomaterials.6b00437, 2016), with a single operon, csgBACEFG, under the control of the T7 promoter, where the nucleator protein CsgB, responsible for connecting curli fibers to the external surface of the bacteria, was deleted. This plasmid was created using the two divergent operons regions, the csgBAC and csgEFG, which were PCR isolated from the W3110 strain of *E. coli* K12 and cloned by overlap extension into the pET21d plasmid.

TABLE 2

Plasmids

| Plasmid Name | Description | Reference |
| --- | --- | --- |
| pET21d-CsgA | Curli operon regions consisting of csgBAC and csgEFG were PCR isolated from *E. coli* K12 substr. W3110 and cloned by overlap extension into the pET21d plasmid, to create a single operon, csgBACEFG, under the control of the T7 promoter. AmpR | (Dorval Courchesne et al., 2016) |
| pET21d-CsgA-α | Fusion of csgA to partial fibrinogen α subunit gene. Under control of the T7 promoter. AmpR. Amino acid sequence of fibrinogen α insertion: GPRVVERHQSA (SEQ ID NO: 9) | |
| pET21d-CsgA-γ | Fusion of csgA to partial fibrinogen γ subunit gene. Under control of the T7 promoter. AmpR. Amino acid sequence of fibrinogen γ insertion: DAGDAFDGFDFGDDPSDKFFTSHNGMQFSTW DNDNDKFEGNCAEQDGSGWWMNKCHAGHL NGVYYQGGTYSKASTPNGYDNGIIWATWKTR WYSMKKTTMKIIPFNRLTIGEGQQHHLGGAKQ AGDVWDNDNDKFEGNCAEQDGSGWWMNKC HAGHLNGVYYQGGTYSKASTPNGYDNGIIWA TWKTRWYSMKKTTMKIIPFNRLTIGEGQQHHL GGAKQAGDV (SEQ ID NO: 10) | |
| pET21d-CsgA-K5 | Fusion of csgA to partial keratin 5 gene. Under control of the T7 promoter. AmpR. Amino acid sequence of keratin 5 insertion: ANRSRTEAESWYQTKYEELQQTAGRHGDDLR NTKHEISEMNRMIQRLRAEIDNVKKQCANLQN AIADAEQRGELALKDARNKLAELEEALQKAK QDMARLLREYQELMNTKLALDVEIATYRKLL EGEECR (SEQ ID NO: 11) | |

TABLE 2-continued

Plasmids

| Plasmid Name | Description | Reference |
|---|---|---|
| pET21d-CsgA-K14 | Fusion of csgA to partial keratin 14 gene. Under control of the T7 promoter. AmpR. Amino acid sequence of keratin 14 insertion: AEKNRKDAEEWFFTKTEELNREVATNSELVQS GKSEISELRRTMQNLEIELQSQLSMKASLENSL EETKGRYCMQLAQIQEMIGSVEEQLAQLRCEM EQQNQEYKILLDVKTRLEQEIATYRRLLEGED (SEQ ID NO: 12) | |

The fusion expression of α, γ, K5 and K14 onto curli fibers was performed in a curli operon deletion mutant of an *E. coli* strain, PQN4. The PQN4 is an *E. coli* strain derived from LSR10 (MC4100, ΔCsgA, λ(DE3), CamR) which was constructed to knockout the curli operon. Table 3 provides a list of bacterial strains used in the Examples.

TABLE 3

Bacterial Strains

| Strain Designation | Genotype | Notes | References |
|---|---|---|---|
| PQN4 | LSR10 (MC4100, ΔCsgA, λ(DE3), CamR) T7RNAP | Used for protein expression of all enzyme constructs and biofilm experiments | (Dorval Courchesne et al., 2016) |

Bacteria Cultivation and Curli Fiber Expression

300 µl of cloned PQN4 cells carrying the engineered plasmids, were seeded onto lysogeny broth (LB) agar plates containing 2% glucose and 100 µg/ml of carbenicillin. The bacteria were incubated over night at 37° C. The settled plates were stored upside down in a refrigerator at 4° C. for a maximum of two weeks. Inoculation of the reprogrammed bacteria cultures was performed using a 1:10:1000 mixture of LB, 20% (v/v) glucose and 98% (v/v) carbenicillin. 5 ml of this mixture were filled into a tube.

For the expression of a single protein, a reprogrammed bacterial colony was loaded onto a tip of a pipette and put into a falcon tube along with the antibiotic and glucose containing mixture. The tubes were then incubated for four to six hours or overnight in a shaking incubator at 37° C. and 225 revolutions per minute (rpm). Next, the content of each tube was transferred into a 1 L flask with a growth medium containing 500 ml LB and 5 µl carbenicillin (98% (v/v)). Incubation for 48 hours in a shaking incubator at 37° C. and 225 rpm to allow fiber expression was performed next. For the expression of two proteins simultaneously (referred as co-culturing), i.e., K5 and K14, the reprogrammed bacterial colonies were each loaded onto a tip of a pipette and then put into separate tubes containing 2.5 ml of the antibiotic and glucose containing mixture. The tubes were then incubated for four to six hours or overnight in a shaking incubator at 37° C. and 225 rpm. Then two tubes of the reprogrammed bacteria expressing the corresponding proteins were transferred into the same 1 L flask containing 500 ml of LB and 5 µl carbenicillin (98% (v/v)). The flasks were then incubated for 48 hours in a shaking incubator at 37° C. and 225 rpm to allow fiber expression.

Quantitative Congo Red (CR) Amyloid Staining

Congo Red (CR) binding assay was adapted from previously published methods, see Chapman, M. R. et al. Role of *Escherichia coli* curli operons in directing amyloid fiber formation. *Science* 295, 851-855 (2002).

Proteinaceous Network Formation

Two different ways of creating a novel network by the interaction of fibrin and keratin derived proteins fused onto curli were established. One is to have two reprogrammed bacteria cultures, each expressing one matching protein fused onto curli for 48 hours. Then, these two cultures are mixed together and incubated for additionally two hours to allow interaction of the matching fibrin or keratin derived proteins. The other method is to co-culture two reprogrammed bacteria in the same flask for 48 hours. This way a heterogeneous expression pattern occurs of interacting proteins displayed onto curli fibers. This facilitates interaction of the matching proteins to mimic the fibrin or keratin network. Both methods, mixing and co-culturing, resulted in successful fiber aggregates, thus, to formation of the novel networks, as further illustrated and explained in the following sections and subsections.

Aggregation of Engineered Curli Fibers

Figure 1B:
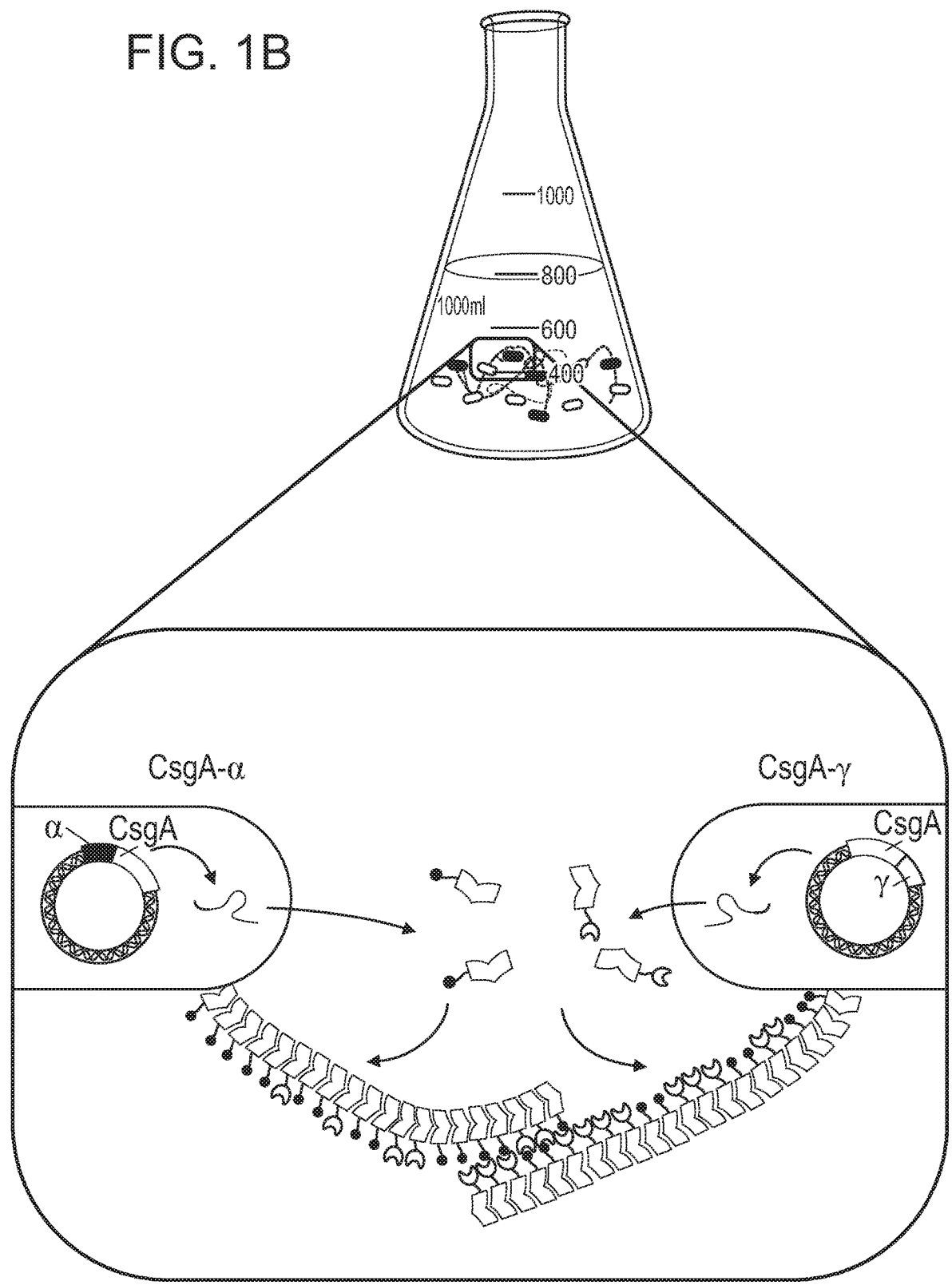

After 48 hours of curli fiber expression, two cultures expressing the matching proteins, i.e., K5 and K14 separately, were put together in a 2 L flask. The flasks were then mixed together and placed for two hours into a shaking incubator at 37° C. and 225 rpm to achieve fiber aggregation through interaction of the fused proteins onto curli. This method is referred as mixed culture. For the co-cultured bacteria expressing the matching proteins simultaneously in the same 1 L flask for 48 hours, additional mixing time of two hours was not required, since the proteins were already able to interact together. The cultures of only one expressed protein, and the mixed and co-cultured bacteria were then viewed under a bright-field microscope to see and compare fiber aggregation at a magnification of 4×, 10×, 20× and 50×. Before the examination, the cells were concentrated by factor 20 and 50 for better visualization of the fibers. This was done by spinning down the culture at 6000 rpm for 10 minutes and replacement of the supernatant with DI water, i.e., for 500 ml of bacterial culture the cells were resuspended in 25 ml of DI water to achieve a 20 times higher concentration. FIGS. 1A and 1B depict the two methods used for fiber aggregation.

Hydrogel Fabrication

The cultures expressing the engineered curli fibers were incubated with guanidine hydrochloride (GdmCl; Sigma-Aldrich, G4630, ≥98%), at final concentration of 0.8M at 4° C. for maximal one hour. After incubation, the culture was transferred onto a hydrophilic nylon net filter membrane with 11 µm pore size (Millipore Sigma) of 47 mm diameter, via vacuum filtration. The amount of transferred culture varied between 17 ml to 70 ml, depending when the filters got partially clogged. To remove living bacteria, the filter membrane was incubated with 5 ml of 8M GdmCl for 5 minutes, followed by vacuum filtration of the liquid. Next, the bacterial biofilm was washed three times with 25 ml of sterile DI water. Then, the cultures on the filter membrane were treated with 5 ml of 0.01% (v/v) concentration of Benzonase® nuclease (Sigma-Aldrich, 1.5 Um') for 5 minutes to remove DNA and RNA bound to curli fibers. Finally, the semi-purified bacteria-free fibers were incubated with 5 ml of 5% (m/v) SDS in sterile water for 5 minutes. After vacuum filtration of the liquid, the filtered fibers on the membrane were washed three times with minimum 25 ml DI water. The bacteria-free hydrogel was scrapped off the filter membranes and stored in small tube at 4° C.

Scanning Electron Microscopy (SEM)

I. SEM of Bacterial Cultures

200 µl of genetically engineered bacterial culture for each functional group was vacuum filtered onto nuclepore filters (0.22 µm pore size; GE Healthcare Bio-Sciences), rinsed, and fixed with 2% formaldehyde and 2% glutaraldehyde solution overnight at 4° C. Then, the samples were washed with Millipore water for 15 minutes and dehydrated with gradient steps of increasing ethanol (EtOH) concentrations (25%, 50%, 75%, 100%, 100% (v/v)). Each step takes 15 minutes of incubation time. The samples were dried with Critical Point Dryer (Autosamdri®-931, Tousimis®). Finally, the samples were sputter coated with a platin: paladiumalloy in the ratio of 80:20. The samples were analyzed using a Zeiss Supra55VP FE-SEM.

II. SEM of Curli Based Hydrogels

The hydrogel samples were prepared for SEM by fixing the gels with 2 m/v % glutaraldehyde and 2 m/v % paraformaldehyde in 0.1 of 0.1 M (n/V) sodium cacodylate buffer for a minimum of 2 hours at room temperature (RT). Then, the gels were gently washed with Millipore water. The solvent for every sample was gradually exchanged with increasing EtOH concentrations (25%, 50%, 75% and 100% (v/v)), with an incubation time of 15 minutes respectively. The gels were dried in a critical point dryer, placed onto SEM sample holders using silver adhesive (Electron Microscopy Sciences), and sputtered until they were coated in a 5 nm layer of Pt/Pd. Imaging was performed using a Zeiss Ultra 55 Field Emission SEM.

Rheology

The mechanical properties of the different hydrogel samples were determined using a Discovery Hybrid Rheometer-3 and TRIOS software (TA Instruments, New Castle, DE). Samples were loaded between peltier plate bottom and 20 mm steel top plate geometry with the gap set to be 500 µm. To prevent distortion, a homogeneous mass of the hydrogels has to be ensured. During production of the gels air bubbles can occur. Removal was achieved by applying either vacuum or by centrifuging. The sample size was approximately 200 µl. The excess hydrogel was trimmed along the edge of the 20 mm top plate. Samples were then surrounded with mineral oil to prevent dehydration. For each hydrogel group three replicate samples were tested independently. Time sweep experiments were conducted under continuous oscillations at 0.1 Hz with an imposed shear strain of 0.5% to measure the linear shear modulus.

Example 3: Fibrous Network Expression and Hydrogel Characterization

Fiber Expression

To determine curli expression of the reprogrammed bacteria, a specific amyloid protein dye called Congo red was used. Congo red binds amyloid proteins like CsgA with high specificity. See Anne K Schütz et al. "The amyloid-Congo red interface at atomic resolution," *Angewandte Chemie International Edition* 50.26 (2011), pp. 5956-5960. Red staining indicates the production of curli and therefore confers the expression of the fused proteins onto CsgA.

Network Formation

Figure 2C:
FIGS. 2A, 2B, 2C, 2D, 2E, and 2F depict fibrin fiber aggregation of mixed and co-cultured method. All bacteria were expressing fibers for 48 hours in a shaking incubator for 48 hours, at 37° C. and 225 rpm. Bacterial ECM displaying CsgA-α or CsgA-γ alone shows little aggregation of only CsgA-α fibers (FIG. 2A) or little aggregation of only CsgA-γ fibers (FIG. 2B). Bacterial ECM displaying CsgA-$αγ_{mixed}$ shows dense fiber aggregation of CsgA-$αγ_{mixed}$ fibers (FIGS. 2C-2E). Bacterial ECM displaying CsgA-$αγ_{co-cultured}$ shows higher fiber aggregation of CsgA-$αγ_{co-cultured}$ fibers after 48 hours (FIG. 2F).
Figure 2F:
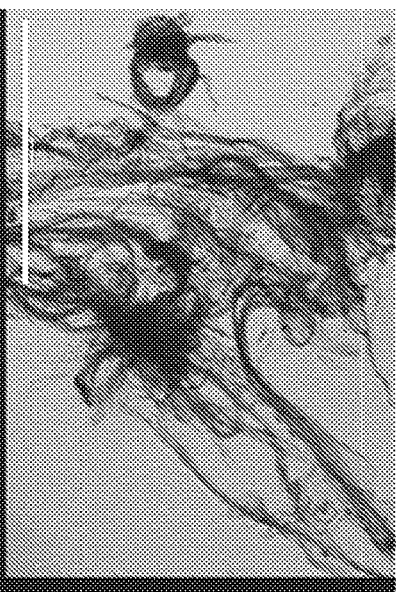
Figure 2B:
Figure 2E:
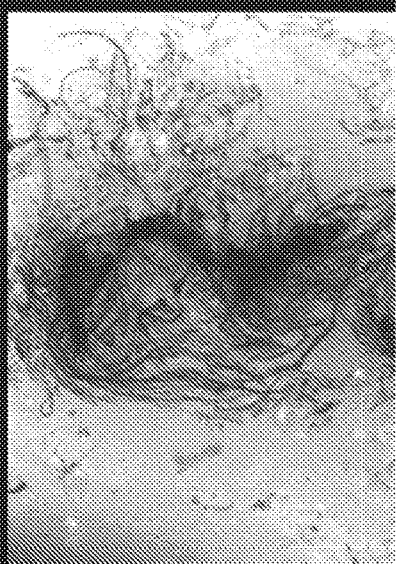
Figure 2A:
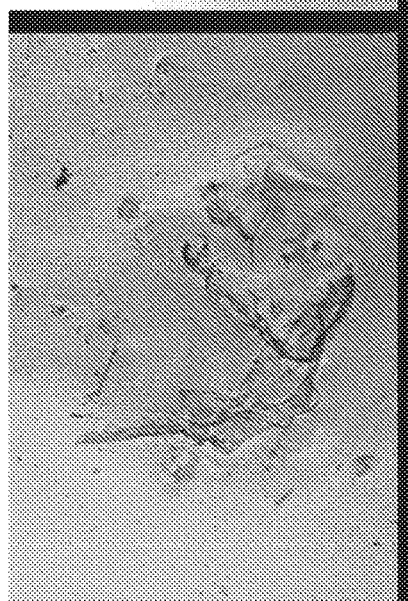
Figure 2D:
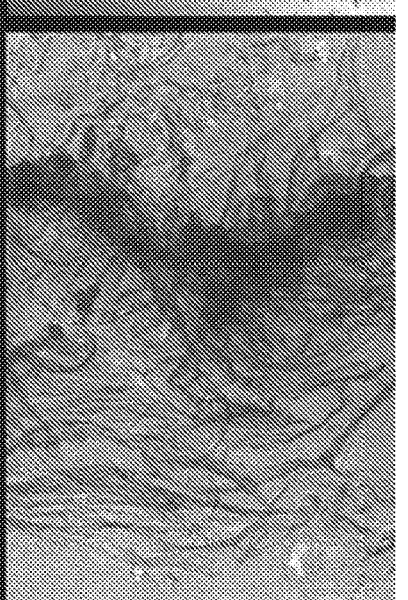

Under a conventional bright-field microscope the ECM of reprogrammed bacteria with fibrin and keratin derived proteins were viewed and compared. The ECM of bacterial culture displaying protein α and γ together (referred as CsgA-αγ based ECM), through either mixing (referred as CsgA-αγ$_{mixed}$) (FIGS. 2C-2E) or co-culturing (referred as CsgA-αγ$_{co-cultured}$) (FIG. 2F), showed fiber aggregation. Fibers did not bundle when only protein α (referred as CsgA-α based ECM) (FIG. 2A) or protein γ (referred as CsgA-γ based ECM) (FIG. 2B) was displayed on the genetically modified ECM. Similar findings were observed with reprogrammed bacterial cultures expressing keratin components. Fiber aggregation was only observed when proteins K5 and K14 were displayed together (referred as CsgA-K5K14 based ECM), either through mixing (referred as CsgA-K5K14$_{mixed}$) (FIGS. 3C-3E) or co-culturing (referred CsgA-K5K14$_{co-cultured}$) (FIG. 3F). Fibers did not aggregate when K5 (FIG. 3A) or K14 (FIG. 3B) (referred as CsgA-K5 and CsgA-K14 based ECM) was expressed alone.

Hydrogel Production

The production of fibrin and keratin inspired curli based hydrogels was successful. For the following sections the fibrin inspired hydrogels are labeled according to their composition and fabrication as: CsgA-α, CsgA-γ, CsgA-αγ$_{mixed}$ CsgA-αγ$_{co-cultured}$ based hydrogel. The keratin inspired hydrogels are also categorized in: CsgA-K5, CsgA-K14, CsgA-K5K14$_{mixed}$ CsgA-K15K14$_{co-cultured}$ based hydrogel. The production of all hydrogels was performed under the same condition. However, the quantity of gained hydrogels from 0.5 L volume of bacterial culture varied, as shown in Table 4.

TABLE 4

Quantity of fibrin and keratin inspired curli based hydrogels quantities

| Hydrogel type | Amount of gained hydrogel from 0.5 L volume of bacterial culture |
|---|---|
| CsgA-α | 0.20 ml |
| CsgA-γ | 0.75 ml |
| CsgA-αγ$_{mixed}$ | 0.50 ml |
| CsgA-αγ$_{mixed}$ | 0.60 ml |
| CsgA-K5 | 0.70 ml |
| CsgA-K14 | 0.70 ml |
| CsgA-K5K14$_{mixed}$ | 0.40 ml |
| CsgA-K5K14$_{co-cultured}$ | 0.40 ml |

The amount of gained CsgA-α based hydrogels was the lowest compared to all other hydrogels. The amount of produced CsgA-γ based hydrogels was in the same range as CsgA-K5 and CsgA-K14 based hydrogels. The quantity of CsgA-αγ$_{mixed}$, CsgA-αγ$_{co-cultured}$, CsgA-K5K14$_{mixed}$ and CsgA-K15K14$_{co-cultured}$ based hydrogel were similar, but 20 to 43% less than CsgA-γ, CsgA-K5 and CsgA-K14 respectively. Also, the appearance of the hydrogels was not the same for the different types. The hydrogels varied from transparent to more opaque.

Hydrogel Characterization

I. Hydrogel Morphology

Figure 4A:
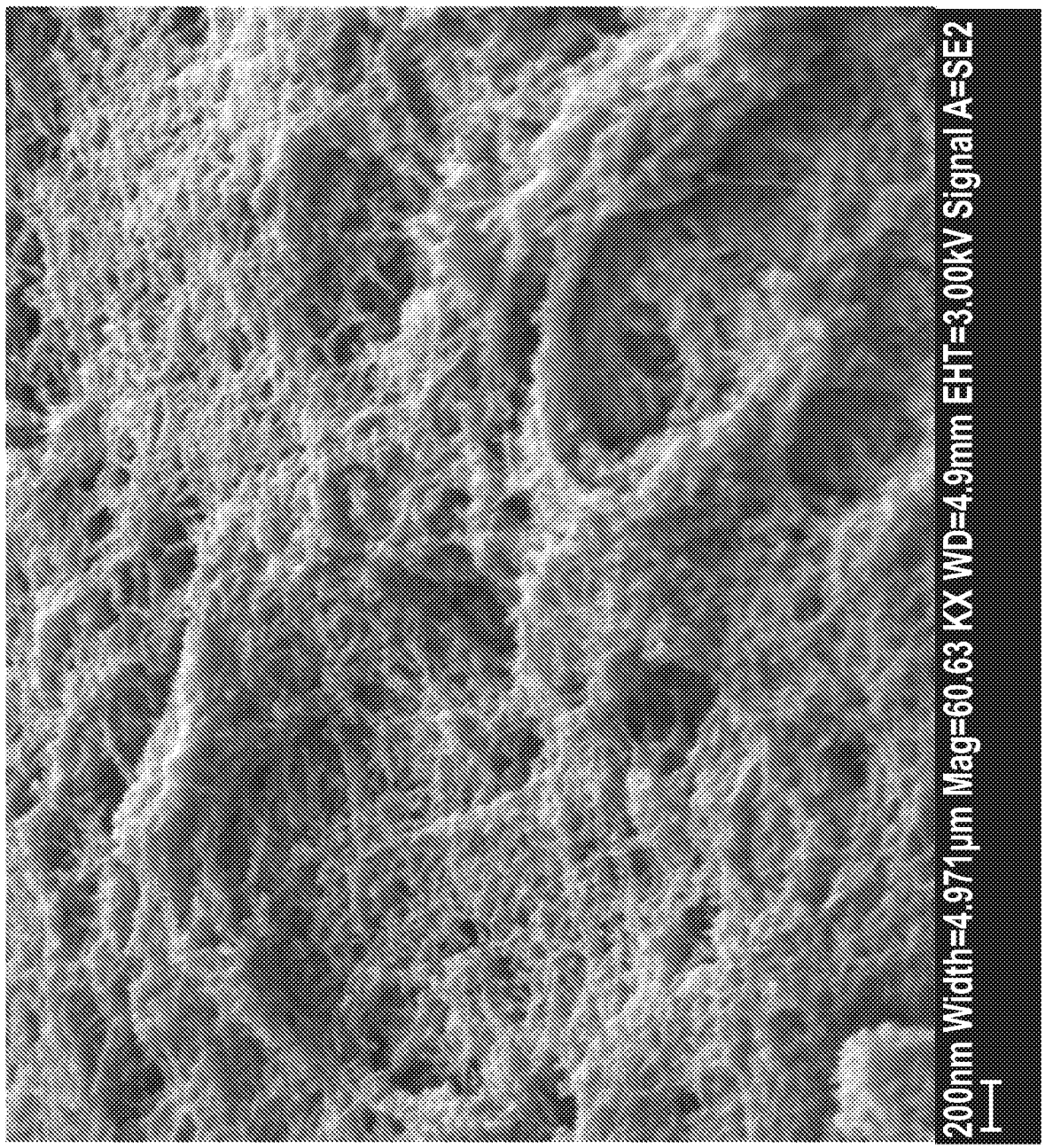
FIGS. 4A, 4B, 4C, and 4D depict the microstructure of fibrin inspired curli hydrogels.
Figure 4B:
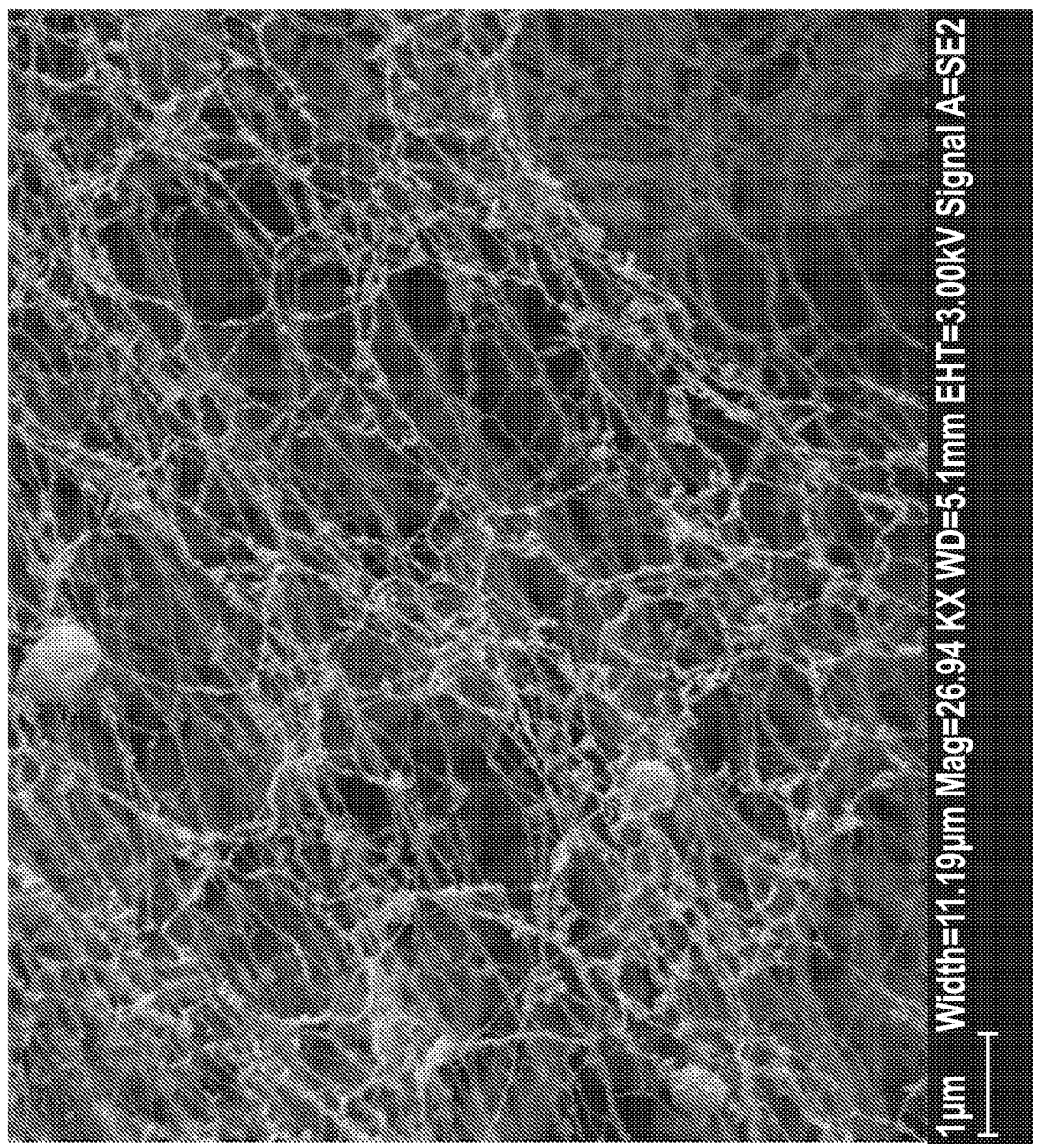
Figure 4C:
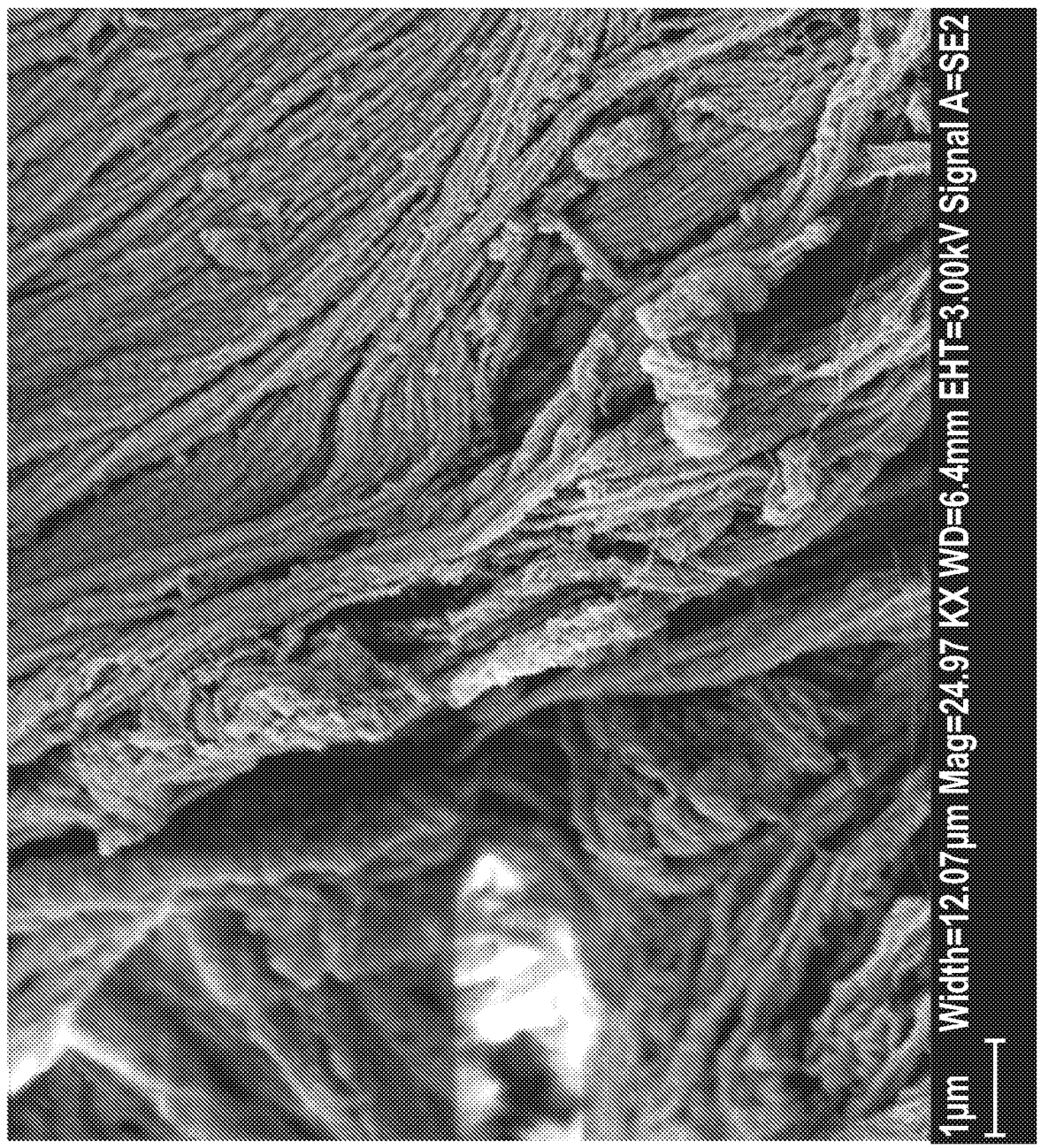
Figure 4D:
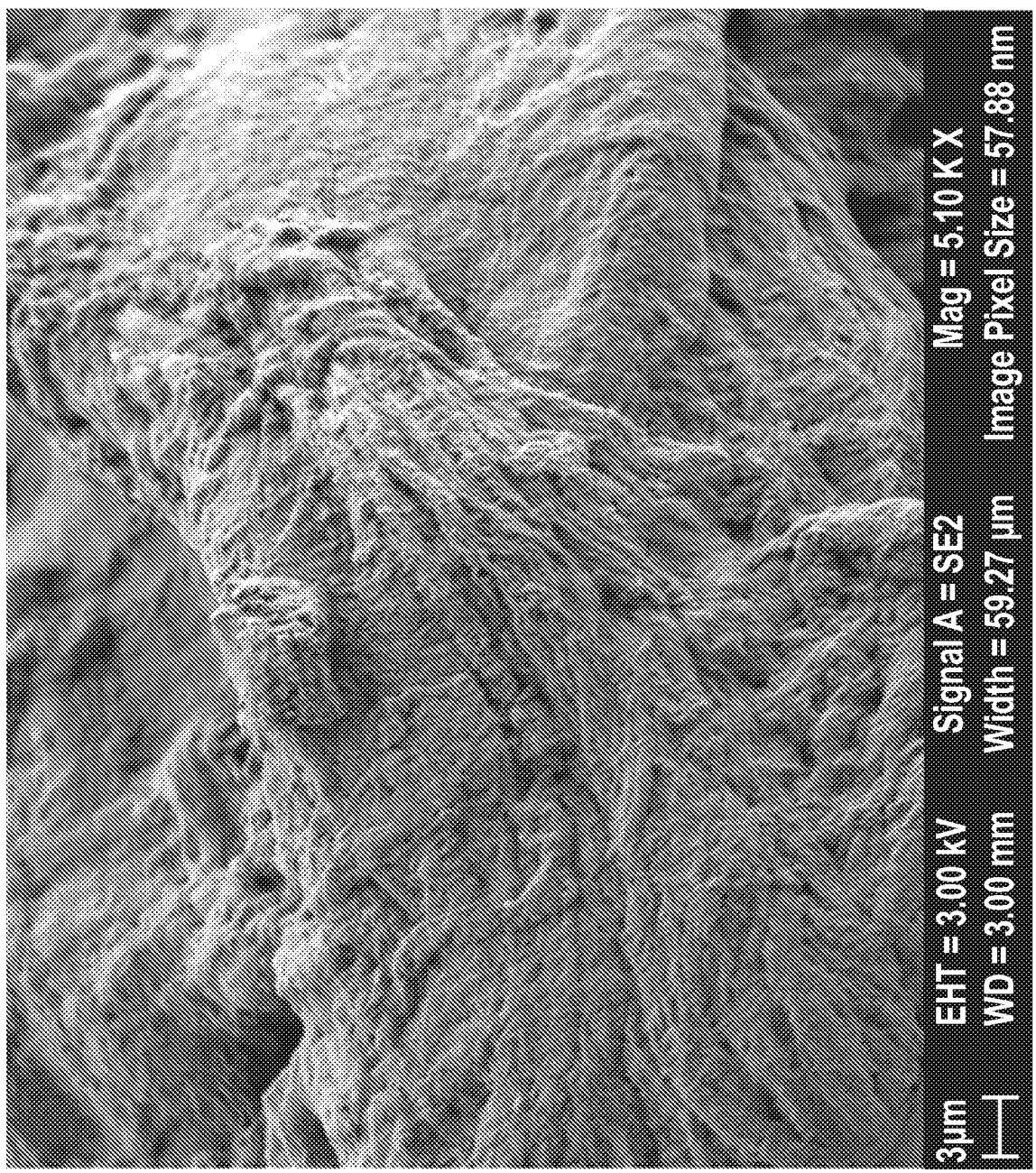
Figure 5:
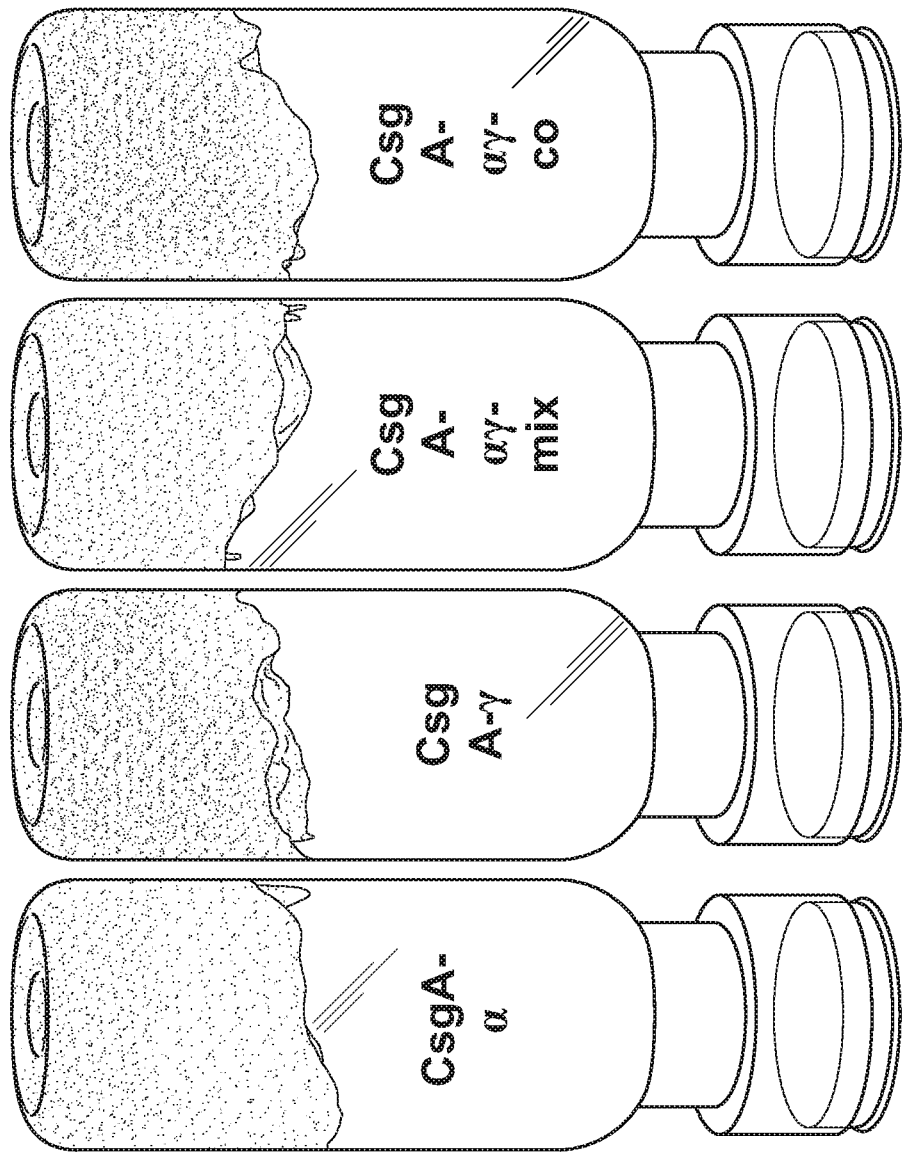
FIG. 5 depicts optical images of fibrin inspired curli hydrogels. From left to right are: CsgA-α based hydrogel, CsgA-γ based hydrogel, CsgA-$αγ_{mixed}$ based hydrogels, and CsgA-$αγ_{co-cultured}$ based hydrogel, respectively.

The morphology of the produced hydrogels was examined using SEM. The images revealed a change in microstructure among the different types of fibrin and keratin inspired hydrogels. The CsgA-α based hydrogel, which represents knob "A" of the fibrin network revealed a dense pore size structure (see FIG. 4A), whereas the CsgA-γ based hydrogel, which represents hole "a" of the fibrin network showed a bigger pore size structure (see FIG. 4B). However, a drastic change in the microstructure was observed in CsgA-$\alpha\gamma_{mixed}$ (FIG. 4C) and CsgA-$\alpha\gamma_{co\text{-}cultured}$ (FIG. 4D) based hydrogels. An aligned and very dense network of the fibers occurred as presented in FIGS. 4C-4D. The SEM images of keratin based hydrogels showed no difference in morphology among the different types. FIGS. 5A-5D depict the optical images of CsgA-α, CsgA-γ, CsgA-$\alpha\gamma_{mixed}$ and CsgA-$\alpha\gamma_{co\text{-}cultured}$ based hydrogels, respectively.

Mechanical Properties

All hydrogels were tested on a rheometer to evaluate the linear shear modulus. The hydrogels were grouped in fibrin and keratin inspired hydrogels. The quantified shear modulus for fibrin hydrogel is shown in FIG. 6.

Rheology Fibrin Inspired Hydrogels

Figure 6:
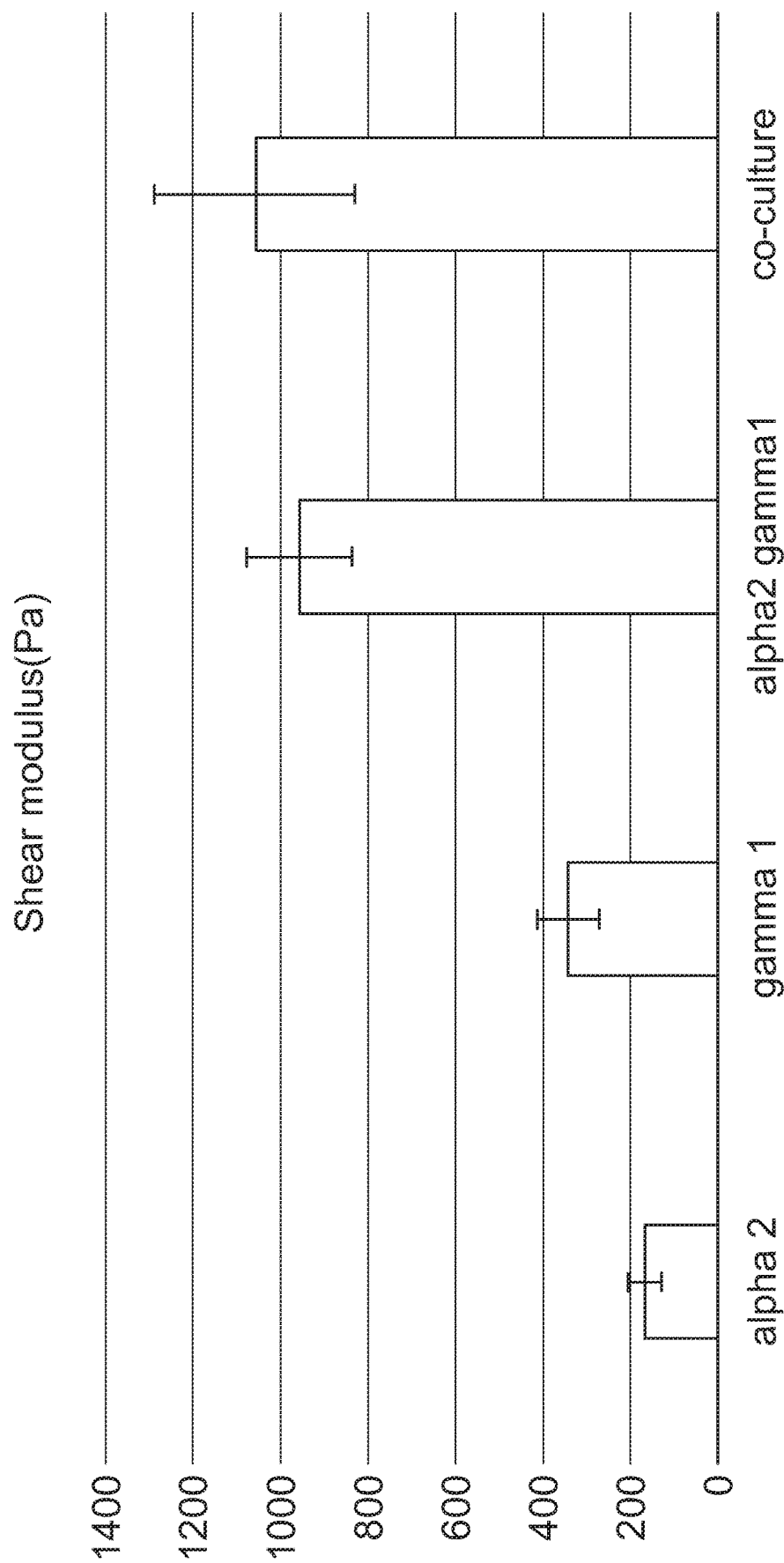
FIG. 6 depicts the mechanical properties of the four different types of fibrin inspired hydrogels.

The rheology of the fibrin inspired hydrogels revealed a significant increase in stiffness for CsgA-$\alpha\gamma_{mixed}$ and CsgA-$\alpha\gamma_{co\text{-}cultured}$ compared to CsgA-α and CsgA-γ based hydrogels as shown in FIG. 6. Also a difference in the shear modulus between CsgA-α and CsgA-γ based hydrogels was detectable. The CsgA-γ hydrogel was almost twice as stiff as the CsgA-α hydrogel. The increase in shear modulus for CsgA-$\alpha\gamma_{mixed}$ and CsgA-$\alpha\gamma_{co\text{-}cultured}$ based hydrogels was about six times compared to CsgA-α and approximately three times compared to CsgA-γ hydrogels. However, the shear modulus for CsgA-$\alpha\gamma_{mixed}$ and CsgA-$\alpha\gamma_{co\text{-}cultured}$ hydrogels was in the same range. The mean value for CsgA-α hydrogel was 166.49 Pa, 342.15 Pa for CsgA-γ hydrogel, 955.15 Pa for CsgA-$\alpha\gamma_{mixed}$ and 1057.67 Pa for CsgA-$\alpha\gamma_{co\text{-}cultured}$ hydrogel.

Figure 8:
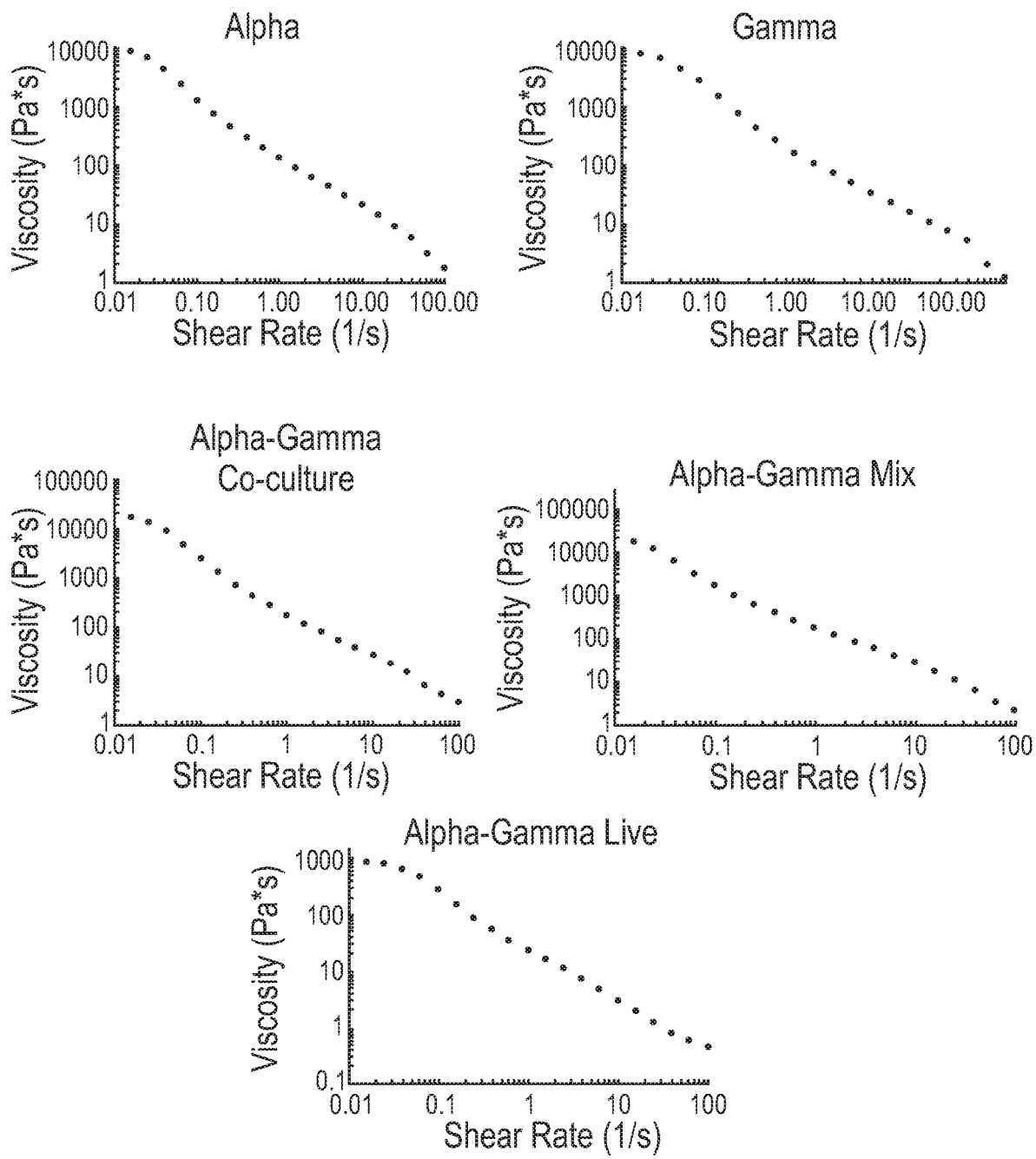
FIG. 8 depicts rheology properties of the 3D printing bacto-ink made from curli variants (CsgA-$αγ_{mixed}$ or CsgA-$αγ_{co-cultured}$) without presence of bacteria or with bacteria (alpha-gamma live) or its single components alpha or gamma. The steady-state flow behavior of the inks is measured by viscosity curves at increasing and decreasing shear rates.
Figure 9A:
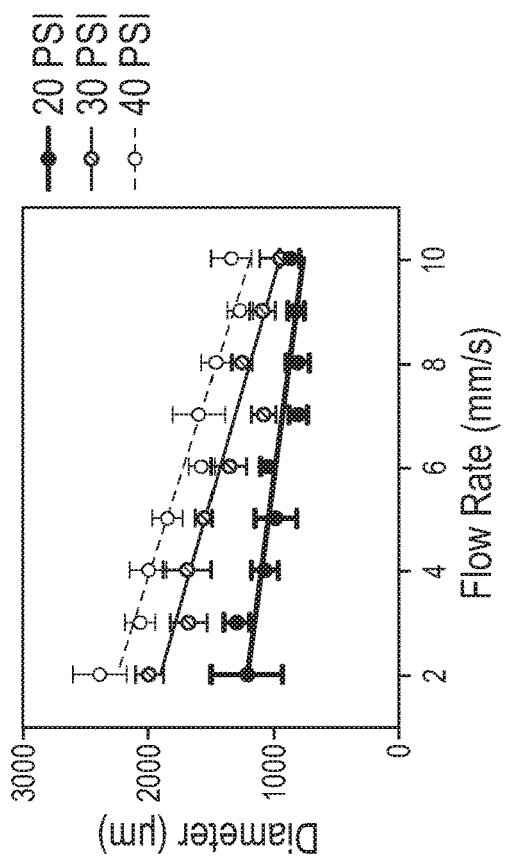
FIGS. 9A, 9B, 9C, and 9D depict 3D printing performance of CsgA-α (FIG. 9A), CsgA-γ (FIG. 9B), CsgA-$αγ_{mixed}$ (FIG. 9C), and CsgA-$αγ_{co-cultured}$ (FIG. 9D), respectively. 3D printing performance was measured by the cross length of the printed filaments as a function of flow rate under a broad range of extrusion pressure.
Figure 9B:
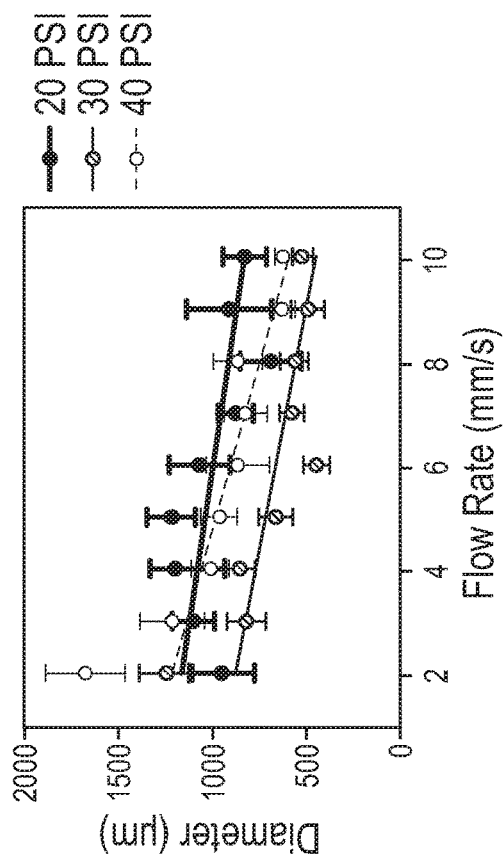
Figure 9C:
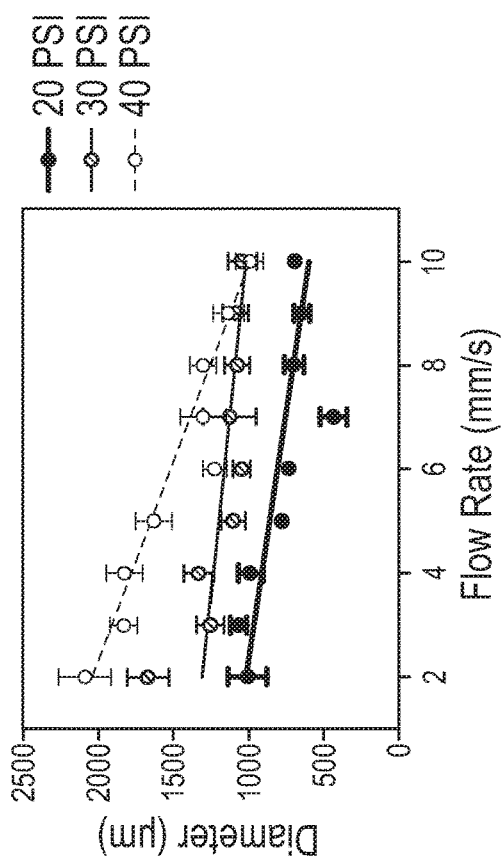
Figure 9D:
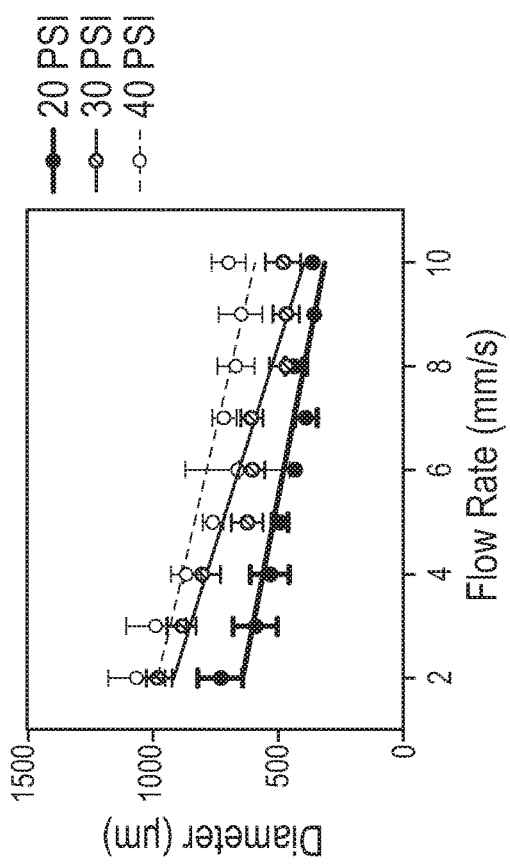
Figure 10B:
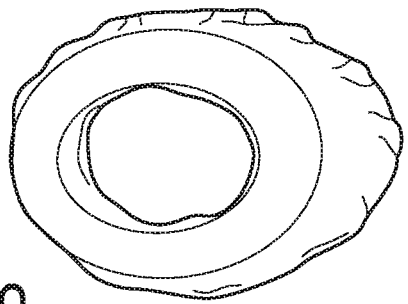
FIGS. 10A, 10B, 10C, and 10D depict 3D printing using bacto-ink made from curli variant CsgA-$αγ_{co-cultured}$ into a 10-layered circle (FIGS. 10A and 10B) or a 10-layered square (FIGS. 10C and 10D).
Figure 10D:
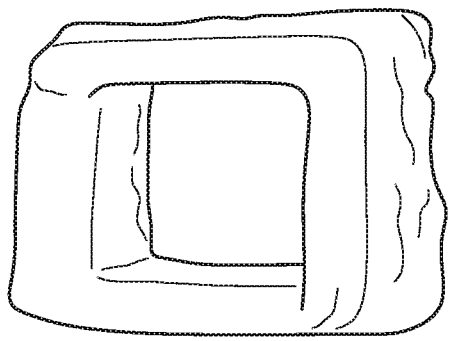
Figure 10A:
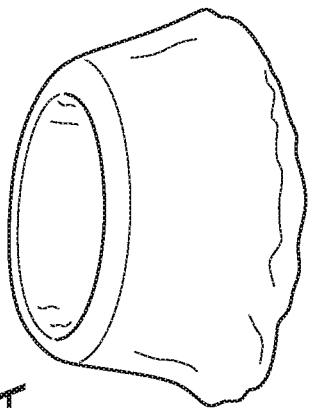
Figure 10C:
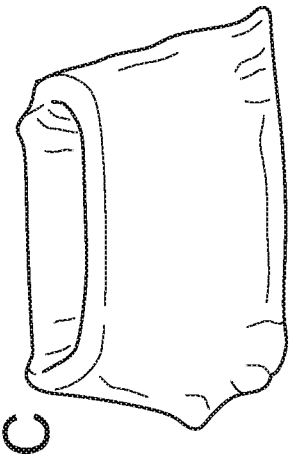

Further tests were conducted to characterize the viscosity of the CsgA-$\alpha\gamma_{mixed}$ and CsgA-$\alpha\gamma_{co\text{-}cultured}$ based hydrogels, compared to CsgA-α and CsgA-γ based hydrogels, as well as CsgA-γ-producing live bacteria. As shown in FIG. 8, the viscosity of CsgA-$\alpha\gamma_{mixed}$ and CsgA-$\alpha\gamma_{co\text{-}cultured}$ based hydrogels is higher than CsgA-α and CsgA-γ based hydrogels, or CsgA-γ-producing live bacteria alone, demonstrating the advantageous properties of the mixed or co-cultured hydrogels for use as 3D-printing inks.

Similarly, as shown in FIGS. 9A-9D, CsgA-$\alpha\gamma_{mixed}$ and CsgA-$\alpha\gamma_{co\text{-}cultured}$ based hydrogels demonstrate better rheological properties and 3D printing performances compared to CsgA-α and CsgA-γ based hydrogels for use as 3D-printing inks.

Rheology Keratin Inspired Hydrogels

The rheology of keratin inspired hydrogels revealed small changes in the shear modulus between its different types. The shear modulus of CsgA-K5 and CsgA-K14 was about the same with approximately only 10% variation. An increase in shear modulus of approximately 38% for CsgA-K5K14$_{mixed}$ based hydrogels was achieved compared to CsgA-K5 and about 25% compared to CsgA-K14 hydrogels. The increase in shear modulus for CsgA-K5K14$_{co\text{-}cultured}$ hydrogel was approximately 17% compared to CsgA-K5 and around 6% compared to CsgA-K14 hydrogel. However, a difference of about 17% in shear modulus between CsgA-K5K14$_{mixed}$ and CsgA-K5K14$_{co\text{-}cultured}$ based hydrogel was detectable. The mean value for CsgA-K5 hydrogel was 592.37 Pa, 651.17 Pa for CsgA-K14 hydrogel, 817.14 Pa for CsgA-K5K14$_{mixed}$ hydrogel and 693.67 Pa for CsgA-K5K14$_{co\text{-}cultured}$ hydrogel.

"3D Printing" with CsgA-αγ Based Hydrogel

Figure 7:
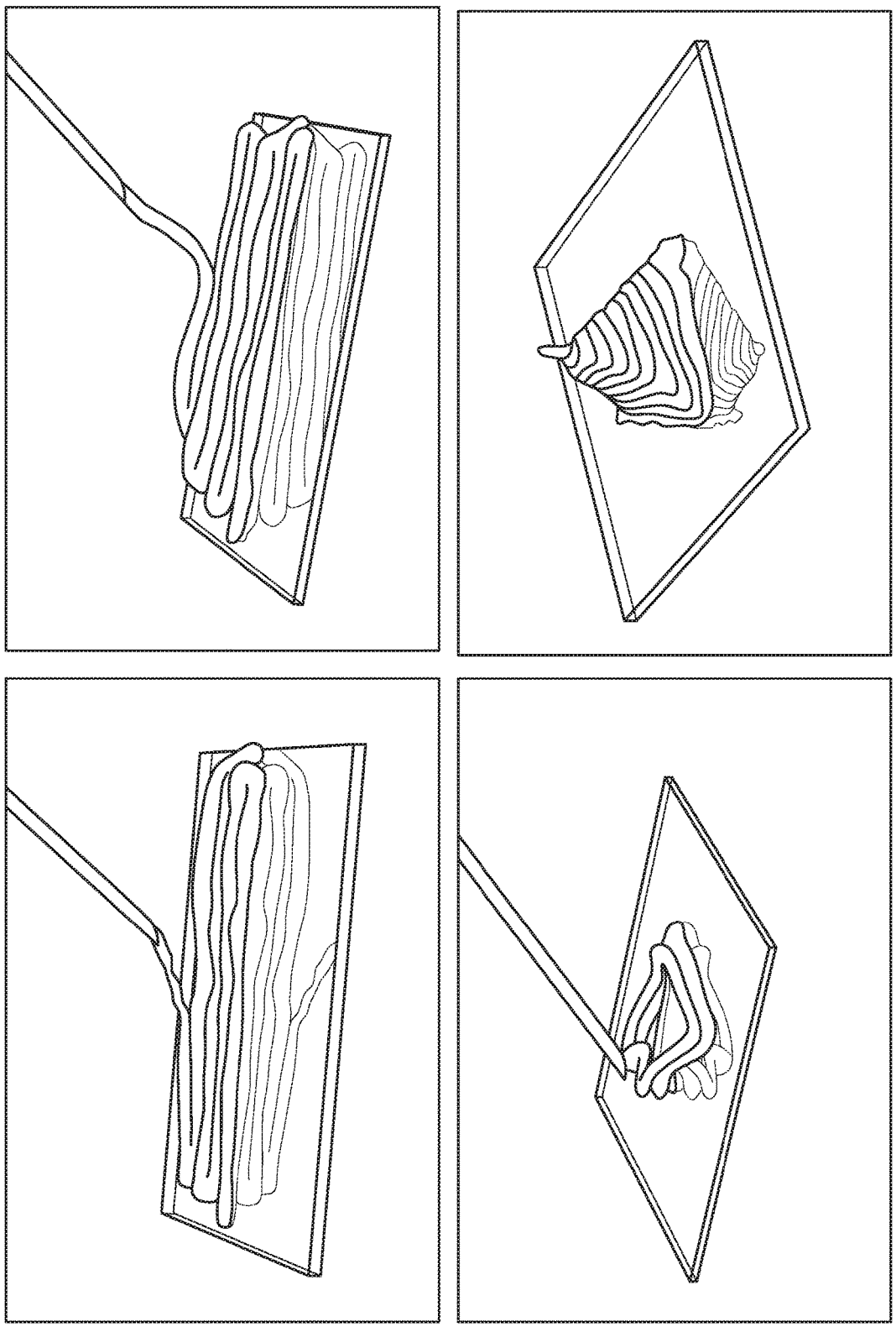
FIG. 7 depicts 3D structure construction with fibrin inspired hydrogels.

Based on the shear thinning characteristics and to prove that fibrin inspired hydrogels can be used for future medical applications in tissue engineering, they were tested as inks for "3-dimensional (3D) printing". To test the ability of the hydrogels in forming 3D-structures, CsgA-αγ based hydrogel was loaded into a syringe and pressed through a needle. The hydrogel maintained its properties after injected through the needle and it was able build stable 3D constructs, as shown in FIG. 7. As further depicted in FIGS. 10A-10D, CsgA-$\alpha\gamma_{co\text{-}cultured}$ based hydrogel was built into a 10-layered circle or square, further demonstrating the ability of the hydrogel of the invention to be used as 3D-printing inks. These findings add up with the mechanical characterization of the gels with the rheological tests.

To further study the bacto-inks of the current invention for functional applications on bioactivity, sensing and binding, the bacto-inks, e.g., BactoPrink containing CsgA-α, CsgA-γ, CsgA-$\alpha\gamma_{mixed}$ or CsgA-$\alpha\gamma_{co\text{-}cultured}$ based hydrogels, are further combined with functional curli fibers, or engineered living bacteria to produce functional bacto-inks for use in applications such as bio sensing, signaling, binding, or other bioactivities.

Figure 11A:
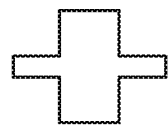
FIGS. 11A, 11B, and 11C are schematic illustrations of 3D printing inks made from fibrin inspired CsgA-α, CsgA-γ, CsgA-$αγ_{mixed}$ and/or CsgA-$αγ_{co-cultured}$ bacto-inks combined with functional curli fibers (FIG. 11A); combined with engineered living microbes (FIG. 11B); or combined with engineered living bacteria that can express functional curli fibers after printing and upon specific induction for secretion (FIG. 11C).

As depicted in FIG. 11A, functional curli fibers were added to the cultures of BactoPrink (containing CsgA-α, CsgA-γ, CsgA-$\alpha\gamma_{mixed}$ or CsgA-$\alpha\gamma_{co\text{-}cultured}$ based hydrogels) and the functional inks were prepared using the protocol described in the previous sections. The resulting inks were utilized for functional applications like bioactivity, sensing and binding.

Figure 11B:
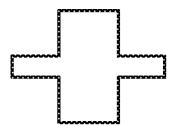

As depicted in FIG. 11B, engineered living microbial cultures were incubated with BactoPrink (containing CsgA-α, CsgA-γ, CsgA-$\alpha\gamma_{mixed}$ or CsgA-$\alpha\gamma_{co\text{-}cultured}$ based hydrogels) for 10 min and vacuum filtered to drain out excess water, which was then mixed manually to obtain a living microbial ink. Such living microbial inks were 3D printed and immersed in microbial medium having specific antibiotics and/or inducers. The living microbes in the ink were thus utilized for functional applications like secretion, bioactivity, signaling, sensing and binding.

Figure 11C:
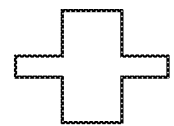

As depicted in FIG. 11C, engineered living bacterial cultures were incubated with BactoPrink (containing CsgA-α, CsgA-γ, CsgA-$\alpha\gamma_{mixed}$ or CsgA-$\alpha\gamma_{co\text{-}cultured}$ based hydrogels) for 10 min and vacuum filtered to drain out excess water, which was then mixed manually to obtain a living microbial ink. Such living microbial inks were 3D printed and immersed in bacterial medium having specific antibiotics and/or inducers, so as to secrete functional curli fibers in situ. The inks were then utilized for functional applications like bioactivity, secretion, signaling, sensing, binding and self-regeneration of BactoPrink.

As depicted in FIGS. 12A and 12B, Bactoprink containing CsgA-$\alpha\gamma_{co\text{-}cultured}$ based hydrogels was combined with living bacteria producing CsgA-α and CsgA-γ and was printed into a grid pattern (FIG. 12A). Two days after the printing, the living bacteria combined with the CsgA-$\alpha\gamma_{co\text{-}cultured}$ based hydrogels were able to proliferate and/or produce more curli fibers (FIG. 12B), demonstrating the ability of the Bactoprink of self-regeneration.

Figure 13:
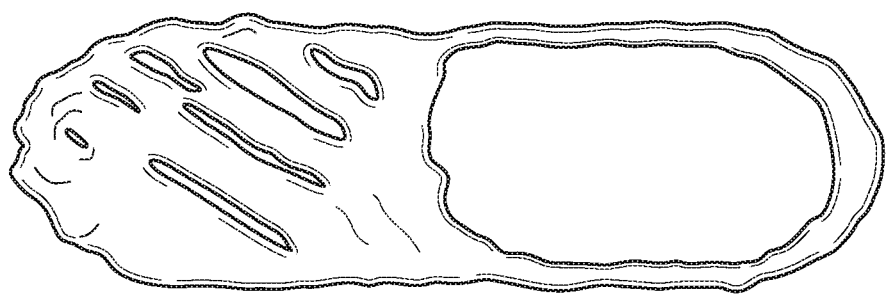
FIG. 13 depicts a capsule-like 3D printed pattern from a bacto-ink comprising CsgA-$αγ_{cocultured}$ and bacteria that secrete an anti-cancer drug, azurin.

As depicted in FIG. 13, a BactoPrink containing a CsgA-$\alpha\gamma_{co\text{-}cultured}$ based hydrogel and live bacteria secreting an anti-cancer drug, azurin was produced and used as 3D-printing ink to print a capsule-like pattern.

Figure 14:
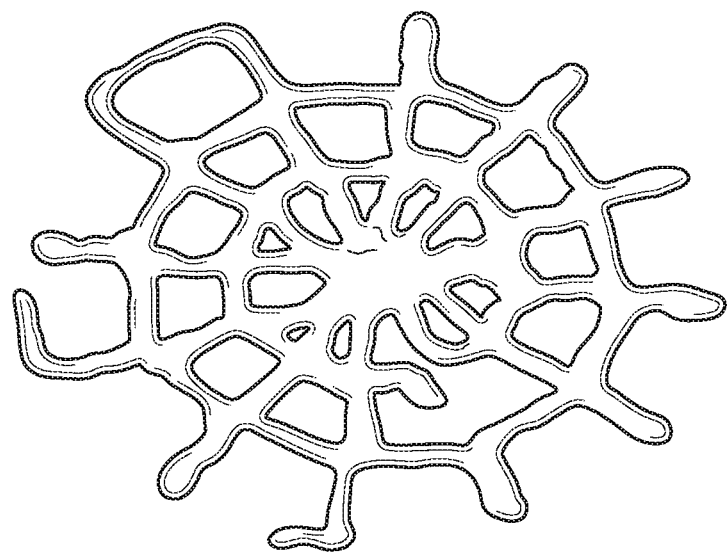
FIG. 14 depicts a spider-web like 3D printed pattern from a bacto-ink comprising CsgA-$αγ_{cocultured}$ and bacteria that secrete a functional curli fiber comprising a BPA (Bisphenol A) binding domain fused to the c-terminus of CsgA.

As depicted in FIG. 14, a BactoPrink containing a CsgA-$\alpha\gamma_{co\text{-}cultured}$ based hydrogel and live bacteria producing a functional curli fiber expressing a BPA (Bisphenol A) binding domain fused to the c-terminus of CsgA was produced and used as 3D-printing ink to print a spiderweb-like pattern.

Example 4: Conclusion

On the basis of the presented results, especially for mimicked fibrin, it can be concluded that described herein is a unique method to mimic fibrin and keratin. Firstly, the images on the bright-field microscope clearly indicate interaction of fibrin and keratin derived proteins when mixed or co-cultured. Secondly, for mimicked fibrin, the rheology showed a significant increase in stiffness of CsgA-ay based hydrogels suggesting that upon designed knob-hole interaction the hydrogel structure is being strengthened. Also, due to its mechanical properties the fibrin based hydrogels of $\alpha\gamma_{mixed}$ and $\alpha\gamma_{co\text{-}cultured}$ function as an excellent platform for "3D printing". Third, the interaction of $\alpha$ and $\gamma$ led to a dramatic change in the morphology of the fibrin inspired hydrogels.

Also demonstrated herein is a method of "3D printing" with fibrin inspired hydrogels, which can be used to fabricate scaffolds for wound healing in tissue engineering applications, or for drug delivery. Because existing methods for extraction and synthesis of keratin from keratin rich sources is still poor, the system disclosed herein is an ideal alternative platform to fabricate keratin based biomaterials. Those materials could be used to produce cost efficient scaffolds or coating agents to study cell behavior in cell culturing and tissue engineering applications. Moreover, because the presented system allows to display exclusively one protein or a variety of different proteins, it can be used to also personalize the scaffolds or coating materials with varying concentrations of displayed fibrin or keratin derived proteins.

The invention claimed is:

1. An amyloid fusion protein comprising an amyloid protein fused to fibrin, a fragment of fibrin, K5 keratin, or K14 keratin.

2. The amyloid fusion protein of claim 1, wherein the amyloid protein is selected from the group consisting of CsgA and fragments thereof, A-beta, alpha-synuclein, TasA, and Sup35.

3. The amyloid fusion protein of claim 1, wherein the amyloid protein is CsgA, or a fragment thereof.

4. The amyloid fusion protein of claim 1, wherein amyloid protein is fused to fibrin.

5. The amyloid fusion protein of claim 1, wherein the amyloid protein is fused to a fragment of fibrin.

6. The amyloid fusion protein of claim 1, wherein the fibrin or the fragment of fibrin fibrous protein comprises an α chain of fibrinogen.

7. The amyloid fusion protein of claim 1, wherein the fibrin or the fragment of fibrin comprises a γ chain of fibrinogen.

8. The amyloid fusion protein of claim 1, wherein the amyloid protein is fused to K5 keratin.

9. The amyloid fusion protein of claim 1, wherein the amyloid protein is fused to K14 keratin.

10. A plurality of amyloid fusion proteins comprising a first amyloid fusion protein and a second amyloid fusion protein,
wherein the first amyloid fusion protein is a fusion protein of claim 1; and
wherein the second amyloid fusion protein is a fusion protein of claim 1,
wherein the first amyloid fusion protein is aggregated with the second amyloid fusion protein.

11. The plurality of amyloid fusion proteins of claim 10, wherein the first amyloid fusion protein comprises an α chain of fibrinogen; and the second amyloid fusion protein comprises an α chain of fibrinogen.

12. The plurality of amyloid fusion proteins of claim 10, wherein the first amyloid fusion protein comprises K5 keratin; and the second amyloid fusion protein comprises K14 keratin.

13. The plurality of amyloid fusion proteins of claim 10, wherein the first and second amyloid proteins are selected from the group consisting of CsgA and fragments thereof, A-beta, alpha-synuclein, TasA, and Sup35.

14. The plurality of amyloid fusion proteins of claim 13, wherein the first and second amyloid proteins are CsgA, or a fragment thereof.

15. The plurality of amyloid fusion proteins of claim 14, wherein the CsgA, or fragment thereof, is an E. coli CsgA, or fragment thereof.

16. A plurality of curli fibers comprising the plurality of amyloid fusion proteins of claim 10.

17. A fibrous proteinaceous network comprising the plurality of amyloid fusion proteins of claim 10.

18. A biomaterial comprising the amyloid fusion protein or the plurality of amyloid fusion proteins of claim 10.

19. The biomaterial of claim 18, further comprising an engineered microbial cell that expresses one or more functional curli fibers.

20. The biomaterial of claim 18, further comprising a functional curli fiber, wherein the functional curli fiber is a fusion of a CsgA protein linked to a non-native functional polypeptide.

21. The biomaterial of claim 20, wherein the non-native functional polypeptide is a therapeutic polypeptide, a diagnostic polypeptide, a tissue-binding polypeptide, a cell-binding polypeptide, an antimicrobial polypeptide, an anticancer polypeptide, an anti-inflammatory polypeptide, a polymer-binding polypeptide, a metabolite-binding polypeptide, a targeting polypeptide, or a polypeptide that is part of a binding pair of molecules.

22. A hydrogel comprising the amyloid fusion protein or the plurality of amyloid fusion proteins of claim 10.

23. A bioink comprising the biomaterial of claim 18.

24. A method of producing the biomaterial of claim 18, comprising
culturing a first genetically engineered bacterium in culture media, wherein the first genetically engineered bacterium expresses a first amyloid protein fused to fibrin, a fragment of a fibrin, K5 keratin, or K14,
culturing a second genetically engineered bacterium in the culture media, wherein the second genetically engineered bacterium expresses a second amyloid protein fused to fibrin, a fragment of a fibrin, K5 keratin, or K14,
wherein the first amyloid protein fused to a fibrin, a fragment of fibrin, K5 keratin, or K14 keratin aggregates to the second amyloid protein fused to fibrin, a fragment of a fibrin, K5 keratin, or K14 keratin, thereby forming the fibrous proteinaceous network.

25. The method of claim 24, further comprising forming a bioink.

* * * * *